US008440657B2

(12) United States Patent
Heimbach et al.

(10) Patent No.: US 8,440,657 B2
(45) Date of Patent: May 14, 2013

(54) SUBSTITUTED PIPERIDINES

(75) Inventors: Dirk Heimbach, Düsseldorf (DE);
Susanne Röhrig, Hilden (DE); Yolanda Cancho Grande, Leverkusen (DE);
Eckhard Bender, Langenfeld (DE);
Katja Zimmermann, Düsseldorf (DE);
Anja Buchmüller, Essen (DE);
Christoph Gerdes, Köln (DE); Mark Jean Gnoth, Mettmann (DE); Kersten Matthias Gericke, Wuppertal (DE);
Mario Jeske, Solingen (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/322,593

(22) PCT Filed: May 18, 2010

(86) PCT No.: PCT/EP2010/003024
§ 371 (c)(1),
(2), (4) Date: Feb. 17, 2012

(87) PCT Pub. No.: WO2010/136138
PCT Pub. Date: Dec. 2, 2010

(65) Prior Publication Data
US 2012/0135985 A1 May 31, 2012

(30) Foreign Application Priority Data
May 27, 2009 (DE) .......................... 10 2009 022 894

(51) Int. Cl.
*C07D 417/14* (2006.01)
*A61K 31/541* (2006.01)
(52) U.S. Cl.
USPC ..................................... 514/227.8; 544/58.2
(58) Field of Classification Search ................ 514/227.8
See application file for complete search history.

(56) References Cited

U.S. PATENT DOCUMENTS

| | | | |
|---|---|---|---|
| 5,767,144 | A | 6/1998 | Winn et al. |
| 8,084,469 | B2 | 12/2011 | Heimbach et al. |
| 8,119,663 | B2 | 2/2012 | Heimbach et al. |
| 8,202,862 | B2 | 6/2012 | Heimbach et al. |
| 2001/0044454 | A1 | 11/2001 | Nantermet et al. |
| 2005/0004170 | A1 | 1/2005 | Janssens et al. |
| 2006/0004049 | A1 | 1/2006 | Yao et al. |
| 2007/0197530 | A1 | 8/2007 | Li et al. |
| 2008/0003214 | A1 | 1/2008 | Cezanne et al. |
| 2011/0021489 | A1 | 1/2011 | Heimbach et al. |
| 2012/0046268 | A1 | 2/2012 | Jeske et al. |
| 2012/0129831 | A1 | 5/2012 | Heimbach et al. |
| 2012/0142690 | A1 | 6/2012 | Heimbach et al. |
| 2012/0149694 | A1 | 6/2012 | Heimbach et al. |

FOREIGN PATENT DOCUMENTS

| | | |
|---|---|---|
| WO | 97/36873 A1 | 10/1997 |
| WO | 2006/002350 A1 | 1/2006 |
| WO | 20061002349 A1 | 1/2006 |
| WO | 2006/012226 A2 | 2/2006 |
| WO | 2006/020598 A2 | 2/2006 |
| WO | 2007/038138 A2 | 4/2007 |
| WO | 2007/101270 A2 | 9/2007 |
| WO | 2007/130898 A1 | 11/2007 |
| WO | 2009/068214 A2 | 7/2009 |
| WO | 2009/068214 A3 | 7/2009 |

OTHER PUBLICATIONS

Jon D. Horton, Pharm.D., and Bruce M. Bushwick, M.D., York Hospital, York, Pennsylvania Am Fam Physician. Feb. 1, 1999;59(3):635-646. (19 pages).*
Barrow et al.: "Discovery and Initial Structure-Activity Relationships of Trisubstituted Ureas as Thrombin Receptor (PAR-1) Antagonists," Bioorganic & Medicinal Chemistry Letters, Apr. 30, 2001, pp. 2691-2696.
Chackalamannil: "Thrombin Receptor (Protease Activated Receptor-1) Antagonists as Potent Antithrombotic Agents with Strong Antiplatelet Effects," Journal of Medicinal Chemistry, Sep. 7, 2006, 49(18): 5389-5404.
Diaz. et al.,: "Fast Efficient Access to a Family of Multifunctional 1,3,5-Trisubstituted Piperidines," Synthetic Communications, 2008, 38:2977-2813.
McAtee et al.: "Development of Potent and Selective Small-Molecule Human Urotensin-II Antagonists," Bioorganic and Medicinal Chemistry Letters, 2008, 18: 3500-3503.
Morissette et al.: "High-throughput Crystallization: Polymorphs, Salts, Co-crystals, and Solvates of Pharmaceutical Solids," Advanced Drug Delivery Reviews, 2004, 56: 275-300.
Vippagunta et al.: "Crystalline Solids," Advanced Drug Delivery Reviews, 2001, 48: 3-26.
Golub et al.: Molecular Classification of Cancer: Class Discovery and Class Prediction by Gene Expression Monitoring,: Science, 1999, 286: 531-537.
Lala et al.: "Role of Nitric Oxide in Tumor Progression: Lessons from Experimental Tumors," Cancer and Metastasis Reviews, 1998, 17: 91-106.
Vu et al.: "Molecular Cloning of a Functional Thrombin Receptor Reveals a Novel Proteolytic Mechanism of Receptor Activation," Cell, Mar. 22, 1991, 64:1057-1068.
Bhatt et al.: "Scientific and Theraputic Advances in Antiplatelet Therapy," Nat. Rev. Drug Discov., Jan. 2003, 2:15-28.
Kahn et al.: "Protease-Activated Receptors 1 and 4 Mediate Activation of Human Platelets by Thrombin," J. Clin. Invest., 1999, 103: 879-887.
Nigel Mackman, "Triggers, targets, and treatments for thrombosis," Nature, Feb. 2008, 451: 914-919.
Derian et al.: "Blocade of the Thrombin Receptor Protease-Activated Receptor-1 with a Small-Molecule Antagonist Prevents Thrombus Formation and Vascular Occlusion in Nonhuman Primates," J. Pharmacol. Exp. Ther., 2003, 304 (2):855-861.

(Continued)

*Primary Examiner* — Kahsay T Habte
(74) *Attorney, Agent, or Firm* — Karen B. King

(57) ABSTRACT

The invention relates to novel substituted piperidines, to processes for preparation thereof, to the use thereof for treatment and/or prophylaxis of diseases and to the use thereof for production of medicaments for treatment and/or prophylaxis of diseases, especially of cardiovascular diseases and tumour diseases.

23 Claims, No Drawings

OTHER PUBLICATIONS

Dellinger et al.: "Surviving Sepsis Campaign Guidelines for Management of Severe Sepsis and Septic Shock," Crit. Care Med., 2004, 32(3):858-873.

Mochizuki et al.: "Design, Synthesis, and Biological Activity of Piperdine Diamine Derivatives as Factor Xa Inhibitor," Bioorganic & Medicinal Chemistry Letters 18, 2008, pp. 783-787.

Meadows, Telly A et al., "Clinical Aspects of Platelet Inhibitors and Thrombus Formation," Circulation Research, May 11, 2007, pp. 1261-1275.

Chintala M, et al., "Basic and translational research on proteinase-activated receptors: antagonism of the proteinase-activated receptor 1 for thrombin, a novel approach to antiplatelet therapy for atherothrombotic disease," J Pharmacol Sci, 2008, 108: 433-438.

Angiolillo DJ, et al., "Clinical overview of promising nonthienopyridine antiplatelet agents," Am Heart J, 2008, 156:S23-S28.

Gawaz M, et al., "Incomplete inhibition of platelet aggregation and glycoprotein IIb-IIIa receptor blockade by abciximab: importance of internal pool of glycoprotein IIb-IIIa receptors," Thromb Haemost, 2000, 83:915-922.

Ahn H-S, et al., "Nonpeptide thrombin receptor antagonists," Drugs of the Future, 2001, 26:1065-1085, at p. 1077.

Becker RC, et al., "Safety and tolerability of SCH 530348 in patients undergoing non-urgent percutaneous coronary intervention: a randomised, double-blind, placebo-controlled phase II study," Lancet, 2009, 373: 919-928.

Day JRS, et al., "Clinical inhibition of the seven-transmembrane thrombin receptor (PAR1) by intravenous aprotonin during cardiothoracic surgery," Circulation, 2004, 110:2597-2600.

Howell CD, et al., "Absence of proteinase-activated receptor-1 signaling affords protection from bleomycin-induced lung inflammation and fibrosis," Am J Pathol, 2005, 166:1353-1365.

Landis C, "Pharmacologic strategies for combating the inflammatory response," J Am Soc Extracorporeal Technology, 2007, 39:291-295.

TRA-CER executive and steering committees, "The thrombin receptor antagonist for clinical event reduction in acute coronary syndrome (TRA-CER) trial: study design and rationale," Am Heart J, 2009, 158:327-334.

Stedman's Medical Dictionary, 27th Edition, pub. Lippincott Williams & Wilkins, 2000 copyright, title page, inside cover page, and p. 1458.

* cited by examiner

SUBSTITUTED PIPERIDINES

The invention relates to novel substituted piperidines, to processes for preparation thereof, to the use thereof for treatment and/or prophylaxis of diseases and to the use thereof for production of medicaments for treatment and/or prophylaxis of diseases, especially of cardiovascular diseases and tumour diseases.

Thrombocytes (blood platelets) are a significant factor both in physiological haemostasis and in thromboembolic disorders. In the arterial system in particular, platelets are of central importance in the complex interaction between blood components and the wall of the vessel. Unwanted platelet activation may, as a result of formation of platelet-rich thrombi, lead to thromboembolic disorders and thrombotic complications with life-threatening conditions.

One of the most potent platelet activators is the blood coagulation protease thrombin, which is formed at injured blood vessel walls and which, in addition to fibrin formation, leads to the activation of platelets, endothelial cells and mesenchymal cells (Vu T K H, Hung D T, Wheaton V I, Coughlin S R, Cell 1991, 64, 1057-1068). In platelets in vitro and in animal models, thrombin inhibitors inhibit platelet aggregation and the formation of platelet-rich thrombi. In man, arterial thromboses can be prevented or treated successfully with inhibitors of platelet function and thrombin inhibitors (Bhatt D L, Topol E J, Nat. Rev. Drug Discov. 2003, 2, 15-28). Accordingly, there is a high probability that antagonists of thrombin action on blood platelets reduce the formation of thrombi and the occurrence of clinical sequelae such as myocardial infarction and stroke. Other cellular effects of thrombin, for example on endothelial and smooth muscle cells of vessels, leukocytes and fibroblasts, are possibly responsible for inflammatory and proliferative disorders.

At least some of the cellular effects of thrombin are mediated via a family of G-protein-coupled receptors (Protease Activated Receptors, PARs), the prototype of which is the PAR-1 receptor. PAR-1 is activated by bindung of thrombin and proteolytic cleavage of its extracellular N-terminus. The proteolysis exposes a new N-terminus having the amino acid sequence SFLLRN . . . , which, as agonist ("tethered ligand"), leads to intramolecular receptor activation and transmission of intracellular signals. Peptides derived from the tethered ligand sequence can be used as agonists of the receptor and, on platelets, lead to activation and aggregation. Other proteases are likewise capable of activating PAR-1; these proteases include, for example, plasmin, factor VIIa, factor Xa, trypsin, activated protein C (aPC), tryptase, cathepsin G, proteinase 3, granzyme A, elastase and matrix metalloprotease 1 (MMP-1).

In contrast to the inhibition of protease activity of thrombin with direct thrombin inhibitors, blockade of PAR-1 should result in an inhibition of platelet activation without reduction in the coagulability of the blood (anticoagulation).

Antibodies and other selective PAR-1 antagonists inhibit the thrombin-induced aggregation of platelets in vitro at low to medium thrombin concentrations (Kahn M L, Nakanishi-Matsui M, Shapiro M J, Ishihara H, Coughlin S R, J. Clin. Invest. 1999, 103, 879-887). A further thrombin receptor with possible significance for the pathophysiology of thrombotic processes, PAR-4, was identified on human and animal platelets. In experimental thromboses in animals having a PAR expression pattern comparable to humans, PAR-1 antagonists reduce the formation of platelet-rich thrombi (Derian C K, Damiano B P, Addo M F, Darrow A L, D'Andrea M R, Nedelman M, Zhang H-C, Maryanoff B E, Andrade-Gordon P, J. Pharmacol. Exp. Ther. 2003, 304, 855-861).

In the last few years, a large number of substances have been examined for their platelet function-inhibiting action; but only a few platelet function inhibitors have been found to be useful in practice. There is therefore a need for pharmaceuticals which specifically inhibit an increased platelet reaction without significantly increasing the risk of bleeding, thus reducing the risk of thromboembolic complications.

Effects of thrombin which are mediated via the PAR-1 receptor influence the progression of the disease during and after coronary artery bypass graft (CABG) and other operations, and in particular operations with extracorporeal circulation (for example heart-lung machine). During the course of the operation, there may be bleeding complications owing to pre- or intraoperative medication with coagulation-inhibiting and/or platelet-inhibiting substances. For this reason, for example, medication with clopidogrel has to be interrupted several days prior to a CABG. Moreover, as mentioned, disseminated intravascular coagulation or consumption coagulopathy (DIC) may develop (for example owing to the extended contact between blood and synthetic surfaces during extracorporeal circulation or blood transfusions), which in turn can lead to bleeding complications. At a later stage, there is frequently restenosis of the venous or arterial bypasses grafted (which may even result in occlusion) owing to thrombosis, intimafibrosis, arteriosclerosis, angina pectoris, myocardial infarction, heart failure, arrhythmias, transitory ischaemic attack (TIA) and/or stroke.

In man, the PAR-1 receptor is also expressed in other cells including, for example, endothelial cells, smooth muscle cells and tumour cells. Malignant tumour disorders (cancer) have a high incidence and are generally associated with high mortality. Current treatments achieve full remission in only a fraction of patients and are typically associated with severe side effects. There is therefore a high demand for more effective and safer therapies. The PAR-1 receptor contributes to cancer generation, growth, invasiveness and metastasis. Moreover, PAR-1 expressed on endothelial cells mediates signals resulting in vascular growth ("angiogenesis"), a process which is vital for enabling tumour growth beyond about 1 mm$^3$ Angiogenesis also contributes to the genesis or worsening of other disorders including, for example, haematopoetic cancer disorders, macular degeneration, which leads to blindness, and diabetic retinopathy, inflammatory disorders, such as rheumatoid arthritis and colitis.

Sepsis (or septicaemia) is a common disorder with high mortality. Initial symptoms of sepsis are typically unspecific (for example fever, reduced general state of health); however, during further progression there may be generalized activation of the coagulation system ("disseminated intravascular coagulation" or "consumption coagulopathy" (DIC)) with the formation of microthrombi in various organs and secondary bleeding complications. DIC may also occur independently of sepsis, for example during operations or associated with tumour disorders.

Treatment of sepsis consists firstly in the rigorous elimination of the infectious cause, for example by operative focal reconstruction and antibiosis. Secondly, it consists in temporary intensive medical support of the affected organ systems. Treatments of the different stages of this disease have been described, for example, in the following publication (Dellinger et al., Crit. Care Med. 2004, 32, 858-873). There are no proven effective treatments for DIC.

It is therefore an object of the present invention to provide novel PAR-1 antagonists for the treatment of disorders, for example cardiovascular disorders and thromboembolic disorders, and also tumour disorders in humans and animals.

WO 2006/012226, WO 2006/020598, WO 2007/038138, WO 2007/130898, WO 2007/101270 and US 2006/0004049 describe structurally similar piperidines as 11-β HSD1 inhibitors for treatment of, inter alia, diabetes, thromboembolic disorders and stroke.

The invention provides compounds of the formula

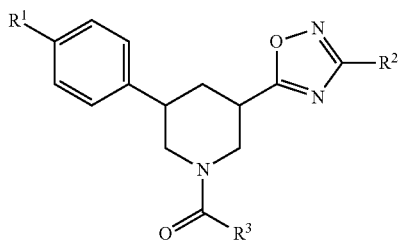

(I)

in which
R¹ is trifluoromethyl, 1,1-difluoroethyl, 2,2-difluoroethyl, 2,2,2-trifluoroethyl, difluoromethoxy, trifluoromethoxy or ethyl,
R² is 2-hydroxyeth-1-yl, 2-methoxyeth-1-yl, 2-ethoxyeth-1-yl, cyclopropyl or 1-methoxycycloprop-1-yl,
R³ is a group of the formula

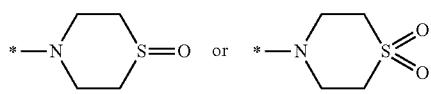

where
\* is the point of attachment to the carbonyl group,
and their salts, their solvates and the solvates of their salts.

Inventive compounds are the compounds of the formula (I) and their salts, solvates and solvates of the salts; the compounds, encompassed by formula (I), of the formulae mentioned below and their salts, solvates and solvates of the salts, and the compounds encompassed by the formula (I), cited below as working examples, and their salts, solvates and solvates of the salts if the compounds, encompassed by the formula (I), cited below are not already salts, solvates and solvates of the salts.

Depending on their structure, the inventive compounds may exist in stereoisomeric forms (enantiomers, diastereomers). Accordingly, the invention encompasses the enantiomers or diastereomers and their respective mixtures. From such mixtures of enantiomers and/or diastereomers, it is possible to isolate the stereoisomerically uniform constituents in a known manner.

If the inventive compounds can occur in tautomeric forms, the present invention encompasses all tautomeric forms.

In the context of the present invention, preferred salts are physiologically acceptable salts of the inventive compounds. Also encompassed, however, are salts which for their part are not suitable for pharmaceutical applications, but which can be used, for example, for isolating or purifying the inventive compounds.

Physiologically acceptable salts of the inventive compounds include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the inventive compounds also include salts of customary bases, such as, by way of example and with preference, alkali metal salts (for example sodium salts and potassium salts), alkaline earth metal salts (for example calcium salts and magnesium salts) and ammonium salts, derived from ammonia or organic amines having 1 to 16 carbon atoms, such as, by way of example and with preference, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine, N-methylpiperidine and choline.

In the context of the invention, solvates refer to those forms of the inventive compounds which, in solid or liquid state, form a complex by coordination with solvent molecules. Hydrates are a specific form of the solvates in which the coordination is with water.

Moreover, the present invention also encompasses prodrugs of the inventive compounds. The term "prodrugs" includes compounds which for their part may be biologically active or inactive but which, during the time they spend in the body, are converted to inventive compounds (for example metabolically or hydrolytically).

In the formula of the group which may be R³, the end point of the line marked by \* does not represent a carbon atom or a CH₂ group, but is part of the bond to the atom to which R³ is attached.

Preference is given to compounds of the formula (I) in which
R¹ is trifluoromethyl, 1,1-difluoroethyl, 2,2-difluoroethyl, 2,2,2-trifluoroethyl, difluoromethoxy, trifluoromethoxy or ethyl,
R² is 2-methoxyeth-1-yl, cyclopropyl or 1-methoxycycloprop-1-yl,
R³ is a group of the formula

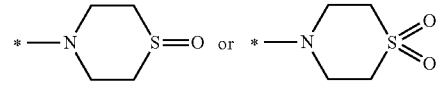

where
\* is the point of attachment to the carbonyl group,
and their salts, their solvates and the solvates of their salts.

Preference is also given to compounds of the formula (I) in which
R¹ is trifluoromethyl, 2,2,2-trifluoroethyl, trifluoromethoxy or ethyl,
R² is 2-methoxyeth-1-yl, cyclopropyl or 1-methoxycycloprop-1-yl,
R³ is a group of the formula

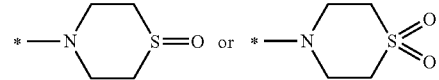

where
\* is the point of attachment to the carbonyl group,
and their salts, their solvates and the solvates of their salts.

Preference is also given to compounds of the formula (I) in which
R¹ is trifluoromethyl, 2,2,2-trifluoroethyl or trifluoromethoxy,
R² is cyclopropyl or 1-methoxycycloprop-1-yl,
R³ is a group of the formula

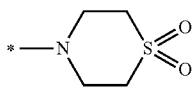

where
* is the point of attachment to the carbonyl group,
and their salts, their solvates and the solvates of their salts.

Preference is also given to compounds of the formula (I) in which
R¹ is trifluoromethyl, trifluoromethoxy or ethyl,
R² für 2-hydroxyeth-1-yl, 2-methoxyeth-1-yl, 2-ethoxyeth-1-yl or cyclopropyl,
R³ is a group of the formula

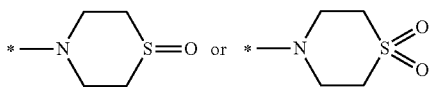

where
* is the point of attachment to the carbonyl group,
and their salts, their solvates and the solvates of their salts.

Preference is also given to compounds of the formula (I) in which
R¹ is trifluoromethyl or ethyl,
R² is 2-hydroxyeth-1-yl, 2-methoxyeth-1-yl or cyclopropyl,
R³ is a group of the formula

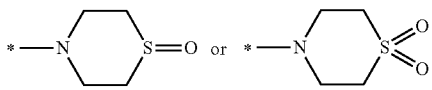

where
* is the point of attachment to the carbonyl group,
and their salts, their solvates and the solvates of their salts.

Preference is also given to compounds of the formula (I) in which
R¹ is trifluoromethyl or ethyl,
R² is 2-methoxyeth-1-yl,
R³ is a group of the formula

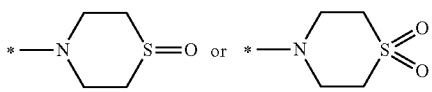

where
* is the point of attachment to the carbonyl group,
and their salts, their solvates and the solvates of their salts.

Preference is also given to compounds of the formula (I) in which
R¹ is trifluoromethyl or ethyl,
R² is 2-methoxyeth-1-yl,
R³ is a group of the formula

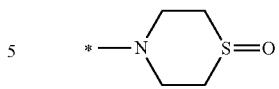

where
* is the point of attachment to the carbonyl group,
and their salts, their solvates and the solvates of their salts.

Preference is given to compounds of the formula (I) in which
R¹ is trifluoromethoxy,
R² is 2-methoxyeth-1-yl or cyclopropyl,
R³ is a group of the formula

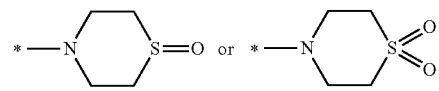

where
* is the point of attachment to the carbonyl group,
and their salts, their solvates and the solvates of their salts.

Preference is given to compounds of the formula (I) in which
R¹ is trifluoromethoxy,
R² is cyclopropyl,
R³ is a group of the formula

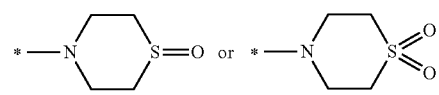

where
* is the point of attachment to the carbonyl group,
and their salts, their solvates and the solvates of their salts.

Preference is given to compounds of the formula (I) in which
R¹ is trifluoromethoxy,
R² is 2-methoxyeth-1-yl or cyclopropyl,
R³ is a group of the formula

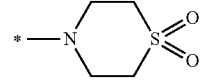

where
* is the point of attachment to the carbonyl group,
and their salts, their solvates and the solvates of their salts.

Preference is also given to compounds of the formula (I) in which the phenyl substituent and 1,2,4-oxadiazol-5-yl substituent, which are bonded to the piperidine ring, are in cis positions to one another.

Preference is also given to compounds of the formula (I) in which the carbon atom to which the phenyl substituent is bonded has S configuration and the carbon atom to which the 1,2,4-oxadiazol-5-yl substituent is bonded likewise has S configuration.

Preference is also given to compounds of the formula (I) in which R¹ is trifluoromethyl.

Preference is also given to compounds of the formula (I) in which R¹ is trifluoromethoxy.

Preference is also given to compounds of the formula (I) in which R¹ is ethyl.

Preference is also given to compounds of the formula (I) in which R² is 2-methoxyeth-1-yl.

Preference is also given to compounds of the formula (I) in which R² is cyclopropyl.

Preference is also given to compounds of the formula (I) in which R² is 1-methoxycycloprop-1-yl.

Preference is also given to compounds of the formula (I) in which
R³ is a group of the formula

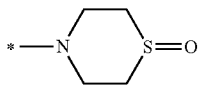

where
* is the point of attachment to the carbonyl group.

Preference is also given to compounds of the formula (I) in which
R³ is a group of the formula

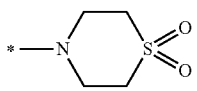

where
* is the point of attachment to the carbonyl group.

The individual radical definitions specified in the respective combinations or preferred combinations of radicals are, independently of the respective combinations of the radicals specified, also replaced as desired by radical definitions of other combinations.

Very particular preference is given to combinations of two or more of the preferred ranges mentioned above.

The invention further provides a process for preparing the compounds of the formula (I), or their salts, their solvates or the solvates of their salts, wherein
[A] compounds of the formula

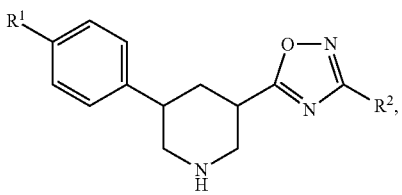

(II)

in which
R¹ and R² are each as defined above
are reacted with compounds of the formula

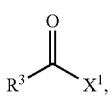

(III)

in which
R³ is as defined above and

X¹ is halogen, preferably bromine or chlorine, or hydroxyl or 4-nitrophenoxy, or

[B] compounds of the formula (II) are reacted in the first stage with 4-nitrophenyl chloroformate and in the second stage with compounds of the formula

 (IV)

R³—H in which
R³ is as defined above, or

[C] compounds of the formula

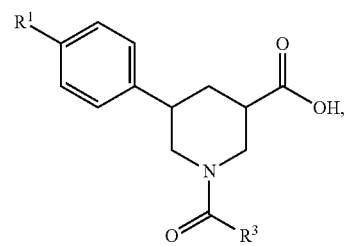

(V)

in which
R¹ and R³ are each as defined above
are reacted with compounds of the formula

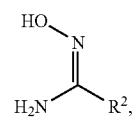

(VI)

in which
R² is as defined above, or

[D] compounds of the formula

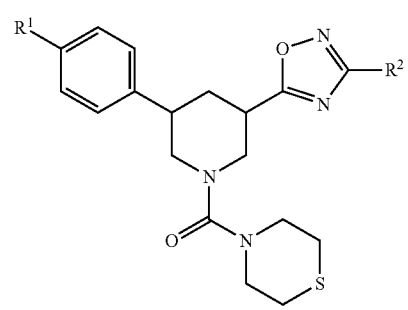

(Ia)

in which
R¹ and R² are each as defined above
are reacted with 0.8 to 1.1 equivalents of meta-chloroperbenzoic acid to give compounds of the formula

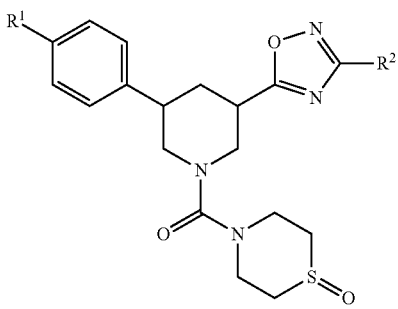

(Ib)

in which
R¹ and R² are each as defined above
or
[E] compounds of the formula (Ia) are reacted with 2.0 to 3.0 equivalents of meta-chloroperbenzoic acid to give compounds of the formula

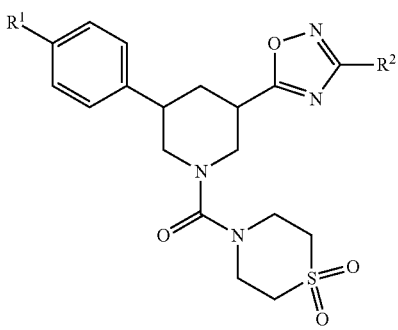

(Ic)

in which
R¹ and R² are each as defined above.

The compounds of the formulae (Ia), (Ib) and (Ic) are a subset of the compounds of the formula (I).

When $X^1$ is halogen, the reaction according to method [A] is generally effected in inert solvents, optionally in the presence of a base, preferably in a temperature range of −30° C. to 50° C. at standard pressure.

Inert solvents are, for example, tetrahydrofuran, methylene chloride, pyridine, dioxane or dimethylformamide, preference being given to methylene chloride.

Bases are, for example, triethylamine, diisopropylethylamine or N-methylmorpholine, preference being given to triethylamine or diisopropylethylamine When $X^1$ is hydroxyl, the reaction according to method [A] is generally effected in inert solvents, in the presence of a dehydrating reagent, optionally in the presence of a base, preferably in a temperature range of −30° C. to 50° C. at standard pressure.

Inert solvents are, for example, halohydrocarbons such as dichloromethane or trichloromethane, hydrocarbons such as benzene, nitromethane, dioxane, dimethylformamide or acetonitrile. It is equally possible to use mixtures of the solvents. Particular preference is given to dichloromethane or dimethylformamide Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylamino-isopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxy-carbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxy-benzotriazole (HOBt), or benzotriazol-1-yloxytris(dimethylamino)phosphonium hexa-fluorophosphate (BOP), or N-hydroxysuccinimide, or mixtures of these, with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethyl-aminopyridine or diisopropylethylamine.

Preferably, the condensation is effected with HATU or with EDC in the presence of HOBt.

When $X^1$ is 4-nitrophenoxy, the reaction according to method [A] is generally effected in inert solvents, optionally in the presence of a base, optionally in a microwave, preferably in a temperature range of 50° C. to 200° C. at standard pressure to 5 bar.

Inert solvents are, for example, N-methylpyrrolidone, dioxane or dimethylformamide, preference being given to N-methylpyrrolidone.

Bases are, for example, triethylamine, diisopropylethylamine or N-methylmorpholine, preference being given to triethylamine or diisopropylethylamine The compounds of the formula (III) are known or can be synthesized by known processes from the appropriate starting compounds.

The reaction of the first stage according to method [B] is generally effected in inert solvents, in the presence of a base, preferably in a temperature range of 0° C. to 50° C. at standard pressure.

Inert solvents are, for example, halohydrocarbons such as methylene chloride, trichloromethane, carbon tetrachloride or 1,2-dichloroethane, preference being given to methylene chloride.

Bases are, for example, organic bases such as trialkylamines, for example triethylamine, N-methyl-morpholine, N-methylpiperidine, 4-dimethylaminopyridine or diisopropylethylamine, preference being given to triethylamine.

The reaction of the second stage according to method [B] is generally effected in inert solvents, in the presence of a base, optionally in a microwave, preferably in a temperature range of 50° C. to 200° C. at standard pressure to 5 bar.

Inert solvents are, for example, dimethyl sulphoxide, dimethylformamide or N-methylpyrrolidone, preference being given to dimethylformamide Bases are, for example, alkali metal carbonates, for example sodium carbonate or potassium carbonate, preference being given to potassium carbonate.

The compounds of the formula (IV) are known or can be synthesized by known processes from the appropriate starting compounds.

The reaction according to method [C] is generally effected in inert solvents, in the presence of a dehydrating reagent, optionally in the presence of a base, preferably in a temperature range from room temperature up to reflux of the solvents at standard pressure.

Inert solvents are, for example, halohydrocarbons such as methylene chloride, trichloromethane or 1,2-dichloroethane, ethers such as dioxane, tetrahydrofuran or 1,2-dimethoxyethane, or other solvents such as acetone, dimethylformamide, dimethylacetamide, 2-butanone or acetonitrile. It is equally possible to use mixtures of the solvents. Preference is given to dimethylformamide or a mixture of dioxane and dimethylformamide.

Suitable dehydrating reagents in this context are, for example, carbodiimides, for example N,N'-diethyl-, N,N'-dipropyl-, N,N'-diisopropyl-, N,N'-dicyclohexylcarbodiimide, N-(3-dimethylamino-isopropyl)-N'-ethylcarbodiimide hydrochloride (EDC), N-cyclohexylcarbodiimide-N'-propyloxymethylpolystyrene (PS-carbodiimide), or carbonyl compounds such as carbonyldiimidazole, or 1,2-oxazolium compounds such as 2-ethyl-5-phenyl-1,2-oxazolium 3-sulphate or 2-tert-butyl-5-methylisoxazolium perchlorate, or acylamino compounds such as 2-ethoxy-1-ethoxy-carbonyl-1,2-dihydroquinoline, or propanephosphonic anhydride, or isobutyl chloroformate, or bis-(2-oxo-3-oxazolidinyl)phosphoryl chloride or benzotriazolyloxytri(dimethylamino) phosphonium hexafluorophosphate, or O-(benzotriazol-1-yl)-N,N,N',N'-tetramethyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), or 1-hydroxy-benzotriazole (HOBt), or benzotriazol-1-yloxytris(dimethylamino)phosphonium hexa-fluorophosphate (BOP), or benzotriazol-1-yloxytris(pyrrolidino) phosphonium hexafluorophosphate (PYBOP), or N-hydroxysuccinimide, or mixtures of these with bases.

Bases are, for example, alkali metal carbonates, for example sodium carbonate or potassium carbonate, or sodium hydrogencarbonate or potassium hydrogencarbonate, or organic bases such as trialkylamines, for example triethylamine, N-methylmorpholine, N-methylpiperidine, 4-dimethyl-aminopyridine or diisopropylethylamine, preference being given to diisopropylethylamine.

Preferably, the condensation is carried out with HATU in the presence of diisopropylethylamine or alternatively only with carbonyldiimidazole.

The compounds of the formula (VI) are known or can be synthesized by known processes from the appropriate starting compounds.

The reaction according to method [D] is generally performed in inert solvents, preferably in a temperature range from room temperature up to reflux of the solvents at standard pressure.

meta-Chloroperbenzoic acid is preferably used in an amount of 0.9 to 1.0 equivalent.

Inert solvents are, for example, halohydrocarbons such as methylene chloride, trichloromethane or 1,2-dichloroethane. Preference is given to methylene chloride.

The reaction according to method [E] is generally effected in inert solvents, preferably in a temperature range from room temperature up to reflux of the solvents at standard pressure.

meta-Chloroperbenzoic acid is preferably used in an amount of 2.3 to 2.6 equivalents, more preferably in an amount of 2.5 equivalents.

Inert solvents are, for example, halohydrocarbons such as methylene chloride, trichloromethane or 1,2-dichloroethane. Preference is given to methylene chloride.

The compounds of the formula (II) are known or can be prepared by reacting compounds of the formula

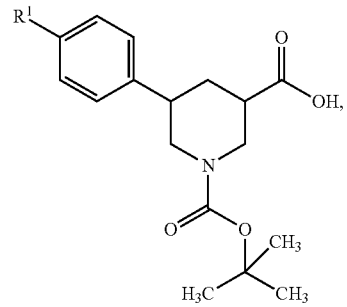

(VII)

in which
$R^1$ is as defined above
in the first stage with compounds of the formula (VI) and in the second stage with an acid.

The first stage reaction is effected as described for process [C]

The second stage reaction is generally effected in inert solvents, preferably in a temperature range from room temperature to 60° C. at standard pressure.

Inert solvents are, for example, halohydrocarbons such as methylene chloride, trichloromethane, carbon tetrachloride or 1,2-dichloroethane, or ethers such as tetrahydrofuran or dioxane, preference being given to methylene chloride.

Bases are, for example, trifluoroacetic acid or hydrogen chloride in dioxane, preference being given to trifluoroacetic acid.

The compounds of the formula (VII) are known or can be prepared by reacting compounds of the formula

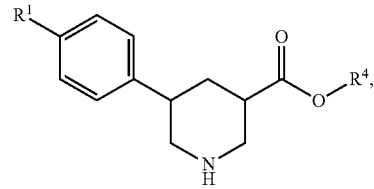

(VIII)

in which
$R^1$ is as defined above and
$R^4$ is methyl or ethyl,
in the first stage with di-tert-butyl dicarboxylate and in the second stage with a base.

The first stage reaction is generally effected in inert solvents, in the presence of a base, preferably in a temperature range from room temperature to 50° C. at standard pressure.

Inert solvents are, for example, halohydrocarbons such as methylene chloride, trichloromethane, carbon tetrachloride or 1,2-dichloroethane, preference being given to methylene chloride.

Bases are, for example, triethylamine, diisopropylethylamine or N-methylmorpholine, preference being given to triethylamine or diisopropylethylamine The second stage reaction is generally effected in inert solvents, in the presence of a base, preferably in a temperature range from room temperature up to reflux of the solvents at standard pressure.

Inert solvents are, for example, halohydrocarbons such as methylene chloride, trichloromethane, tetrachloromethane or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water, preference being given to methanol or methanol with one equivalent of water, or a mixture of tetrahydrofuran and water.

Bases are, for example, alkali metal hydroxides such as sodium, lithium or potassium hydroxide, or alkali metal carbonates such as caesium carbonate, sodium or potassium carbonate, or alkoxides such as potassium or sodium tert-butoxide, preference being given to lithium hydroxide or potassium tert-butoxide.

The compounds of the formula (VIII) are known or can be prepared by hydrogenating compounds of the formula

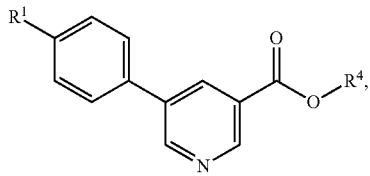

(IX)

in which
$R^1$ and $R^4$ are each as defined above.

The hydrogenation is generally effected with a reducing agent in inert solvents, optionally with addition of acid such as mineral acids and carboxylic acids, preferably acetic acid, preferably in a temperature range from room temperature up to reflux of the solvents and in a pressure range from standard pressure to 100 bar, preferably at standard pressure or at 50-80 bar.

A preferred reducing agent is hydrogen with palladium on activated carbon, with rhodium on activated carbon, with ruthenium on activated carbon or mixed catalysts thereof, or hydrogen with palladium on alumina or with rhodium on alumina, or hydrogen with palladium on activated carbon and platinum(IV) oxide, preference being given to hydrogen with palladium on activated carbon or with rhodium on activated carbon or hydrogen with palladium on activated carbon and platinum(IV) oxide. It is also possible to hydrogenate under pressure with hydrogen and platinum(IV) oxide alone.

Inert solvents are, for example, alcohols such as methanol, ethanol, n-propanol, isopropanol, n-butanol or tert-butanol, or concentrated acetic acid or methanol with addition of concentrated hydrochloric acid, preference being given to methanol or ethanol or concentrated acetic acid or methanol with addition of concentrated hydrochloric acid.

The compounds of the formula (IX) are known or can be prepared by reacting compounds of the formula

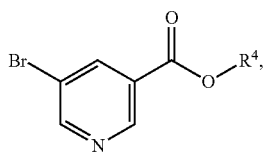

(X)

in which
$R^4$ is as defined above
with compounds of the formula

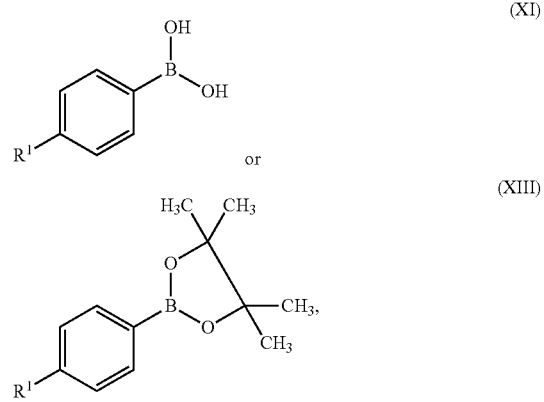

in which
$R^1$ is as defined above.

The reaction is generally effected in inert solvents, in the presence of a catalyst, if appropriate in the presence of an additional reagent, preferably in a temperature range from room temperature up to reflux of the solvent at standard pressure.

Inert solvents are, for example, ethers such as dioxane, tetrahydrofuran or 1,2-dimethoxyethane, hydrocarbons such as benzene, xylene or toluene, or other solvents such as nitrobenzene, dimethylformamide, dimethylacetamide, dimethyl sulphoxide or N-methylpyrrolidone; if appropriate, some water is added to these solvents. Preference is given to toluene with water or to a mixture of 1,2-dimethoxyethane, dimethylformamide and water.

Catalysts are, for example, palladium catalysts customary for Suzuki reaction conditions, preference being given to catalysts such as dichlorobis(triphenylphosphine)palladium, tetrakistriphenylphosphinepalladium(0), palladium(II) acetate or bis(diphenylphosphineferrocenyl)-palladium(II) chloride, for example.

Additional reagents are, for example, potassium acetate, caesium, potassium or sodium carbonate, barium hydroxide, potassium tert-butoxide, caesium fluoride, potassium fluoride or potassium phosphate, or mixtures thereof, preference being given to potassium fluoride or sodium carbonate, or a mixture of potassium fluoride and potassium carbonate.

The compounds of the formulae (X), (XI) and (XIII) are known or can be synthesized by known processes from the appropriate starting compounds.

The compounds of the formula (V) are known or can be prepared by reacting compounds of the formula

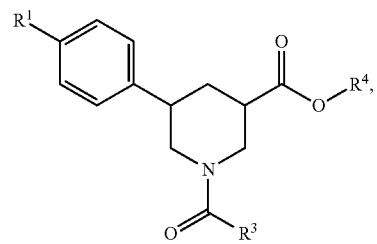

(XII)

in which
$R^1$ and $R^3$ are each as defined above and
$R^4$ is methyl or ethyl,
with a base.

The reaction is generally effected in inert solvents, in the presence of a base, preferably in a temperature range from room temperature up to reflux of the solvents at standard pressure.

Inert solvents are, for example, halohydrocarbons such as methylene chloride, trichloromethane, tetrachloromethane or 1,2-dichloroethane, alcohols such as methanol or ethanol, ethers such as diethyl ether, methyl tert-butyl ether, 1,2-dimethoxyethane, dioxane or tetrahydrofuran, or other solvents such as dimethylformamide, dimethylacetamide, acetonitrile or pyridine, or mixtures of solvents, or mixtures of solvent with water, preference being given to methanol or methanol with one equivalent of water, or a mixture of tetrahydrofuran and water.

Bases are, for example, alkali metal hydroxides such as sodium, lithium or potassium hydroxide, or alkali metal carbonates such as caesium carbonate, sodium or potassium carbonate, or alkoxides such as potassium or sodium tert-butoxide, preference being given to lithium hydroxide or potassium tert-butoxide.

The compounds of the formula (XII) are known or can be prepared by reacting compounds of the formula (VIII) with compounds of the formula (III).

The reaction is effected as described for method [A].

In an alternative method, the compounds of the formula (XII) can be prepared by reacting compounds of the formula (VIII) in the first stage with 4-nitrophenyl chloroformate and in the second stage with compounds of the formula (IV).

The reaction is effected as described for method [B].

The preparation of the compounds of the formula (I) can be illustrated by the synthesis scheme below.

The inventive compounds have an unforeseeable, valuable spectrum of pharmacological and pharmacokinetic activity. They are selective antagonists of the PAR-1 receptor acting in particular as platelet aggregation inhibitors, as inhibitors of endothelial cell activation, as inhibitors of smooth muscle cell proliferation and as inhibitors of tumour growth. For some of the diseases mentioned, for example cardiovascular diseases with high thromboembolic risk, permanent protection by PAR-1 antagonism with simultaneously simple management of medication is of great significance. The PAR-1 antagonists of the present invention exhibit long-lasting action after single oral administration, i.e. an action which lasts at least 16 hours.

Accordingly, they are suitable for use as medicaments for treatment and/or prophylaxis of diseases in man and animals.

The present invention further provides for the use of the inventive compounds for treatment and/or prophylaxis of disorders, preferably of thromboembolic disorders and/or thromboembolic complications.

"Thromboembolic disorders" in the context of the present invention include in particular disorders such as ST-segment elevation myocardial infarction (STEMI) and non-ST-segment elevation myocardial infarction (non-STEMI), stable angina pectoris, unstable angina pectoris, reocclusions and restenoses after coronary interventions such as angioplasty, stent implantations or aortocoronary bypass, peripheral arterial occlusion diseases, pulmonary embolisms, deep venous thromboses and renal vein thromboses, transitory ischaemic attacks and also thrombotic and thromboembolic stroke.

The substances are therefore also suitable for prevention and treatment of cardiogenic thromboembolisms, for Scheme:

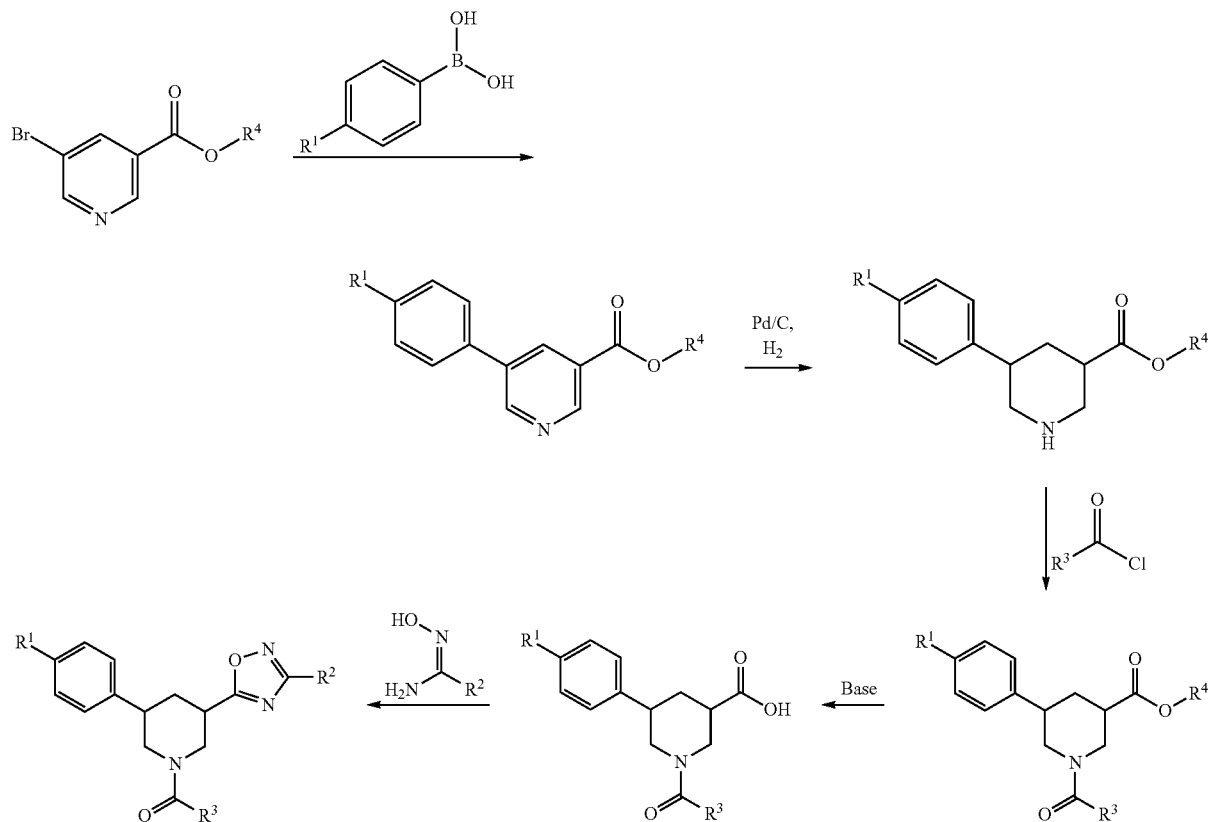

example brain ischaemias, stroke and systemic thromboembolisms and ischaemias, in patients with acute, intermittent or persistent cardiac arrhythmias, for example atrial fibrillation, and those undergoing cardioversion, and also in patients with heart valve disorders or with intravasal objects, for example artificial heart valves, catheters, intraaortic balloon counterpulsation and pacemaker probes.

Thromboembolic complications are also encountered in connection with microangiopathic haemolytic anaemias, extracorporeal circulation, for example haemodialysis, haemofiltration, ventricular assist devices and artifical hearts, and also heart valve prostheses.

Moreover, the inventive compounds are also used for influencing wound healing, for the prophylaxis and/or treatment of atherosclerotic vascular disorders and inflammatory disorders such as rheumatic disorders of the locomotive system, coronary heart diseases, of heart failure, of hypertension, of inflammatory disorders, for example asthma, COPD, inflammatory pulmonary disorders, glomerulonephritis and inflammatory intestinal disorders, and additionally also for the prophylaxis and/or treatment of Alzheimer's disease, autoimmune disorders, Crohn's disease and ulcerative colitis.

Moreover, the inventive compounds can be used for inhibiting tumour growth and the formation of metastases, for microangiopathies, age-related macular degeneration, diabetic retinopathy, diabetic nephropathy and other microvascular disorders, and also for the prevention and treatment of thromboembolic complications, for example venous thromboembolisms, for tumour patients, in particular those undergoing major surgical interventions or chemo- or radiotherapy.

The inventive compounds are additionally suitable for treatment of cancer. Cancers include: carcinomas (including breast cancer, hepatocellular carcinomas, lung cancer, colorectal cancer, cancer of the colon and melanomas), lymphomas (for example non-Hodgkin's lymphomas and mycosis fungoides), leukaemias, sarcomas, mesotheliomas, brain cancer (for example gliomas), germinomas (for example testicular cancer and ovarian cancer), choriocarcinomas, renal cancer, cancer of the pancreas, thyroid cancer, head and neck cancer, endometrial cancer, cervical cancer, bladder cancer, stomach cancer and multiple myeloma.

Moreover, PAR-1 expressed on endothelial cells mediates signals resulting in vascular growth ("angiogenesis"), a process which is vital for enabling tumour growth beyond about 1 $mm^3$. Induction of angiogenesis is also relevant for other disorders; these include disorders of the rheumatic type (for example rheumatoid arthritis), pulmonary disorders (for example pulmonary fibrosis, pulmonary hypertension, in particular pulmonary arterial hypertension, disorders characterized by pulmonary occlusion), arteriosclerosis, plaque rupture, diabetic retinopathy and wet macular degeneration.

In addition, the inventive compounds are suitable for treatment of sepsis. Sepsis (or septicaemia) is a common disorder with high mortality. Initial symptoms of sepsis are typically unspecific (for example fever, reduced general state of health); however, during further progression there may be a general activation of the coagulation system ("disseminated intravascular coagulation" or "consumption coagulopathy"; referred to hereinafter as "DIC") with the formation of microthrombi in various organs and secondary bleeding complications. Moreover, there may be endothelial damage with increased permeability of the vessels and diffusion of fluid and proteins into the extravasal space. Later, there may be organ dysfunction or organ failure (for example kidney failure, liver failure, respiratory failure, deficits of the central nervous system and heart/circulatory failure) and even multiple organ failure. In principle, this may affect any organ; the most frequently encountered organ dysfunctions and organ failures are those of the lung, the kidney, the cardiovascular system, the coagulation system, the central nervous system, the endocrine glands and the liver. Sepsis may be associated with an "acute respiratory distress syndrome" (referred to hereinafter as ARDS). ARDS may also occur independently of sepsis. "Septic shock" refers to the occurence of hypotension, which requires treatment, and promotes further organ damage and is associated with a worsening of the prognosis.

Pathogens may be bacteria (gram-negative and gram-positive), fungi, viruses and/or eukaryotes. The site of entry or primary infection may be pneumonia, an infection of the urinary tract or peritonitis, for example. The infection may, but need not necessarily, be associated with bacteriaemia.

Sepsis is defined as the presence of an infection and a "systemic inflammatory response syndrome" (referred to hereinafter as "SIRS"). SIRS occurs during infections, but also during other states such as injuries, burns, shock, operations, ischaemia, pancreatitis, reanimation or tumours. The definition of the ACCP/SCCM Consensus Conference Committee of 1992 (*Crit. Care Med.* 1992, 20, 864-874) describes the symptoms required for the diagnosis "SIRS" and measurement parameters (inter alia a change in body temperature, increased heart rate, breathing difficulties and altered blood profile). The later (2001) SCCM/ESICM/ACCP/ATS/SIS International Sepsis Definitions Conference essentially maintained the criteria, but fine-tuned details (Levy et al., *Crit. Care Med.* 2003, 31, 1250-1256).

DIC and SIRS may occur during sepsis, but also as a result of operations, tumour disorders, burns or other injuries. In the case of DIC, there is a massive activation of the coagulation system at the surface of damaged endothelial cells, the surfaces of foreign bodies or injured extravascular tissue. As a consequence, there is coagulation in small vessels of various organs with hypoxia and subsequent organ dysfunction. A secondary effect is the consumption of coagulation factors (for example factor X, prothrombin, fibrinogen) and platelets, which reduces the coagulability of the blood and may result in heavy bleeding.

In addition, the inventive compounds can also be used for preventing coagulation ex vivo, for example for preserving blood and plasma products, for cleaning/pretreating catheters and other medical auxiliaries and instruments, including extracorporeal circulation, for coating synthetic surfaces of medical auxiliaries and instruments used in vivo or ex vivo or for platelet-containing biological samples.

The present invention further provides for the use of the inventive compounds for coating medical instruments and implants, for example catheters, prostheses, stents or artificial heart valves. In this case, the inventive compounds can be firmly attached to the surface or, for local action, be released over a certain period of time from a carrier coating into the immediate environment.

The present invention further provides for the use of the inventive compounds for treatment and/or prophylaxis of disorders, in particular the disorders mentioned above.

The present invention further provides for the use of the inventive compounds for producing a medicament for treatment and/or prophylaxis of disorders, in particular the disorders mentioned above.

The present invention further provides a method for treatment and/or prophylaxis of disorders, in particular the disorders mentioned above, using a therapeutically effective amount of an inventive compound.

The present invention further provides medicaments comprising an inventive compound and one or more further active ingredients, in particular for treatment and/or prophylaxis of the disorders mentioned above. Active ingredients suitable for combinations are, by way of example and with preference:

calcium channel blockers, for example amlodipine besilate (for example Norvase), felodipine, diltiazem, verapamil, nifedipine, nicardipine, nisoldipine and bepridil;

iomerizine;

statins, for example atorvastatin, fluvastatin, lovastatin, pitavastatin, pravastatin, rosuvastatin and simvastatin;

cholesterol resorption inhibitors, for example ezetimibe and AZD4121;

cholesteryl ester transfer protein ("CETP") inhibitors, for example torcetrapib;

low molecular weight heparins, for example dalteparin sodium, ardeparin, certoparin, enoxaparin, parnaparin, tinzaparin, reviparin and nadroparin;

further anticoagulants, for example warfarin, marcumar, fondaparinux;

antiarrhythmics, for example dofetilide, ibutilide, metoprolol, metoprolol tartrate, propranolol, atenolol, ajmaline, disopyramide, prajmaline, procainamide, quinidine, sparteine, aprindine, lidocaine, mexiletine, tocamide, encamide, flecamide, lorcamide, moricizine, propafenone, acebutolol, pindolol, amiodarone, bretylium tosylate, bunaftine, sotalol, adenosine, atropine and digoxin;

alpha-adrenergic agonists, for example doxazosin mesylate, terazoson and prazosin; beta-adrenergic blockers, for example carvedilol, propranolol, timolol, nadolol, atenolol, metoprolol, bisoprolol, nebivolol, betaxolol, acebutolol and bisoprolol;

aldosterone antagonists, for example eplerenone and spironolactone;

angiotensin-converting enzyme inhibitors ("ACE inhibitors"), for example moexipril, quinapril hydrochloride, ramipril, lisinopril, benazepril hydrochloride, enalapril, captopril, spirapril, perindopril, fosinopril and trandolapril;

angiotensin II receptor blockers ("ARBs"), for example olmesartan-medoxomil, candesartan, valsartan, telmisartan, irbesartan, losartan and eprosartan;

endothelin antagonists, for example tezosentan, bosentan and sitaxsentan-sodium;

inhibitors of neutral endopeptidase, for example candoxatril and ecadotril;

phosphodiesterase inhibitors, for example milrinone, theophylline, vinpocetine, EHNA (erythro-9-(2-hydroxy-3-nonyl)adenine), sildenafil, vardenafil and tadalafil;

fibrinolytics, for example reteplase, alteplase and tenecteplase;

GP IIb/IIIa antagonists, for example integrillin, abciximab and tirofiban;

direct thrombin inhibitors, for example AZD0837, argatroban, bivalirudin and dabigatran;

indirect thrombin inhibitors, for example odiparcil;

direct and indirect factor Xa inhibitors, for example fondaparinux-sodium, apixaban, razaxaban, rivaroxaban (BAY 59-7939), KFA-1982, DX-9065a, AVE3247, otamixaban (XRP0673), AVE6324, SAR377142, idraparinux, SSR126517, DB-772d, DT-831j, YM-150, 813893, LY517717 and DU-1766;

direct and indirect factor Xa/IIa inhibitors, for example enoxaparin-sodium, AVE5026, SSR128428, SSR128429 and BIBT-986 (Tanogitran);

lipoprotein-associated phospholipase A2 ("LpPLA2") modulators;

diuretics, for example chlorthalidone, ethacrynic acid, furosemide, amiloride, chlorothiazide, hydrochlorothiazide, methylclothiazide and benzthiazide;

nitrates, for example isosorbide 5-mononitrate;

thromboxane antagonists, for example seratrodast, picotamide and ramatroban;

platelet aggregation inhibitors, for example clopidogrel, tiklopidin, cilostazol, aspirin, abciximab, limaprost, eptifibatide and CT-50547;

cyclooxygenase inhibitors, for example meloxicam, rofecoxib and celecoxib;

B-type natriuretic peptides, for example nesiritide and ularitide;

NV1FGF modulators, for example XRP0038;

HT1B/5-HT2A antagonists, for example SL65.0472;

guanylate cyclase activators, for example ataciguat (HMR1766), HMR1069, riociguat and cinaciguat;

e-NOS transcription enhancers, for example AVE9488 and AVE3085;

antiatherogenic substances, for example AGI-1067:

sCPU inhibitors, for example AZD9684;

renin inhibitors, for example aliskirin and VNP489;

inhibitors of adenosine diphosphate-induced platelet aggregation, for example clopidogrel, ticlopidine, prasugrel, AZD6140, ticagrelor and elinogrel;

NHE-1 inhibitors, for example AVE4454 and AVE4890.

Antibiotic therapy: various antibiotics or antifungal medicament combinations are suitable, either as calculated therapy (before a microbial assessment has been made) or as specific therapy; fluid therapy, for example crystalloid or colloidal fluids; vasopressors, for example norepinephrine, dopamine or vasopressin; inotropic therapy, for example dobutamine; corticosteroids, for example hydrocortisone, or fludrocortisone; recombinant human activated protein C, Xigris; blood products, for example erythrocyte concentrates, platelet concentrates, erythropoietin or fresh frozen plasma; assisted ventilation in sepsis-induced acute lung injury (ALI) or acute respiratory distress syndrome (ARDS), for example permissive hypercapnia, low tidal volumes; sedation: for example diazepam, lorazepam, midazolam or propofol. Opioids: for example fentanyl, hydromorphone, morphine, meperidine or remifentanil. NSAIDs: for example ketorolac, ibuprofen or acetaminophen. Neuromuscular blockade: for example pancuronium; glucose control, for example insulin, glucose; renal replacement therapies, for example continuous veno-venous haemofiltration or intermittent haemodialysis. Low-dose dopamine for renal protection; anticoagulants, for example for thrombosis prophylaxis or for renal replacement therapies, for example unfractionated heparins, low molecular weight heparins, heparinoids, hirudin, bivalirudin or argatroban; bicarbonate therapy; stress ulcer prophylaxis, for example H2 receptor inhibitors, antacids.

Medicaments for proliferative disorders: uracil, chlormethine, cyclophosphamide, ifosfamide, melphalan, chlorambucil, pipobroman, triethylenemelamine, triethylenethiophosphoramine, busulfan, carmustine, lomustine, streptozocin, dacarbazine, methotrexate, 5-fluorouracil, floxuridine, cytarabine, 6-mercaptopurine, 6-thioguanine, fludarabine phosphate, pentostatin, vinblastine, vincristine, vindesine, bleomycin, dactinomycin, daunorubicin, doxorubicin, epirubicin, idarubicin, paclitaxel, mithramycin, deoxycoformycin, mitomycin-C, L-asparaginase, interferons, etoposide, teniposide, 17.alpha.-ethynylestradiol, diethylstilbestrol, testosterone, prednisone, fluoxymesterone, dromostanolone propionate, testolactone, megestrol acetate, tamoxifen, methylprednisolone, methyltestosterone, prednisolone, triamcinolone, chlorotrianisene, hydroxyprogesterone, aminoglutethimide, estranrustine, medroxyprogesterone acetate, leuprolide, flutamide, toremifene, goserelin, cisplatin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, oxaliplatin (Eloxatie), Iressa (gefmitib, Zd1839), XELODA® (capecitabine), Tarceva® (erlotinib), Azacitidine (5-azacytidine; 5-AzaC), temozolomide (Temodar®), gemcitabine (e.g. GEMZAR® (gemcitabine HCl)), vasostatin or a combination of two or more of the above.

The present invention further provides a method for preventing the coagulation of blood in vitro, in particular in banked blood or biological samples containing platelets, which is characterized in that an anticoagulatory amount of the inventive compound is added.

The inventive compounds can act systemically and/or locally. For this purpose, they can be administered in a suitable way, for example by the oral, parenteral, pulmonal, nasal, sublingual, lingual, buccal, rectal, dermal, transdermal, conjunctival, otic route, or as implant or stent.

The inventive compounds can be administered in administration forms suitable for these administration routes.

Suitable administration forms for oral administration are those which function according to the prior art and deliver the inventive compounds rapidly and/or in modified fashion, and which contain the inventive compounds in crystalline and/or amorphized and/or dissolved form, for example tablets (uncoated or coated tablets, for example having enteric coatings or coatings which are insoluble or dissolve with a delay and control the release of the inventive compound), tablets which disintegrate rapidly in the mouth, or films/wafers, films/lyophilizates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration include preparations for injection and infusion in the form of solutions, suspensions, emulsions, lyophilizates or sterile powders.

Oral administration is preferred.

Suitable for the other administration routes are, for example, pharmaceutical forms for inhalation (inter alia powder inhalers, nebulizers), nasal drops, solutions or sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (e.g. patches), milk, pastes, foams, dusting powders, implants or stents.

The inventive compounds can be converted to the administration forms mentioned. This can be done in a manner known per se by mixing with inert, nontoxic, pharmaceutically suitable excipients. These excipients include carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants for example ascorbic acid), colours (e.g. inorganic pigments for example iron oxides) and masking flavours and/or odours.

The present invention further provides medicaments comprising at least one inventive compound, preferably together with one or more inert nontoxic pharmaceutically suitable auxiliaries, and their use for the purposes mentioned above.

In the case of parenteral administration, it has generally been found to be advantageous to administer amounts of about 5 to 250 mg every 24 hours to achieve effective results. In the case of oral administration the amount is about 5 to 100 mg every 24 hours.

It may nevertheless be necessary where appropriate to deviate from the stated amounts, in particular as a function of the body weight, route of administration, individual response to the active ingredient, nature of the preparation and time or interval over which administration takes place.

The percentages in the tests and examples which follow are, unless indicated otherwise, percentages by weight; parts are parts by weight. Solvent ratios, dilution ratios and concentration data for the liquid/liquid solutions are each based on volume, "w/v" means "weight/volume". For example, "10% w/v" means: 100 ml of solution or suspension comprise 10 g of substance.

A) EXAMPLES

Abbreviations:

| | |
|---|---|
| approx. | approximately |
| CDI | carbonyldiimidazole |
| d | day(s), doublet (in NMR) |
| TLC | thin-layer chromatography |
| DCI | direct chemical ionization (in MS) |
| dd | double doublet (in NMR) |
| DMAP | 4-dimethylaminopyridine |
| DMF | N,N-dimethylformamide |
| DMSO | dimethyl sulphoxide |
| DPPA | diphenyl phosphorazidate |
| DSC | disuccinimidyl carbonate |
| eq. | equivalent(s) |
| ESI | electrospray ionization (in MS) |
| h | hour(s) |
| HATU | O-(7-azabenzotriazol-1-yl)-N,N,N',N'-tetramethyluronium hexafluorophosphate |
| HPLC | high-pressure, high-performance liquid chromatography |
| LC-MS | liquid chromatography-coupled mass spectroscopy |
| LDA | lithium diisopropylamide |
| m | multiplet (in NMR) |
| min | minute(s) |
| MS | mass spectroscopy |
| NMR | nuclear magnetic resonance spectroscopy |
| PYBOP | benzotriazol-1-yloxytris(pyrrolidino)phosphonium hexafluorophosphate |
| q | quartet (in NMR) |
| RP | reversed phase (in HPLC) |
| RT | room temperature |
| $R_t$ | retention time (in HPLC) |
| s | singlet (in NMR) |
| t | triplet (in NMR) |
| THF | tetrahydrofuran |

HPLC Methods:

Method 1A: Instrument: HP 1100 with DAD detection; column: Kromasil 100 RP-18, 60 mm×2.1 mm, 3.5 µm; eluent A: 5 ml of perchloric acid (70%)/l of water, eluent B: acetonitrile; gradient: 0 min 2% B→0.5 min 2% B→4.5 min 90% B→6.5 min 90% B→6.7 min 2% B→7.5 min 2% B; flow rate: 0.75 ml/min; column temperature: 30° C.; UV detection: 210 nm.

LC-MS Methods:

Method 1B: MS instrument type: Micromass ZQ; HPLC instrument type: HP 1100 Series; UV DAD; column: Phenomenex Gemini 3µ, 30 mm×3.0 mm; eluent A: 1 l of water+0.5 ml of 50% formic acid, eluent B: 1 l of acetonitrile+0.5 ml of 50% formic acid; gradient: 0.0 min 90% A→2.5 min 30% A→3.0 min 5% A→4.5 min 5% A; flow rate: 0.0 min 1 ml/min, 2.5 min/3.0 min/4.5 min 2 ml/min; oven: 50° C.; UV detection: 210 nm.

Method 2B: Instrument: Micromass QuattroPremier with Waters HPLC Acquity; column: Thermo Hypersil GOLD 1.9μ, 50 mm×1 mm; eluent A: 1 l of water+0.5 ml of 50% formic acid, eluent B: 1 l of acetonitrile+0.5 ml of 50% formic acid; gradient: 0.0 min 90% A→0.1 min 90% A→1.5 min 10%A→2.2 min 10%A; oven: 50° C.; flow rate: 0.33 ml/min; UV detection: 210 nm.

Method 3B: MS instrument type: Micromass ZQ; HPLC instrument type: Waters Alliance 2795; column: Phenomenex Synergi 2.5μ MAX-RP 100A Mercury, 20 mm×4 mm; eluent A: 1 l of water+0.5 ml of 50% formic acid, eluent B: 1 l of acetonitrile+0.5 ml of 50% formic acid; gradient: 0.0 min 90% A→0.1 min 90% A→3.0 min 5% A→4.0 min 5% A→4.01 min 90% A; flow rate: 2 ml/min; oven: 50° C.; UV detection: 210 nm.

Method 4B: Instrument: Micromass Quattro Micro MS with HPLC Agilent series 1100; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10%A→4.01 min 100%A→5.00 min 100%A; oven: 50° C.; flow rate: 2 ml/min; UV detection: 210 nm.

Method 5B: Instrument: Waters ACQUITY SQD HPLC System; column: Waters Acquity HPLC HSS T3 1.8μ 50 mm×1 mm; eluent A: 1 l of water+0.25 ml of 99% formic acid, eluent B: 1 l of acetonitrile+0.25 ml of 99% formic acid; gradient: 0.0 min 90% A→1.2 min 5% A→2.0 min 5% A; oven: 50° C.; flow rate: 0.40 ml/min; UV detection: 210-400 nm.

Method 6B: MS instrument type: Waters (Micromass) Quattro Micro; HPLC instrument type: Agilent 1100 series; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A→4.01 min 100% A; (flow rate: 2.5 ml/min)→5.00 min 100% A; oven: 50° C.; flow rate: 2 ml/min; UV detection: 210 nm.

Method 7B: MS instrument type: Waters ZQ; HPLC instrument type: Agilent 1100 Series; UV DAD; column: Thermo Hypersil GOLD 3μ 20 mm×4 mm; eluent A: 1 l of water+0.5 ml of 50% formic acid, eluent B: 1 l of acetonitrile+0.5 ml of 50% formic acid; gradient: 0.0 min 100% A→3.0 min 10% A→4.0 min 10% A oven: 55° C.; flow rate: 2 ml/min; UV detection: 210 nm.

Preparative Separation of Enantiomers:

Method 1D: Phase: Daicel Chiralpak AD-H, 5 μm 250 mm×20 mm, eluent: isohexane/isopropanol 25:75; flow rate: 15 ml/min, temperature: 45° C.; UV detection: 220 nm.

Method 2D: Phase: Daicel Chiralpak IA, 5 μm 250 mm×20 mm, eluent: methanol/acetonitrile 25:75; flow rate: 15 ml/min, temperature: 30° C.; UV detection: 220 nm.

Method 3D: Phase: Daicel Chiralpak IA, 5 μm 250 mm×20 mm, eluent: methanol/acetonitrile 50:50; flow rate: 15 ml/min, temperature: 30° C.; UV detection: 220 nm.

Method 4D: Phase: Daicel Chiralpak IA, 5 μm 250 mm×20 mm, eluent: tert-butyl methyl ether/methanol 50:50; flow rate: 15 ml/min; temperature: 30° C.; UV detection: 220 nm.

Method 5D: Phase: Daicel Chiralpak IA, 5 μm 250 mm×20 mm, eluent: methanol/acetonitrile 25:75; flow rate: 15 ml/min, temperature: 30° C.; UV detection: 220 nm.

Method 6D: Phase: Daicel Chiralpak AD-H, 5 μm 250 mm×20 mm, eluent: isohexane/ethanol 25:75; flow rate: 15 ml/min, temperature: 45° C.; UV detection: 220 nm.

Method 7D: Phase: Daicel Chiralpak AD-H, 5 μm 250 mm×20 mm, eluent: ethanol 100%; flow rate: 15 ml/min, temperature: 45° C.; UV detection: 220 nm.

Method 8D: Phase: Daicel Chiralpak AD-H, 5 μm 250 mm×20 mm, eluent: isohexane/isopropanol 30:70; flow rate: 15 ml/min, temperature: 45° C.; UV detection: 220 nm.

Method 9D: Phase: Daicel Chiralpak IA, 5 μm 250 mm×20 mm, eluent: acetonitrile/methanol 70:30; flow rate: 15 ml/min, temperature: 30° C.; UV detection: 220 nm.

Method 10D: Phase: Daicel Chiralpak IA, 5 μm 250 mm×20 mm, eluent: acetonitrile/methanol 70:30; flow rate: 20 ml/min, temperature: 35° C.; UV detection: 210 nm.

Method 11D: Phase: Daicel Chiralpak AD-H, 5 μm 250 mm×20 mm, eluent: isohexane/ethanol 70:30; flow rate: 15 ml/min, temperature: 40° C.; UV detection: 220 nm.

Analytical Separation of Enantiomers:

Method 1E: Phase: Daicel Chiralpak AD-H, 5 μm 250 mm×4 mm; eluent: isopropanol/isohexane: 75:25; flow rate: 1 ml/min; temperature: 45° C.; UV detection: 220 nm.

Method 2E: Phase: Daicel Chiralpak AD-H, 5 μm 250 mm×4.6 mm; eluent: isohexane/isopropanol 25:75+0.2% trifluoroacetic acid+1% water; flow rate: 1 ml/min; temperature: 45° C.; UV detection: 235 nm.

Method 3E: Phase: Daicel Chiralpak IA, 5 μm 250 mm×4.6 mm, eluent: acetonitrile/methanol 75:25; flow rate: 1 ml/min; temperature: 25° C.; UV detection: 220 nm.

Method 4E: Phase: Daicel Chiralpak IA, 5 μm 250 mm×4.6 mm, eluent: acetonitrile/methanol 50:50; flow rate: 1 ml/min; temperature: 25° C.; UV detection: 220 nm.

Method 5E: Phase: Daicel Chiralpak IA, 5 μm 250 mm×4.6 mm, eluent: tert-butyl methyl ether/methanol 50:50; flow rate: 1 ml/min; temperature: 25° C.; UV detection: 220 nm.

Method 6E: Phase: Daicel Chiralpak AD-H, 5 μm 250 mm×4.6 mm, eluent: ethanol 100%; flow rate: 1 ml/min, temperature: 45° C.; UV detection: 220 nm.

Method 7E: Phase: Daicel Chiralpak AD-H, 5 μm 250 mm×4.6 mm, eluent: isohexane/isopropanol 30:70; flow rate: 1 ml/min; temperature: 45° C.; UV detection: 220 nm.

Method 8E: Phase: Daicel Chiralpak IA, 5 μm 250 mm×4.6 mm, eluent: acetonitrile/methanol 70:30; flow rate: 15 ml/min, temperature: 25° C.; UV detection: 220 nm.

Method 9E: Phase: Daicel Chiralpak IA, 5 μm 250 mm×4.6 mm, eluent: acetonitrile/methanol 70:30; flow rate: 15 ml/min, temperature: 30° C.; UV detection: 220 nm.

Method 10E: Phase: Daicel Chiralpak IA, 5 μm 250 mm×4.6 mm, eluent: acetonitrile/methanol 70:30; flow rate: 1 ml/min, temperature: 30° C.; UV detection: 220 nm.

Method 11E: Phase: Daicel Chiralpak AD-H, 5 μm 250 mm×4.6 mm, eluent: isohexane/ethanol 25:75+0.2% trifluoroacetic acid+1% water; flow rate: 1 ml/min, temperature: 45° C.; UV detection: 220 nm.

GC-MS Methods:

Method 1F: Instrument: Micromass GCT, GC6890; column: Restek RTX-35, 15 m×200 μm×0.33 μm; constant flow rate with helium: 0.88 ml/min; oven: 70° C.; inlet: 250° C.; gradient: 70° C., 30° C./min→310° C. (hold for 3 min)

The microwave reactor used was a "single mode" instrument of the Emrys™ Optimizer type.

Starting Compounds

General Method 1A: N'-Hydroxyimidamide Formation

A solution of the appropriate nitrile (1.0 eq) in ethanol (1.2 ml/mmol) is admixed at RT with hydroxylammonium chloride (1.5 eq.) and triethylamine (1.2 eq.). The reaction mixture is stirred at room temperature overnight. For workup, the ethanol is removed under reduced pressure, saturated aqueous sodium hydrogencarbonate solution is added and the reaction mixture is extracted with ethyl acetate. The organic phase is dried over sodium sulphate and concentrated. The residue is reacted without further purification.

General Method 2A: N'-Hydroxyimidamide Formation

A solution of the appropriate nitrile (1.0 eq) in a mixture of ethanol (1.9 ml/mmol) and water (0.5 ml/mmol) is admixed at RT with hydroxylammonium chloride (1.08 eq.) and sodium hydroxide (1.12 eq.). The reaction mixture is stirred at room temperature for 16 hours. For workup, the reaction mixture is concentrated under reduced pressure, admixed with dichloromethane and filtered. The filtrate is concentrated under reduced pressure and the residue is reacted without further purification.

General Method 3A: Suzuki Coupling

A mixture of the appropriate bromopyridine in toluene (1.8 ml/mmol) is admixed under argon and at RT with tetrakis(triphenylphosphine)palladium (0.02 eq.), with a solution of the appropriate arylboronic acid (1.2 eq.) in ethanol (0.5 ml/mmol) and with a solution of potassium fluoride (2.0 eq.) in water (0.2 ml/mmol). The reaction mixture is stirred under reflux for several hours until the conversion is substantially complete. After addition of ethyl acetate and phase separation, the organic phase is washed once with water and once with saturated aqueous sodium chloride solution, dried (magnesium sulphate), filtered and concentrated under reduced pressure. The crude product is purified by flash chromatography (silica gel 60, eluent: dichloromethane/methanol mixtures).

General Method 4A: Hydrogenation of the Pyridine

A solution of the pyridine in ethanol (9 ml/mmol) is admixed under argon with palladium on activated carbon (moistened with approx. 50% water, 0.3 g/mmol), and the mixture is hydrogenated at 60° C. in a 50 bar hydrogen atmosphere overnight. The catalyst is then filtered off through a filter layer and washed repeatedly with ethanol. The combined filtrates are concentrated under reduced pressure.

General Method 5A: Methyl Ester Hydrolysis/Epimerization

At RT, potassium tert-butoxide (10 eq.) is added to a solution of the appropriate methyl ester (1.0 eq.) in methanol (35-40 ml/mmol). The mixture is stirred at 60° C. overnight. If the conversion is incomplete, water (1.0 eq.) is added and the mixture is stirred at 60° C. until the conversion is complete. For workup, the methanol is removed under reduced pressure, the residue is admixed with water and the mixture is acidified (pH 1) with aqueous 1 N hydrochloric acid solution. The mixture is extracted with ethyl acetate and the organic phase is dried with magnesium sulphate, filtered and concentrated under reduced pressure.

General Method 6A: Oxadiazole Formation

A solution of the appropriate piperidine-3-carboxylic acid in dimethylformamide (10-20 ml/mmol) is admixed under argon at RT with HATU (1.2 eq.), N,N-diisopropylethylamine (2.2 eq.) and the appropriate N-hydroxyimidamide (1.1 eq.). The reaction mixture is stirred at RT until the formation of the intermediate is complete and then stirred further at 120° C. until the desired product has formed from this intermediate. The reaction mixture is then purified by means of preparative HPLC.

Example 1A

N'-Hydroxy-3-methoxypropanimidamide

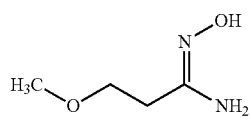

According to General Method 1A, 20.0 g (235.0 mmol) of 3-methoxypropionitrile were reacted. Yield: 18.1 g (49% of theory, purity 74%)

HPLC (Method 1A): $R_t$=0.35 min; MS (ESIpos): m/z=119 [M+H]$^+$.

Example 2A

3-Ethoxy-N'-hydroxypropanimidamide

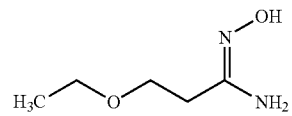

According to General Method 2A, 5.0 g (50.4 mmol) of 3-ethoxypropionitrile were reacted. Yield: 0.6 g (8% of theory, purity 90%)

HPLC (Method 1A): $R_t$=0.60 min; MS (ESIpos): m/z=133 [M+H]$^+$.

Example 3A

N'-Hydroxycyclopropanecarboximidamide

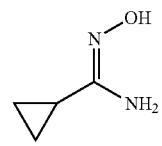

According to General Method 2A, 7.2 g (107.3 mmol) of cyclopropanecarbonitrile were reacted. Yield: 4.8 g (44% of theory)

LC-MS (Method 2B): $R_t$=0.16 min; MS (ESIpos): m/z=101 [M+H]$^+$.

Example 4A

Methyl 5-(4-ethylphenyl)pyridine-3-carboxylate

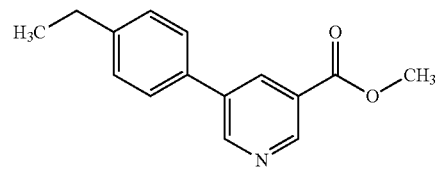 [SMILES: CCc1ccc(-c2cncc(C(=O)OC)c2)cc1]

According to General Method 3A, 32 g (148 mmol) of methyl 5-bromonicotinate and 27 g (178 mmol, 1.2 eq.) of 4-ethylphenylboronic acid were reacted. Yield: 24 g (64% of theory)

LC-MS (Method 3B): $R_t$=2.03 min; MS (ESIpos): m/z=242 [M+H]$^+$.

$^1$H NMR (400 MHz, DMSO-d$_6$): δ=9.13 (d, 1H), 9.05 (d, 1H), 8.45 (t, 1H), 7.72 (d, 2H), 7.38 (d, 2H), 3.93 (s, 3H), 2.68 (q, 2H), 1.22 (t, 3H).

Example 5A

Methyl 5-(4-ethylphenyl)piperidine-3-carboxylate [racemic cis/trans isomer mixture]

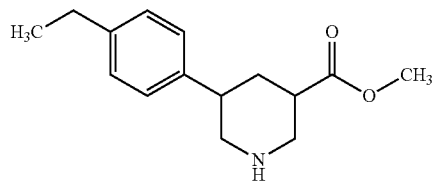 [SMILES: CCc1ccc(C2CNCC(C(=O)OC)C2)cc1]

According to General Method 4A, 24 g (94 mmol) of methyl 5-(4-ethylphenyl)pyridine-3-carboxylate were hydrogenated. Yield: 20 g (77% of theory)

LC-MS (Method 4B): $R_t$=1.43 min; MS (ESIpos): m/z=248 [M+H]$^+$.

Example 6A

Methyl 5-(4-ethylphenyl)-1-(thiomorpholin-4-ylcarbonyl)piperidine-3-carboxylate [racemic cis/trans isomer mixture]

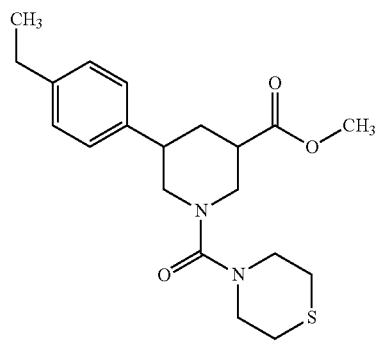 [SMILES: CCc1ccc(C2CC(C(=O)OC)CN(C(=O)N3CCSCC3)C2)cc1]

5.00 g (12.1 mmol) of 3-methyl 1-(4-nitrophenyl) 5-(4-ethylphenyl)piperidine-1,3-dicarboxylate (Example 30A), 3.57 g (36.4 mmol) of thiomorpholine and 5.03 g (36.4 mmol) of potassium carbonate were added to 76 ml of DMF and heated in 5 portions at 150° C. for 1.5 h in a single-mode microwave (Emrys Optimizer). For workup, the reaction solutions were combined and filtered, and the residue was purified by means of preparative HPLC. Yield: 3.07 g (67% of theory)

LC-MS (Method 5B): $R_t$=1.16 and 1.18 min (cis/trans isomers); MS (ESIpos): m/z=377 [M+H]$^+$.

Example 7A 5-(4-Ethylphenyl)-1-(thiomorpholin-4-ylcarbonyl)piperidine-3-carboxylic acid [racemic cis isomer]

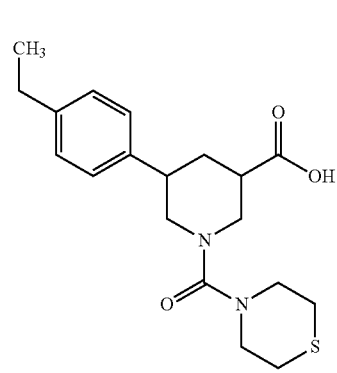 [SMILES: CCc1ccc(C2CC(C(=O)O)CN(C(=O)N3CCSCC3)C2)cc1]

According to General Method 5A, 3.00 g (7.97 mmol) of the compound from Example 6A and 8.94 g (79.7 mmol) of potassium tert-butoxide were reacted. The reaction led selectively to the cis isomer. Yield: 2.74 g (93% of theory)

LC-MS (Method 5B): $R_t$=1.04 min; MS (ESIpos): m/z=363 [M+H]$^+$.

Example 8A

{3-(4-Ethylphenyl)-5-[3-(2-methoxyethyl)-1,2,4-oxadiazol-5-yl]piperidin-1-yl}(thiomorpholin-4-yl)methanone [racemic cis isomer]

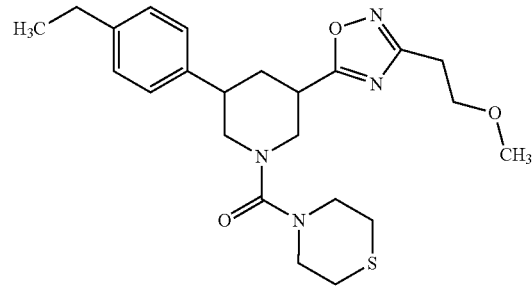 [SMILES: CCc1ccc(C2CC(c3nc(CCOC)no3)CN(C(=O)N3CCSCC3)C2)cc1]

According to General Method 6A, 300 mg (0.828 mmol) of the compound from Example 7A and 134 mg (0.910 mmol) of N-hydroxy-3-methoxypropanimidamide were reacted Yield: 185 mg (49% of theory)

LC-MS (Method 5B): $R_t$=1.22 min; MS (ESIpos): m/z=445 [M+H]$^+$.

Example 9A

[3-(3-Cyclopropyl-1,2,4-oxadiazol-5-yl)-5-(4-ethylphenyl)piperidin-1-yl](thiomorpholin-4-yl)-methanone [racemic cis isomer]

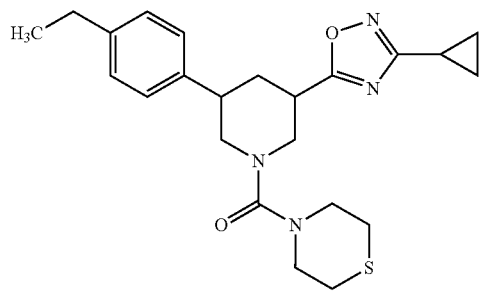 [SMILES: CCc1ccc(C2CC(c3nc(C4CC4)no3)CN(C(=O)N3CCSCC3)C2)cc1]

According to General Method 6A, 300 mg (0.828 mmol) of the compound from Example 7A and 91 mg (0.91 mmol) of N-hydroxycyclopropanecarboximidamide were reacted Yield: 141 mg (40% of theory)

LC-MS (Method 5B): $R_t$=1.32 min; MS (ESIpos): m/z=427 [M+H]$^+$.

$^1$H NMR (400 MHz, DMSO-d$_6$): δ=7.22 (d, 2H), 7.15 (d, 2H), 3.92 (d, 1H), 3.52 (d, 1H), 3.44 (br. s., 4H), 3.38-3.31 (m, 1H), 3.03-2.79 (m, 3H), 2.63-2.55 (m, 6H), 2.25 (d, 1H), 2.10 (td, 1H), 1.91 (q, 1H), 1.16 (t, 3H), 1.09-1.01 (m, 2H), 0.92-0.85 (m, 2H).

Example 10A

{3-(4-Ethylphenyl)-5-[3-(2-hydroxyethyl)-1,2,4-oxadiazol-5-yl]piperidin-1-yl}(thiomorpholin-4-yl)methanone [racemic cis isomer]

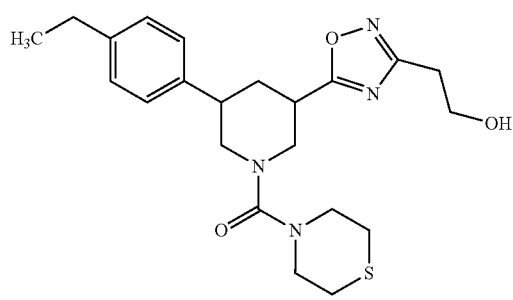 [SMILES: CCc1ccc(C2CC(c3nc(CCO)no3)CN(C(=O)N3CCSCC3)C2)cc1]

According to General Method 6A, 300 mg (0.828 mmol) of the compound from Example 7A and 112 mg (1.08 mmol) of N',3-dihydroxypropanimidamide [Graham A. Showell et al., J. Med. Chem., 1991, 34, 1086-1094] were reacted. Yield: 248 mg (66% of theory)

LC-MS (Method 5B): $R_t$=2.22 min; MS (ESIpos): m/z=431 [M+H]$^+$.

Example 11A

{3-[3-(2-Ethoxyethyl)-1,2,4-oxadiazol-5-yl]-5-(4-ethylphenyl)piperidin-1-yl}(thiomorpholin-4-yl)methanone [racemic cisisomer]

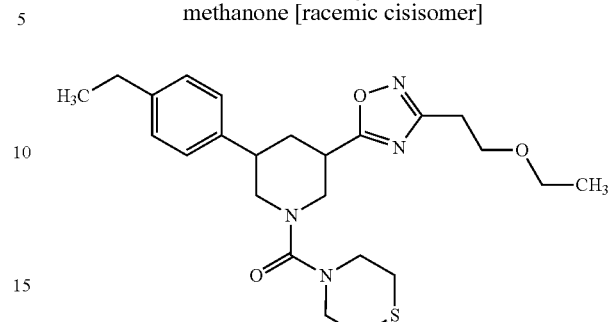

According to General Method 6A, 600 mg (1.655 mmol) of the compound from Example 7A and 355 mg (approx. 2.152 mmol) of 3-Ethoxy-N-hydroxypropanimidamide were reacted Yield: 389 mg (49% of theory)

LC-MS (Method 6B): $R_t$=2.61 min; MS (ESIpos): m/z=459 [M+H]$^+$.

$^1$H NMR (400 MHz, DMSO-d$_6$): δ=7.23 (d, 2H), 7.16 (d, 2H), 3.95 (d, 1H), 3.71 (t, 2H), 3.54 (d, 1H), 3.48-3.34 (m, 7H), 3.08-2.81 (m, 5H), 2.63-2.55 (m, 6H), 2.29 (d, 1H), 1.95 (q, 1H), 1.16 (t, 3H), 1.07 (t, 3H).

Example 12A

Methyl 5-[4-(trifluoromethyl)phenyl]pyridine-3-carboxylate

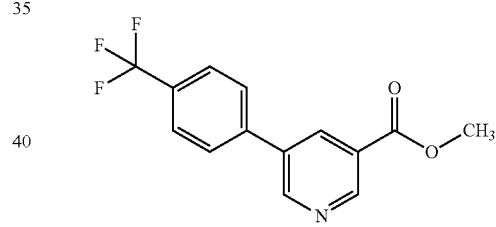

According to General Method 3A, 28 g (132 mmol) of methyl 5-bromonicotinate and 30 g (158 mmol, 1.2 eq.) of 4-trifluoromethylphenylboronic acid were reacted. Yield: 32 g (85% of theory)

LC-MS (Method 4B): $R_t$=2.27 min; MS (ESIpos): m/z=282 [M+H]$^+$.

Example 13A

Methyl 5-[4-(trifluoromethyl)phenyl]piperidine-3-carboxylate [racemic cis/trans isomer mixture]

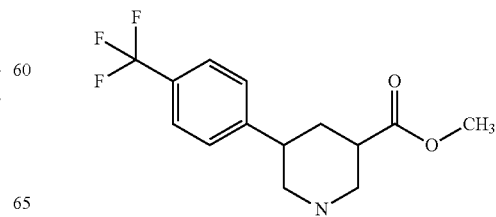

32 g (112 mmol) of methyl 5-[4-(trifluoromethyl)phenyl]pyridine-3-carboxylate (Example 12A) were hydrogenated according to General Method 4A. Yield: 26 g (82% of theory)

LC-MS (Method 1B): $R_t$=1.35 and 1.41 min (cis/trans isomers); MS (ESIpos): m/z=288 [M+H]$^+$.

$^1$H NMR (400 MHz, DMSO-$d_6$): δ=9.22 (d, 1H), 9.14 (d, 1H), 8.57 (t, 1H), 8.06 (d, 2H), 7.89 (d, 2H), 3.94 (s, 3H).

Example 14A

3-Methyl 1-(4-nitrophenyl) 5-[4-(trifluoromethyl)phenyl]piperidine-1,3-dicarboxylate [racemic cis/trans isomer mxture]

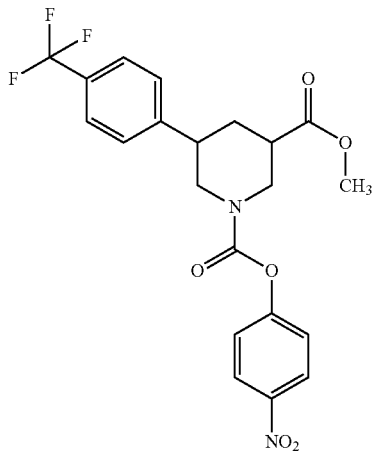 [SMILES: COC(=O)C1CC(c2ccc(C(F)(F)F)cc2)CN(C(=O)Oc2ccc([N+](=O)[O-])cc2)C1]

20.0 g (69.6 mmol) of methyl 5-[4-(trifluoromethyl)phenyl]piperidine-3-carboxylate (Example 13A) were dissolved in 1.0 l of dichloromethane, and admixed at 0° C. with 14.1 g (139 mmol) of triethylamine Subsequently, 14.0 g (69.6 mmol) of 4-nitrophenyl chlorocarbonate were added dropwise. The reaction mixture was stirred at 0° C. for 2 h and then at RT for 16 h. For workup, the mixture was washed with saturated aqueous sodium hydrogencarbonate solution. The organic phase was dried over magnesium sulphate, filtered and concentrated under reduced pressure. This gave 31.3 g of crude product, which was reacted without any further purification steps.

LC-MS (Method 3B): $R_t$=2.44 min and 2.48 min (cis/trans isomers); MS (ESIpos): m/z=453 [M+H]$^+$.

Example 15A

Methyl 1-(thiomorpholin-4-ylcarbonyl)-5-[4-(trifluoromethyl)phenyl]piperidine-3-carboxylate [racemic cis/trans isomer mixture]

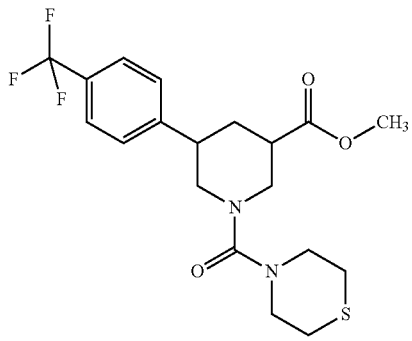 [SMILES: COC(=O)C1CC(c2ccc(C(F)(F)F)cc2)CN(C(=O)N2CCSCC2)C1]

10.0 g (22.1 mmol) of 3-methyl 1-(4-nitrophenyl)-5-[4-(trifluoromethyl)phenyl]piperidine-1,3-dicarboxylate, 6.84 g (66.3 mmol) of thiomorpholine and 9.17 g (66.3 mmol) of potassium carbonate were added to 150 ml of DMF and heated in 10 portions at 150° C. for 1 h in a single-mode microwave (Emrys Optimizer). For workup, the reaction solutions were combined and filtered, and the residue was purified by means of preparative HPLC. Yield: 5.16 g (55% of theory)

LC-MS (Method 5B): $R_t$=1.13 and 1.16 min (cis/trans isomers); MS (ESIpos): m/z=417 [M+H]$^+$.

Example 16A 1-(Thiomorpholin-4-ylcarbonyl)-5-[4-(trifluoromethyl)phenyl]piperidine-3-carboxylic acid [racemic cis isomer]

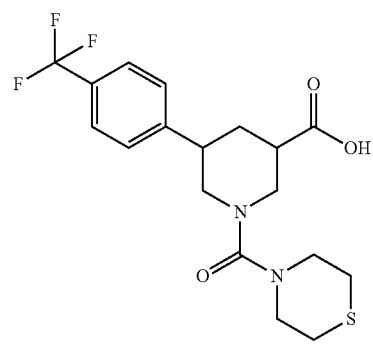 [SMILES: O=C(O)C1CC(c2ccc(C(F)(F)F)cc2)CN(C(=O)N2CCSCC2)C1]

According to General Method 5A, 5.16 g (12.4 mmol) of the compound from Example 15A and 13.9 g (124 mmol) of potassium tert-butoxide were reacted. The reaction led selectively to the cis isomer. Yield: 4.90 g (98% of theory)

LC-MS (Method 5B): $R_t$=1.04 min; MS (ESIpos): m/z=403 [M+H]$^+$.

Example 17A

{3-(3-Cyclopropyl-1,2,4-oxadiazol-5-yl)-5-[4-(trifluoromethyl)phenyl]piperidin-1-yl}-(thiomorpholin-4-yl)methanone [racemic cis isomer]

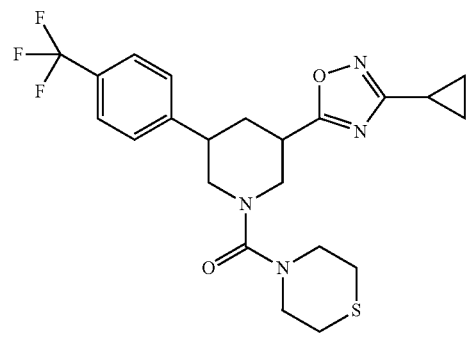 [SMILES: O=C(N1CCSCC1)N1CC(c2ccc(C(F)(F)F)cc2)CC(c2nc(C3CC3)no2)C1]

According to General Method 6A, 600 mg (1.491 mmol) of the compound from Example 16A and 164 mg (1.640 mmol) of N-hydroxycyclopropanecarboximidamide were reacted Yield: 352 mg (47% of theory)

LC-MS (Method 5B): $R_t$=1.28 min; MS (ESIpos): m/z=467 [M+H]$^+$.

$^1$H NMR (400 MHz, DMSO-$d_6$): δ=7.70 (d, 2H), 7.56 (d, 2H), 3.92 (d, 1H), 3.57 (d, 1H), 3.45 (br. s., 4H), 3.40-3.34 (m, 1H), 3.08-2.95 (m, 3H), 2.59 (br. s., 4H), 2.30 (d, 1H), 2.16-2.07 (m, 1H), 2.04-1.91 (m, 1H), 1.10-1.01 (m, 2H), 0.92-0.85 (m, 2H).

Example 18A

{3-[3-(2-Methoxyethyl)-1,2,4-oxadiazol-5-yl]-5-[4-(trifluoromethyl)phenyl]piperidin-1-yl}-(thiomorpholin-4-yl)methanone [racemic cis isomer]

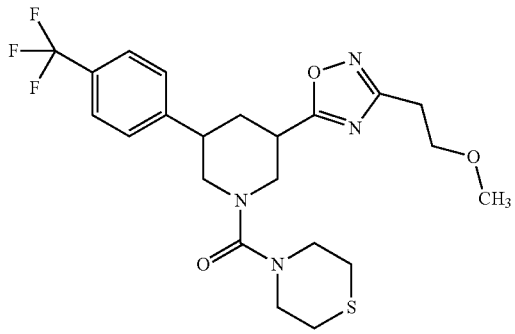 [SMILES: COCCc1noc(C2CC(c3ccc(C(F)(F)F)cc3)CN(C(=O)N3CCSCC3)C2)n1]

According to General Method 6A, 600 mg (1.491 mmol) of the compound from Example 16A and 242 mg (1.640 mmol) of N-hydroxy-3-methoxypropanimidamide were reacted Yield: 350 mg (46% of theory)

LC-MS (Method 5B): $R_t$=1.18 min; MS (ESIpos): m/z=485 [M+H]$^+$.

$^1$H NMR (400 MHz, DMSO-$d_6$): δ=7.70 (d, 2H), 7.57 (d, 2H), 3.95 (d, 1H), 3.68 (t, 2H), 3.58 (d, 1H), 3.51-3.36 (m, 5H), 3.23 (s, 3H), 3.13-2.96 (m, 3H), 2.94 (t, 2H), 2.60 (br. s., 4H), 2.33 (br. d., 1H), 2.10-1.95 (m, 1H).

Example 19A

{3-[3-(2-Ethoxyethyl)-1,2,4-oxadiazol-5-yl]-5-[4-(trifluoromethyl)phenyl]piperidin-1-yl}-(thiomorpholin-4-yl)methanone [racemic cis isomer]

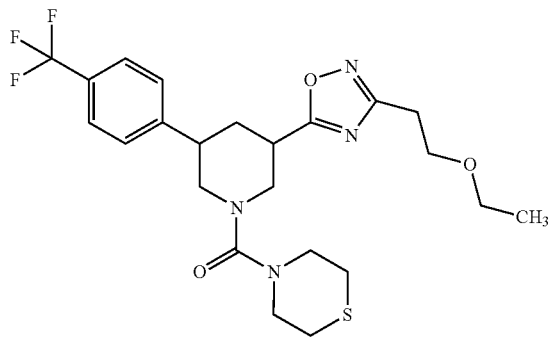 [SMILES: CCOCCc1noc(C2CC(c3ccc(C(F)(F)F)cc3)CN(C(=O)N3CCSCC3)C2)n1]

According to General Method 6A, 600 mg (1.491 mmol) of the compound from Example 16A and 320 mg (approx.1.983 mmol) of 3-ethoxy-N-hydroxypropanimidamide were reacted Yield: 343 mg (46% of theory)

LC-MS (Method 6B): $R_t$=2.57 min; MS (ESIpos): m/z=499 [M+H]$^+$.

$^1$H NMR (400 MHz, DMSO-$d_6$): δ=7.70 (d, 2H), 7.57 (d, 2H), 3.96 (d, 1H), 3.71 (t, 2H), 3.58 (d, 1H), 3.49-3.37 (m, 7H), 3.11-2.97 (m, 3H), 2.93 (t, 2H), 2.60 (br. s., 4H), 2.34 (br. d., 1H), 2.02 (q, 1H), 1.07 (t, 3H).

Example 20A

{3-[3-(2-Hydroxyethyl)-1,2,4-oxadiazol-5-yl]-5-[4-(trifluoromethyl)phenyl]piperidin-1-yl}-(thiomorpholin-4-yl)methanone [racemic cis isomer]

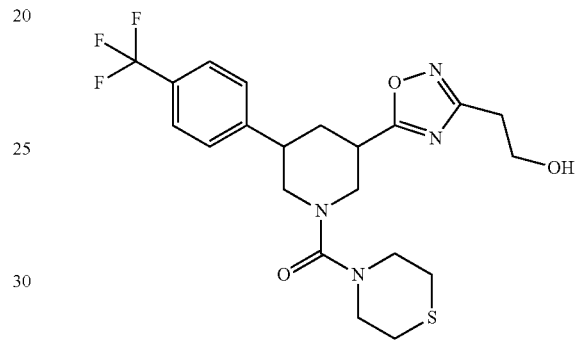

According to General Method 6A, 600 mg (1.491 mmol) of the compound from Example 16A and 201 mg (1.938 mmol) of N',3-dihydroxypropanimidamide were reacted Yield: 494 mg (68% of theory)

LC-MS (Method 5B): $R_t$=1.04 min; MS (ESIpos): m/z=471 [M+H]$^+$.

Example 21A

Methyl 5-[4-(trifluoromethoxy)phenyl]pyridine-3-carboxylate

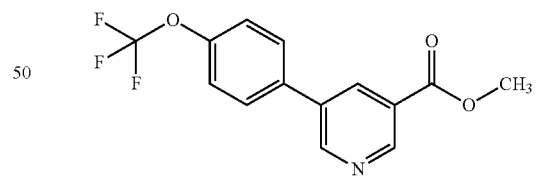

According to General Method 3A, 23 g (105 mmol) of methyl 5-bromonicotinate and 26 g (126 mmol, 1.2 eq.) of 4-trifluoromethoxyphenylboronic acid were reacted. Yield: 14 g (41% of theory)

LC-MS (Method 1B): $R_t$=2.44 min; MS (ESIpos): m/z=298 [M+H]$^+$.

Alternative Synthesis:

A solution of 26 g (121 mmol) of methyl 5-bromonicotinate in toluene (220 ml) was admixed under argon at RT with 2.8 g (2.4 mmol) of tetrakis(triphenylphosphine)palladium, and then a solution of 30 g (146 mmol) of 4-trifluoromethoxyphenylboronic acid in ethanol (58 ml) was added. After adding 14 g (243 mmol) of potassium fluoride in water (58 ml), the mixture was stirred under reflux overnight, a further 0.70 g (0.61 mmol) of tetrakis(triphenylphosphine)palladium was added, and the mixture was stirred under reflux for a further 24 h. After adding another 1.4 g (1.2 mmol) of tetrakis (triphenylphosphine)palladium, the mixture was stirred under reflux for 20 h, and the reaction solution was admixed with ethyl acetate and washed with water and saturated aqueous sodium chloride solution. The organic phase was dried over magnesium sulphate, filtered and concentrated under reduced pressure. The residue was purified by means of column chromatography (silica gel, cyclohexane/dichloromethane 1:1→dichloromethane). Yield: 31 g (86% of theory)

LC-MS (Method 4B): $R_t$=2.32 min; MS (ESIpos): m/z=298 [M+H]$^+$;

$^1$H NMR (400 MHz, DMSO-d$_6$): δ=9.17 (d, 1H), 9.10 (d, 1H), 8.51 (t, 1H), 7.95 (d, 2H), 7.52 (d, 2H), 3.94 (s, 3H).

Example 22A

Methyl 5-[4-(trifluoromethoxy)phenyl]piperidine-3-carboxylate [racemic cis/trans isomer mixture]

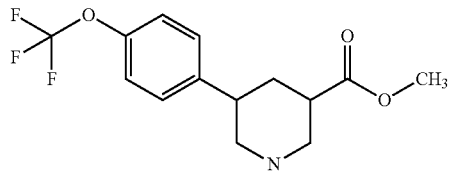 [SMILES: COC(=O)C1CNCC(c2ccc(OC(F)(F)F)cc2)C1]

14 g (45 mmol) of methyl 5-[4-(trifluoromethoxy)phenyl] pyridine-3-carboxylate in ethanol (500 ml) were admixed with 17 g of moistened palladium/carbon catalyst (10% palladium, 50% water), and then hydrogenated at 60° C. and a 50 bar hydrogen atmosphere overnight. The reaction solution was filtered, the filter residue was washed with ethanol and the filtrate was concentrated under reduced pressure. The residue was purified by means of column chromatography (silica gel, dichloromethane/methanol 600:1→10:1). Yield: 8 g (59% of theory)

LC-MS (Method 1B): $R_t$=1.29 min and 1.33 min (cis/trans isomers); MS (ESIpos): m/z=304 [M+H]$^+$;

$^1$H NMR (400 MHz, DMSO-d$_6$): δ=7.43-7.35 (m, 4H), 7.31-7.25 (m, 4H), 3.60 (s, 3H), 3.40-3.21 (m, 5H), 3.16 (d, 1H), 3.01-2.89 (m, 3H), 2.88-2.78 (m, 2H), 2.78-2.65 (m, 4H), 2.17 (d, 1H), 2.09 (d, 1H), 1.82 (td, 1H), 1.68 (q, 1H), approx. 1:1.3 mixture of the cis/trans isomers, two protons hidden.

Example 23A

3-Methyl 1-(4-nitrophenyl)-5-[4-(trifluoromethoxy) phenyl]piperidine-1,3-dicarboxylate [racemic cis/trans isomer mixture]

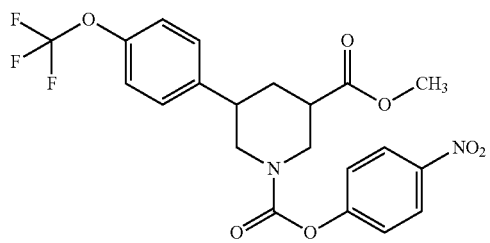 [SMILES: COC(=O)C1CC(c2ccc(OC(F)(F)F)cc2)CN(C(=O)Oc2ccc([N+](=O)[O-])cc2)C1]

At 0° C., 5.32 g (26.4 mmol) of 4-nitrophenyl chloroformate were added slowly to 8.0 g (26.4 mmol) of methyl 5-(4-(trifluoromethoxy)phenyl)piperidine-3-carboxylate (Example 22A) and 5.34 g (26.3 mmol) of triethylamine in 666 ml of dichloromethane. The mixture was stirred at RT for 2 h. For workup, the reaction mixture was washed first with saturated aqueous sodium hydrogencarbonate solution, then with water. The organic phase was dried over sodium sulphate and concentrated under reduced pressure. The residue was purified by means of flash chromatography on silica gel (eluent: cyclohexane/ethyl acetate 1:2->1:1). Yield: 7.32 g (54% of theory)

LC-MS (Method 3B): $R_t$=2.47 min; MS (ESIpos): m/z=469 [M+H]$^+$.

Example 24A

Methyl 1-(thiomorpholin-4-ylcarbonyl)-5-[4-(trifluoromethoxy)phenyl]piperidine-3-carboxylate [racemic cis/trans isomer mixture]

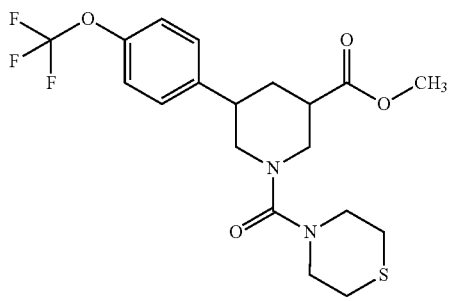 [SMILES: COC(=O)C1CC(c2ccc(OC(F)(F)F)cc2)CN(C(=O)N2CCSCC2)C1]

12.0 g (25.1 mmol) of 3-methyl 1-(4-nitrophenyl)-5-[4-(trifluoromethoxy)phenyl]piperidine-1,3-dicarboxylate, 7.77 g (75.3 mmol) of thiomorpholine and 10.4 g (75.3 mmol) of potassium carbonate were added to 180 ml of DMF and heated in 12 portions at 150° C. for 2 h in a single-mode microwave (Emrys Optimizer). For workup, the reaction solutions were combined and filtered, and the residue was purified by means of preparative HPLC. Yield: 7.88 g (73% of theory)

LC-MS (Method 5B): $R_t$=1.16 and 1.18 min (cis/trans isomers); MS (ESIpos): m/z=433 [M+H]$^+$.

$^1$H NMR (400 MHz, DMSO-d$_6$): δ=7.46-7.39 (m, 4H), 7.32 (d, 4H), 3.84 (dd, 2H), 3.64 (s, 3H), 3.63 (s, 3H), 3.55-3.34 (m, 10H), 3.09 (dd, 1H), 3.06-2.96 (m, 1H), 2.92-2.81 (m, 6H), 2.76-2.67 (m, 1H), 2.65-2.56 (m, 7H), 2.25-2.10 (m, 2H), 1.95-1.84 (m, 1H), 1.76 (q, 1H), approx. 1:1 mixture of the cis/trans isomers.

Example 25A 1-(Thiomorpholin-4-ylcarbonyl)-5-[4-(trifluoromethoxy)phenyl]piperidine-3-carboxylic acid [racemic cis/trans isomer mixture]

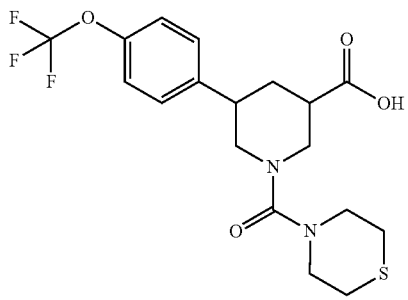 [SMILES: O=C(O)C1CC(c2ccc(OC(F)(F)F)cc2)CN(C(=O)N2CCSCC2)C1]

20.4 g (182 mmol) of potassium tert-butoxide were added at RT to a solution of 7.85 g (18.2 mmol) of the compound from Example 24A in methanol (650 ml). The mixture was stirred at 60° C. overnight. For workup, the methanol was removed under reduced pressure, the residue was admixed with water and the mixture was acidified (pH 1) with aqueous 1 N hydrochloric acid solution. The mixture was extracted with ethyl acetate, and the organic phase was dried with magnesium sulphate, filtered and concentrated under reduced pressure. The reaction led to an 85:15 cis/trans isomer mixture. Yield: 7.70 g (99% of theory)

LC-MS (Method 5B): $R_t$=1.03 (trans isomer) and 1.04 min (cis isomer); MS (ESIpos): m/z=419 [M+H]$^+$;

$^1$H NMR (400 MHz, DMSO-d$_6$): δ=12.44 (br. s., 1H), 7.47-7.39 (m, 2H), 7.31 (d, 2H), 3.79 (d, 1H), 3.56-3.48 (m, 1H), 3.46-3.37 (m, 4H), 2.91-2.73 (m, 3H), 2.63-2.55 (m, 5H), 2.14 (d, 1H), 1.81-1.66 (m, 1H).

Example 26A

{3-[3-(2-Methoxyethyl)-1,2,4-oxadiazol-5-yl]-5-[4-(trifluoromethoxy)phenyl]piperidin-1-yl}-(thiomorpholin-4-yl)methanone [racemic cis isomer]

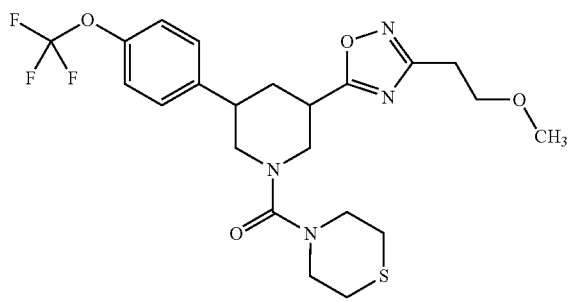 [SMILES: COCCc1noc(C2CC(c3ccc(OC(F)(F)F)cc3)CN(C(=O)N3CCSCC3)C2)n1]

According to General Method 6A, 600 mg (1.43 mmol) of the compound from Example 25A and 232 mg (1.58 mmol) of N-hydroxy-3-methoxypropanimidamide were reacted Yield: 398 mg (53% of theory)

LC-MS (Method 5B): $R_t$=1.21 min; MS (ESIpos): m/z=501 [M+H]$^+$.

$^1$H NMR (400 MHz, DMSO-d$_6$): δ=7.47 (d, 2H), 7.33 (d, 2H), 3.95 (d, 1H), 3.68 (t, 2H), 3.56 (d, 1H), 3.50-3.35 (m, 5H), 3.23 (s, 3H), 3.08-2.86 (m, 5H), 2.60 (br. s., 4H), 2.32 (d, 1H), 1.97 (q, 3H).

Example 27A

{3-(3-Cyclopropyl-1,2,4-oxadiazol-5-yl)-5-[4-(trifluoromethoxy)phenyl]piperidin-1-yl}-(thiomorpholin-4-yl)methanone [racemic cis isomer]

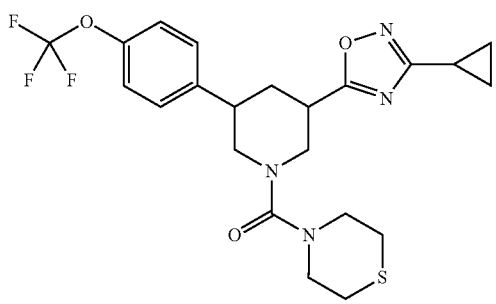 [SMILES: O=C(N1CCSCC1)N1CC(c2ccc(OC(F)(F)F)cc2)CC(c2nc(C3CC3)no2)C1]

According to General Method 6A, 300 mg (0.717 mmol) of the compound from Example 25A and 79 mg (0.789 mmol) of N-hydroxycyclopropanecarboximidamide were reacted Yield: 135 mg (39% of theory)

LC-MS (Method 2B): $R_t$=1.44 min; MS (ESIpos): m/z=483 [M+H]$^+$.

Alternative Synthesis:

600 mg (1.43 mmol) of the compound from Example 25A in dimethylformamide (29.0 ml) were admixed at RT with 654 mg (1.72 mmol) of HATU and 0.55 ml (498 mg, 3.16 mmol) of N,N-diisopropylethylamine, and the mixture was stirred for 30 min. Subsequently, 158 mg (1.58 mmol) of N'-hydroxycyclopropanecarboximidamide were added and the mixture was stirred at RT overnight. The reaction solution was heated to 120° C. and stirred at this temperature for 1 h. The reaction solution was subsequently purified directly by means of preparative HPLC. Yield: 315 mg (45% of theory)

LC-MS (Method 5B): $R_t$=1.30 min; MS (ESIpos): m/z=483 [M+H]$^+$;

$^1$H NMR (400 MHz, DMSO-d$_6$): δ=7.46 (d, 2H), 7.33 (d, 2H), 3.91 (d, 1H), 3.55 (d, 1H), 3.45 (br. s., 4H), 3.39-3.32 (m, 1H), 3.05-2.91 (m, 3H), 2.59 (br. s., 4H), 2.28 (d, 1H), 2.17-2.08 (m, 1H), 1.93 (q, 1H), 1.10-1.02 (m, 2H), 0.92-0.84 (m, 2H).

Example 28A

{3-[3-(2-Ethoxyethyl)-1,2,4-oxadiazol-5-yl]-5-[4-(trifluoromethoxy)phenyl]piperidin-1-yl}-(thiomorpholin-4-yl)methanone [racemic cis isomer]

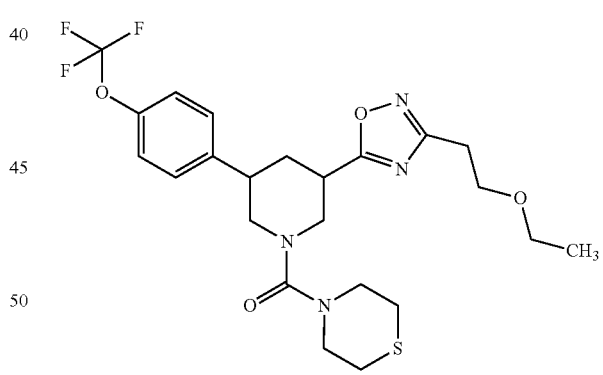

According to General Method 6A, 600 mg (1.434 mmol) of the compound from Example 25A and 307 mg (approx. 1.864 mmol) of 3-ethoxy-N-hydroxypropanimidamide were reacted Yield: 403 mg (55% of theory)

LC-MS (Method 6B): $R_t$=2.61 min; MS (ESIpos): m/z=515 [M+H]$^+$.

$^1$H NMR (400 MHz, DMSO-d$_6$): δ=7.47 (d, 2H), 7.33 (d, 2H), 3.95 (d, 1H), 3.71 (t, 2H), 3.56 (d, 1H), 3.50-3.35 (t, 7H), 3.10-2.88 (m, 5H), 2.60 (br. s., 4H), 2.32 (d, 1H), 2.02-1.92 (m, 1H), 1.07 (t, 3H).

Example 29A

{3-[3-(2-Hydroxyethyl)-1,2,4-oxadiazol-5-yl]-5-[4-(trifluoromethoxy)phenyl]piperidin-1-yl}-(thiomorpholin-4-yl)methanone [racemic cis isomer]

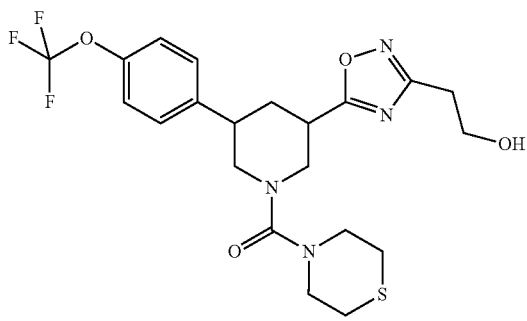 [SMILES: O=C(N1CCSCC1)N1CC(c2ccc(OC(F)(F)F)cc2)CC(c2nc(CCO)no2)C1]

According to General Method 6A, 1.00 g (2.390 mmol) of the compound from Example 25A and 323 mg (3.107 mmol) of N',3-dihydroxypropanimidamide were reacted Yield: 848 mg (69% of theory)

LC-MS (Method 6B): $R_t$=2.26 min; MS (ESIpos): m/z=487 [M+H]$^+$.

Example 30A

3-Methyl 1-(4-nitrophenyl) 5-(4-ethylphenyl)piperidine-1,3-dicarboxylate [racemic cis/trans isomer mixture]

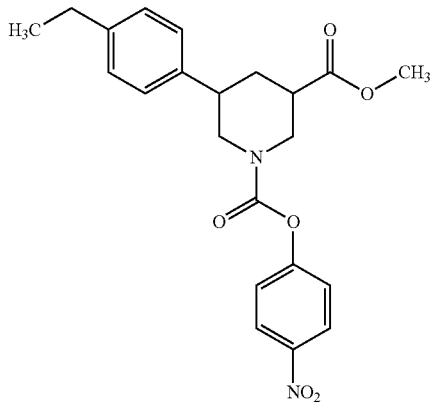 [SMILES: CCc1ccc(C2CC(C(=O)OC)CN(C(=O)Oc3ccc([N+](=O)[O-])cc3)C2)cc1]

3.0 g (12.1 mmol) of the compound from Example 5A were initially charged in 30 ml of dichloromethane, cooled to 0° C. and admixed with 3.4 ml (2.4 g, 12.1 mmol) of triethylamine and 2.4 g (12.1 mmol) of 4-nitrophenyl chloroformate. The reaction mixture was allowed to warm up slowly to RT and stirred at RT for 16 h. The mixture was washed several times with water, dried over sodium sulphate, filtered and concentrated under reduced pressure. The residue was purified by column chromatography on silica gel (eluent dichloromethane→dichloromethane/methanol 100:2). Yield: 4.7 g (83% of theory, purity 89%)

HPLC (Method 1A): $R_t$=4.94 min and 5.00 min (cis/trans isomer); MS (ESIpos): m/z=413 [M+H]$^+$.

Example 31A

4-Nitrophenyl thiomorpholine-4-carboxylate

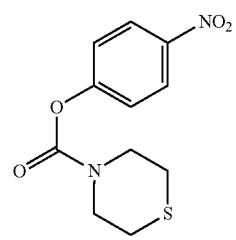 [SMILES: O=C(Oc1ccc([N+](=O)[O-])cc1)N1CCSCC1]

7.7 g (74.4 mmol) of thiomorpholine were initially charged in 100 ml of dichloromethane and, while cooling with an ice bath, admixed with 20.7 ml (15.1 g, 148.8 mmol) of triethylamine. 10.0 g (49.6 mmol) of 4-nitrophenyl chloroformate were added in portions. The reaction mixture was stirred at RT for one hour, and admixed with water and ethyl acetate. The organic phase was removed, washed with 1 N hydrochloric acid and saturated aqueous sodium chloride solution, dried over sodium sulphate, filtered and concentrated under reduced pressure. Yield: 13.2 g (99% of theory)

LC-MS (Method 5B): $R_t$=0.98 min; MS (ESIpos): m/z=269 [M+H]$^+$.

$^1$H NMR (400 MHz, DMSO-d$_6$): δ=8.28 (d, 2H), 7.46 (d, 2H), 3.86 (br. s., 2H), 3.72 (br. s., 2H), 2.71 (br. d., 4H).

Example 32A

4-Nitrophenyl thiomorpholine-4-carboxylate 1-oxide

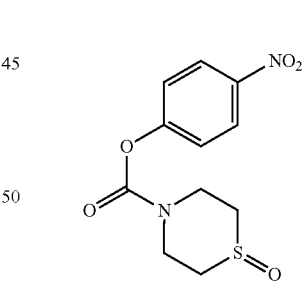

13.1 g (49.0 mmol) of 4-nitrophenyl thiomorpholine-4-carboxylate were initially charged in 135 ml of dichloromethane and admixed at 0° C. with 7.6 g (44.1 mmol) of m-chloroperbenzoic acid in portions. The mixture was stirred at RT for two hours, water was added and the organic phase was removed. The organic phase was washed rapidly with saturated aqueous sodium hydrogencarbonate solution, filtered and concentrated under reduced pressure. The crude product was purified by means of preparative HPLC. Yield: 7.8 g (56% of theory)

LC-MS (Method 5B): $R_t$=0.69 min; MS (ESIpos): m/z=285 [M+H]$^+$.

$^1$H NMR (400 MHz, DMSO-d$_6$): δ=8.30 (d, 2H), 7.49 (d, 2H), 4.20-3.70 (m, 4H), 3.03 (dt, 2H), 2.85 (d, 2H).

Example 33A

[5-(Methoxycarbonyl)pyridin-3-yl]boronic acid hydrochloride

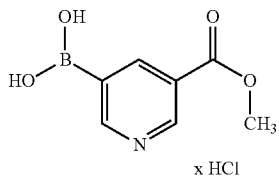

17.6 g (81.4 mmol) of methyl 5-bromonicotinate were initially charged in 375 ml of DMF under argon and admixed with 26.9 g (105.8 mmol) of 4,4,4',4',5,5,5',5'-octamethyl-2,2'-bi-1,3,2-dioxaborolane, 3.0 g (3.6 mmol) of tris(dibenzylideneacetone)dipalladium(0), 1.8 g (6.5 mmol) of tricyclohexylphosphine and 32.0 mmol (325.9 mmol) of potassium acetate. The reaction mixture was stirred at 100° C. for 20 h. Subsequently, the solvent was removed under reduced pressure, the residue was admixed with 40 ml of water and 140 ml of tert-butyl methyl ether, and the organic phase was removed. The aqueous phase was extracted three times with 80 ml each time of tert-butyl methyl ether. The combined organic extracts were washed with saturated aqueous sodium chloride solution, dried over magnesium sulphate, filtered and concentrated. The residue was taken up in 360 ml of methanol and admixed with 36 ml of concentrated hydrochloric acid. The reaction mixture was heated to reflux for 22 h and then stirred at RT for 12 h. About half of the solvent was removed under reduced pressure, and the solution was filtered and concentrated further under reduced pressure. The oily residue was recrystallized twice from acetone, and the residue was taken up in 10 ml of acetone and admixed with 100 ml of tert-butyl methyl ether. After 16 h, the precipitate formed was removed from the solution. This precipitate was stirred in 50 ml of acetone and left to stand at RT for 5 weeks, and the solution was removed again. The solutions were combined, concentrated and dissolved in 50 ml of tert-butyl methyl ether. The mixture was left to stand at RT for 5 weeks and then the precipitate was removed. The precipitate was washed three times with tert-butyl methyl ether and dried in a drying cabinet under reduced pressure.

LC-MS (Method 4B): R$_t$=0.91 min; MS (ESIpos): m/z=182 [M+H]$^+$.

Example 34A

Methyl 5-[4-(difluoromethoxy)phenyl]nicotinate

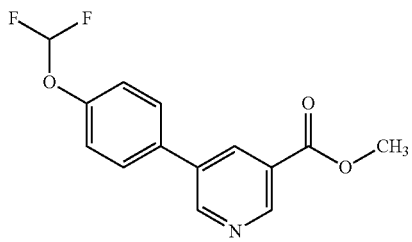 [SMILES: COC(=O)c1cncc(-c2ccc(OC(F)F)cc2)c1]

10.0 g (44.8 mmol) of 4-(difluoromethoxy)bromobenzene were reacted according to General Method 3A with 14.6 g (67.3 mmol) of [5-(methoxycarbonyl)pyridin-3-yl]boronic acid hydrochloride. The release of the hydrochloride was achieved by additional addition of 6.80 g (49.3 mmol) of potassium carbonate. Yield: 8.6 g (67% of theory)

LC-MS (Method 2B): R$_t$=1.15 min; MS (ESIpos): m/z=280 [M+H]$^+$.

Example 35A

Methyl 5-[4-(difluoromethoxy)phenyl]piperidine-3-carboxylate [racemic cis/trans isomer mixture]

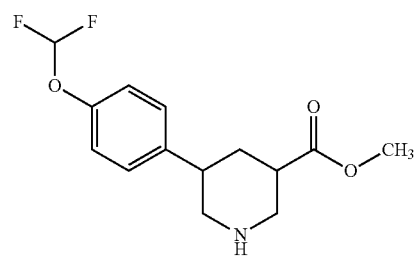 [SMILES: COC(=O)C1CNCC(c2ccc(OC(F)F)cc2)C1]

A solution of 8.6 g (30.9 mmol) of methyl 5-[4-(difluoromethoxy)phenyl]nicotinate in concentrated acetic acid (112 ml) was admixed with 841 mg of palladium/carbon (10% palladium) and 1.12 g of platinum(IV) oxide. This was followed by hydrogenation under a hydrogen atmosphere at standard pressure for 24 h. The reaction solution was concentrated under reduced pressure. The residue was taken up in water, acidified (pH 1) with 1 N hydrochloric acid, extracted with diethyl ether, then basified (pH>10) with saturated aqueous sodium hydrogencarbonate solution and extracted repeatedly with ethyl acetate. The combined filtrates were dried over sodium sulphate, filtered and concentrated under reduced pressure. Yield: 6.6 g (74% of theory)

LC-MS (Method 5B): R$_t$=0.65 min and 0.66 min (cis/trans isomers); MS (ESIpos): m/z=286 [M+H]$^+$.

Example 36A

Methyl 5-[4-(difluoromethoxy)phenyl]-1-[(1,1-dioxidothiomorpholin-4-yl)carbonyl]piperidine-3-carboxylate [cis/trans isomer mixture]

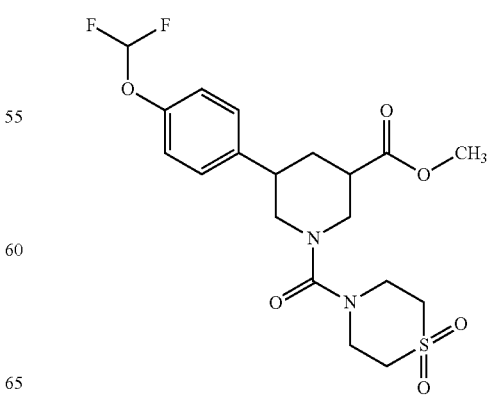

2.2 g (7.7 mmol) of methyl 5-[4-(difluoromethoxy)phenyl]piperidine-3-carboxylate were dissolved in 14 ml of N-methylpyrrolidone, and admixed with 4.0 ml (3.0 g, 23.0 mmol) of N,N-diisopropylethylamine and 3.5 g (11.5 mmol) of 4-nitrophenyl thiomorpholine-4-carboxylate 1,1-dioxide. The reaction mixture was converted in a microwave at 180° C. for seven minutes. Subsequently, water and ethyl acetate were added, and the aqueous phase was removed and extracted repeatedly with ethyl acetate. The combined organic extracts were washed with water and saturated aqueous sodium chloride solution, dried over sodium sulphate, filtered and concentrated under reduced pressure. The residue was taken up in diethyl ether and filtered, and the filtrate was purified by means of preparative HPLC. Yield: 2.0 g (51% of theory)

LC-MS (Method 5B): $R_t$=0.92 min and 0.94 min (cis/trans isomers); MS (ESIpos): m/z=447 [M+H]$^+$.

Example 37A

5-[4-(Difluoromethoxy)phenyl]-1-[(1,1-dioxidothiomorpholin-4-yl)carbonyl]piperidine-3-carboxylic acid [racemic cis isomer mixture]

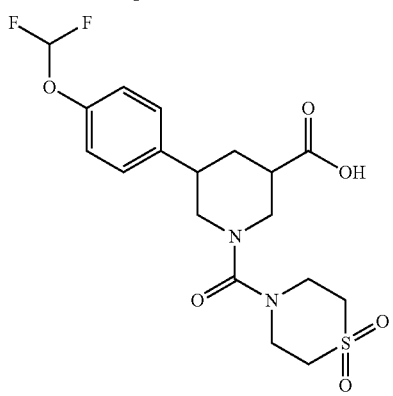

According to General Method 4A, 2.7 g (6.1 mmol) of methyl 5-[4-(difluoromethoxy)phenyl]-1-[(1,1-dioxidothiomorpholin-4-yl)carbonyl]piperidine-3-carboxylate were reacted with 6.9 g (61.3 mmol) of potassium tert-butoxide. Yield: 2.1 g (77% of theory)

LC-MS (Method 5B): $R_t$=0.82 min; MS (ESIpos): m/z=433 [M+H]$^+$.

Example 38A

Methyl 5-[4-(difluoromethoxy)phenyl]-1-[(1-oxidothiomorpholin-4-yl)carbonyl]piperidine-3-carboxylate [cis/trans isomer mixture]

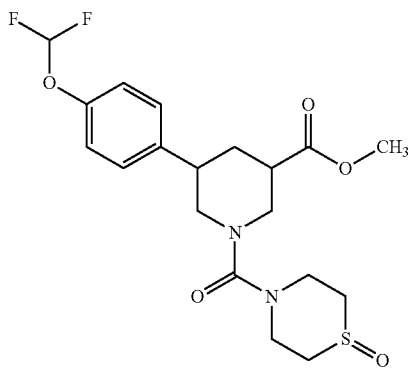 [SMILES: COC(=O)C1CC(c2ccc(OC(F)F)cc2)CN(C(=O)N2CCS(=O)CC2)C1]

2.2 g (7.7 mmol) of methyl 5-[4-(difluoromethoxy)phenyl]piperidine-3-carboxylate were dissolved in 14 ml of N-methylpyrrolidone, and admixed with 4.0 ml (3.0 g, 23.0 mmol) of N,N-diisopropylethylamine and 3.3 g (11.5 mmol) of 4-nitrophenyl thiomorpholine-4-carboxylate 1-oxide. The reaction mixture was converted in a microwave at 180° C. for seven minutes. Subsequently, water and ethyl acetate were added, and the aqueous phase was removed and extracted repeatedly with ethyl acetate. The combined organic extracts were washed with water and saturated aqueous sodium chloride solution, dried over sodium sulphate, filtered and concentrated under reduced pressure. The residue was purified by means of preparative HPLC. Yield: 2.2 g (59% of theory)

LC-MS (Method 5B): $R_t$=0.90 min and 0.92 min (cis/trans isomers); MS (ESIpos): m/z=431 [M+H]$^+$.

Example 39A

5-[4-(Difluoromethoxy)phenyl]-1-[(1-oxidothiomorpholin-4-yl)carbonyl]piperidine-3-carboxylic acid [racemic cis isomer mixture]

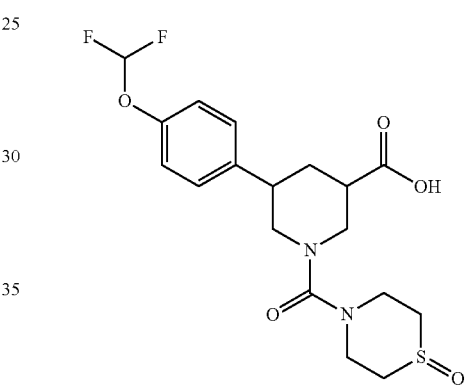

According to General Method 4A, 2.7 g (6.3 mmol) of methyl 5-[4-(difluoromethoxy)phenyl]-1-[(1-oxidothiomorpholin-4-yl)carbonyl]piperidine-3-carboxylate were reacted with 7.1 g (63.3 mmol) of potassium tert-butoxide. The reaction mixture was concentrated under reduced pressure, and the residue was suspended in water and acidified with concentrated hydrochloric acid. The precipitate was filtered off, washed with water and dried under reduced pressure. Yield: 1.1 g (34% of theory)

LC-MS (Method 5B): $R_t$=0.75 min; MS (ESIpos): m/z=417 [M+H]$^+$.

Example 40A

1-Bromo-4-(2,2,2-trifluoroethyl)benzene

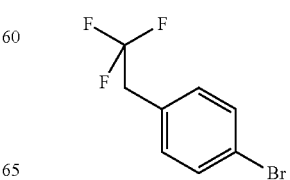

A solution of 25.0 g (100 mmol) of 4-bromobenzyl bromide in 1-methyl-2-pyrrolidone (121 ml) was admixed at RT with 4.95 g (26.0 mmol) of copper(I) iodide and 37.5 g (195 mmol) of methyl 2,2-difluoro-2-(fluorosulphonyl)acetate. The mixture was heated to 80° C. and then stirred overnight. The reaction solution was added to water and extracted with diethyl ether, and the organic phase was dried over sodium sulphate. After filtering and concentrating the organic phase under reduced pressure, the residue was purified by means of column chromatography (silica gel, cyclohexane/ethyl acetate 20:1). Yield: 16.1 g (67% of theory)

GC-MS (Method 1F): $R_t$=2.66 min; MS (ESIpos): m/z=240 [M+H]$^+$.

Example 41A

Methyl 5-[4-(2,2,2-trifluoroethyl)phenyl]nicotinate

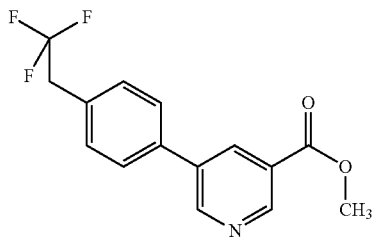 [SMILES: COC(=O)c1cncc(-c2ccc(CC(F)(F)F)cc2)c1]

A solution of 8.00 g (33.5 mmol) of the compound from Example 40A in toluene (304 ml) was admixed under argon at RT with 10.9 g (50.2 mmol) of the compound from Example 33A in ethanol (100 ml) and 5.10 g (36.8 mmol) of potassium carbonate. After stirring for 10 min, 3.87 g (3.35 mmol) of tetrakis(triphenylphosphine)palladium and then 5.83 g (100 mmol) of potassium fluoride in water (64 ml) were added. The mixture was stirred under reflux for 8 h, and the reaction solution was cooled and diluted with ethyl acetate. The reaction solution was washed in water, and the organic phase was dried over magnesium sulphate, filtered and concentrated under reduced pressure. The residue was purified by means of column chromatography (silica gel, dichloromethane/methanol 100:1→80:1). Yield: 9.20 g (69% of theory, purity 75%)

LC-MS (Method 5B): $R_t$=1.06 min; MS (ESIpos): m/z=296 [M+H]$^+$.

Example 42A

Methyl 5-[4-(2,2,2-trifluoroethyl)phenyl]piperidine-3-carboxylate [racemic cis/trans isomer mixture]

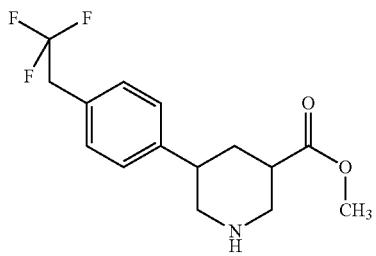 [SMILES: COC(=O)C1CNCC(c2ccc(CC(F)(F)F)cc2)C1]

A solution of 9.20 g (23.4 mmol) of the compound from Example 41A in concentrated acetic acid (192 ml) was admixed with 1.94 g of palladium/carbon (10% palladium) and 2.23 g of platinum(IV) oxide. This was followed by hydrogenation under a hydrogen atmosphere at standard pressure for 6 h, then addition of another 1.00 g of palladium/carbon (10% palladium) and 2.00 g of platinum(IV) oxide, and hydrogenation under a hydrogen atmosphere at standard pressure overnight. Subsequently, a further 1.00 g of palladium/carbon (10% palladium) and 3.00 g of platinum(IV) oxide were added, and hydrogenation was effected under a hydrogen atmosphere at standard pressure for a further 24 h. The reaction solution was filtered through Celite, the filter residue was washed with methanol/water and the combined filtrates were concentrated under reduced pressure. The residue was taken up in dichloromethane and then washed with a 1 N aqueous sodium carbonate solution. The organic phase was dried over sodium sulphate, filtered and concentrated under reduced pressure. Yield: 6.64 g (85% of theory, purity 90%)

LC-MS (Method 2B): $R_t$=0.83 and 0.84 min (cis/trans isomers); MS (ESIpos): m/z=302 [M+H]$^+$.

Example 43A

3-Methyl 1-(4-nitrophenyl) 5-[4-(2,2,2-trifloroethyl)phenyl]piperidine-1,3-dicarboxylate [racemic cis/trans isomer mixture]

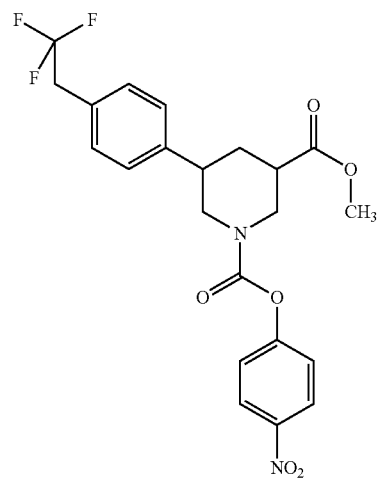 [SMILES: COC(=O)C1CC(c2ccc(CC(F)(F)F)cc2)CN(C(=O)Oc2ccc([N+](=O)[O-])cc2)C1]

A solution of 6.62 g (19.8 mmol, purity 90%) of the compound from Example 42A in dichloromethane (211 ml) was admixed with 9.65 ml (7.00 g, 69.2 mmol) of triethylamine and then admixed at 0° C. with 3.99 g (19.8 mmol) of 4-nitrophenyl chloroformate. The mixture was warmed to RT and stirred for 1 h. The reaction solution was washed with saturated aqueous sodium hydrogencarbonate solution and water, and the organic phase was dried over magnesium sulphate, filtered and concentrated under reduced pressure. Yield: 10.3 g (91% of theory, purity 81%)

LC-MS (Method 2B): $R_t$=1.40 and 1.42 min (cis/trans isomers); MS (ESIpos): m/z=467 [M+H]$^+$.

Example 44A

Methyl 1-(thiomorpholin-4-ylcarbonyl)-5-[4-(2,2,2-trifluoroethyl)phenyl]piperidine-3-carboxylate [racemic cis/trans isomer mixture]

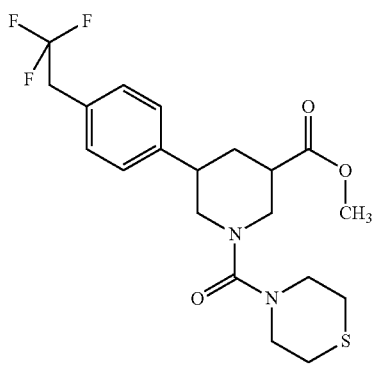 [SMILES: COC(=O)C1CC(c2ccc(CC(F)(F)F)cc2)CN(C(=O)N2CCSCC2)C1]

A solution of 10.3 g (17.9 mmol, purity 81%) of the compound from Example 43A in 1-methyl-2-pyrrolidone (65 ml) was admixed with 12.6 ml (13.7 g, 132 mmol) of thiomorpholine and 11.5 ml (8.56 g, 66.2 mmol) of N,N-diisopropylethylamine and then heated in 5 portions in a single-mode microwave (Emrys Optimizer) at 150° C. for 1 h. For workup, the reaction solutions were combined and purified directly by means of preparative HPLC. Yield: 5.63 g (71% of theory)

LC-MS (Method 5B): $R_t$=1.13 and 1.16 min (cis/trans isomers); MS (ESIpos): m/z=431 [M+H]$^+$.

Example 45A 1-(Thiomorpholin-4-ylcarbonyl)-5-[4-(2,2,2-trifluoroethyl)phenyl]piperidine-3-carboxylic acid [racemic cis isomer]

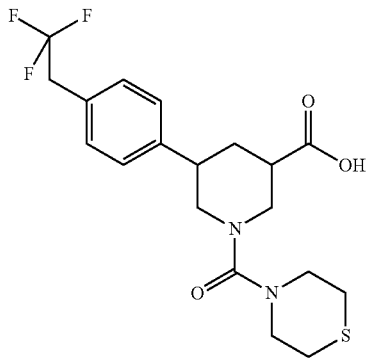 [SMILES: O=C(O)C1CC(c2ccc(CC(F)(F)F)cc2)CN(C(=O)N2CCSCC2)C1]

7.74 g (69.0 mmol) of potassium tert-butoxide were added at RT to a solution of 2.97 g (6.90 mmol) of the compound from Example 44A in methanol (83 ml). The mixture was stirred at 60° C. overnight. For workup, the methanol was removed under reduced pressure, the residue was admixed with water and the mixture was acidified (pH 1) with aqueous 1 N hydrochloric acid solution. The mixture was extracted with ethyl acetate, and the organic phase was dried with magnesium sulphate, filtered and concentrated under reduced pressure. Yield: 2.61 g (76% of theory, purity 84%)

LC-MS (Method 5B): $R_t$=1.02 min; MS (ESIpos): m/z=417 [M+H]$^+$.

Example 46A

{3-(3-Cyclopropyl-1,2,4-oxadiazol-5-yl)-5-[4-(2,2,2-trifluoroethyl)phenyl]piperidin-1-yl}-(thiomorpholin-4-yl)methanone [racemic cis isomer]

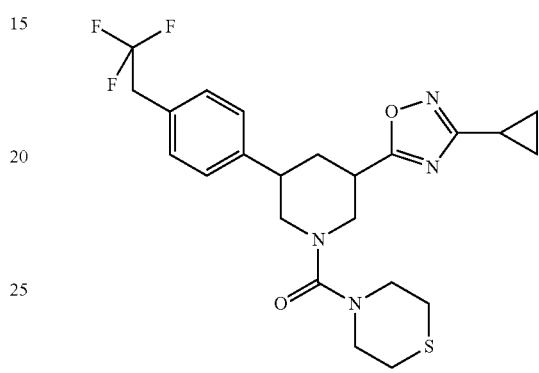

According to General Method 6A, 300 mg (0.720 mmol) of the compound from Example 45A and 79.3 mg (0.792 mmol) of N-hydroxycyclopropanecarboximidamide were reacted Yield: 160 mg (45% of theory)

LC-MS (Method 5B): $R_t$=1.23 min; MS (ESIpos): m/z=481 [M+H]$^+$.

$^1$H NMR (400 MHz, DMSO-$d_6$): δ=7.32 (s, 4H), 3.92 (d, 1H), 3.68-3.52 (m, 3H), 3.44 (br. s., 4H), 3.39-3.33 (m, 1H), 3.03-2.85 (m, 3H), 2.59 (br. s., 5H), 2.28 (d, 1H), 2.16-2.06 (m, 1H), 1.92 (q, 1H), 1.10-1.01 (m, 2H), 0.92-0.85 (m, 2H).

Example 47A

{3-[3-(2-Methoxyethyl)-1,2,4-oxadiazol-5-yl]-5-[4-(2,2,2-trifluoroethyl)phenyl]piperidin-1-yl}-(thiomorpholin-4-yl)methanone [racemic cis isomer]

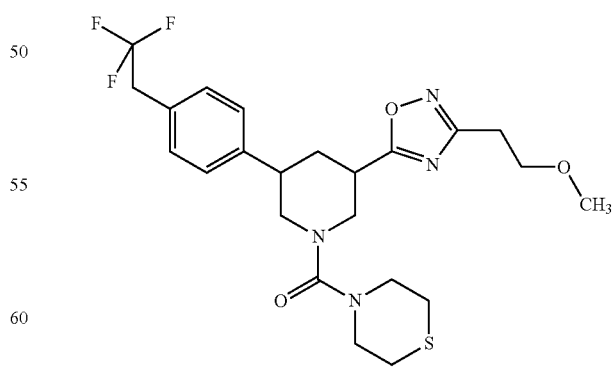

According to General Method 6A, 300 mg (0.720 mmol) of the compound from Example 45A and 93.6 mg (0.792 mmol) of N-hydroxy-3-methoxypropanimidamide were reacted Yield: 231 mg (63% of theory, approx. 15% trans isomer)

LC-MS (Method 5B): R$_t$=1.14 min; MS (ESIpos): m/z=499 [M+H]$^+$.

Example 48A

1-Bromo-4-(1,1-difluoroethyl)benzene

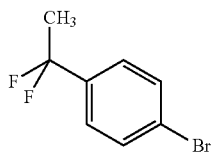

A solution of 10.0 g (50.2 mmol) of 4-bromoacetophenone in tetrahydrofuran (20 ml) was admixed with 50.0 ml (151 mmol, 50% in tetrahydrofuran) of bis(2-methoxyethyl)aminosulphur trifluoride (Deoxofluor) and 3 drops of methanol, and then stirred under reflux for 4 days. The reaction mixture was cautiously added dropwise to a mixture of saturated aqueous sodium hydrogencarbonate solution and ice (1:1) and then extracted with diethyl ether. The organic phase was dried over sodium sulphate, filtered and concentrated under reduced pressure. The residue was purified by means of column chromatography (silica gel, petroleum ether/dichloromethane 3:1). Yield: 8.46 g (76% of theory)

$^1$H NMR (400 MHz, DMSO-d$_6$): δ=7.70 (d, 2H), 7.52 (d, 2H), 1.96 (t, 3H).

Example 49A

Methyl 5-[4-(1,1-difluoroethyl)phenyl]nicotinate

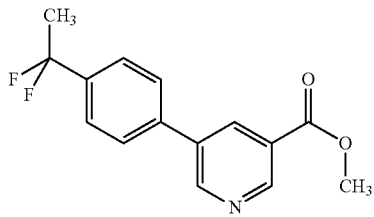 [SMILES: COC(=O)c1cncc(-c2ccc(C(C)(F)F)cc2)c1]

A solution of 2.98 g (13.3 mmol) of the compound from Example 48A in toluene (25.0 ml) was admixed under argon at RT with 3.62 g (16.7 mmol) of the compound from Example 33A in ethanol (8.4 ml) and 2.03 g (14.7 mmol) of potassium carbonate. After stirring for 10 min, 1.54 g (1.34 mmol) of tetrakis(triphenylphosphine)palladium and then 2.33 g (40.0 mmol) of potassium fluoride in water (5.8 ml) were added. The mixture was stirred under reflux for 8 h, and the reaction solution was cooled and diluted with ethyl acetate. The reaction solution was washed in water, and the organic phase was dried over magnesium sulphate, filtered and concentrated under reduced pressure. The residue was purified by means of column chromatography (silica gel, dichloromethane/methanol 100:1→80:1). Yield: 2.62 g (69% of theory, 4:1 mixture of methyl and ethyl ester)

LC-MS (Method 2B): R$_t$=1.20 min (methyl ester) and 1.28 min (ethyl ester); MS (ESIpos): m/z=278 [M+H]$^+$(methyl ester) and 292 [M+H]$^+$(ethyl ester).

Example 50A

Methyl 5-[4-(1,1-difluoroethyl)phenyl]piperidine-3-carboxylate [racemic cis/trans isomer mixture]

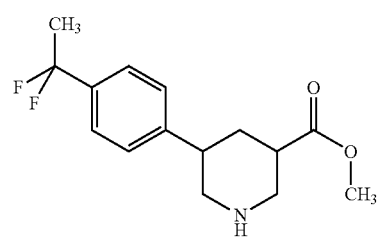 [SMILES: COC(=O)C1CNCC(c2ccc(C(C)(F)F)cc2)C1]

A solution of 2.30 g (8.30 mmol) of the compound from Example 49A in methanol (52 ml) and concentrated hydrogen chloride solution (6.5 ml) was admixed with 1.05 g of palladium/carbon (10% palladium) and 1.92 g of platinum (IV) oxide and then hydrogenated overnight in a hydrogen atmosphere at standard pressure. The reaction solution was filtered through Celite, the filter residue was washed with methanol/water and the combined filtrates were concentrated under reduced pressure. The residue was taken up in dichloromethane and then washed with a 1 N aqueous sodium carbonate solution. The organic phase was dried over sodium sulphate, filtered and concentrated under reduced pressure. Yield: 2.30 g (81% of theory, purity 82%)

LC-MS (Method 2B): R$_t$=0.80 and 0.81 min (cis/trans isomers); MS (ESIpos): m/z=284 [M+H]$^+$.

Example 51A

3-Methyl 1-(4-nitrophenyl) 5-[4-(1,1-difluoroethyl)phenyl]piperidine-1,3-dicarboxylate [racemic cis/trans isomer mixture]

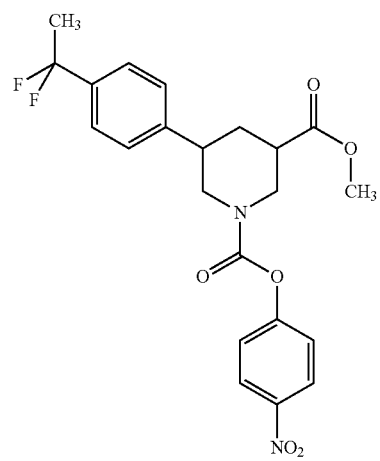 [SMILES: COC(=O)C1CC(c2ccc(C(C)(F)F)cc2)CN(C(=O)Oc2ccc([N+](=O)[O-])cc2)C1]

A solution of 1.30 g (3.78 mmol, purity 82%) of the compound from Example 50A in dichloromethane (44 ml) was admixed with 1.84 ml (1.34 g, 13.2 mmol) of triethylamine and then admixed at 0° C. with 762 mg (3.78 mmol) of 4-nitrophenyl chloroformate. The mixture was warmed to RT and stirred for 2 days. The reaction solution was washed with saturated aqueous sodium hydrogencarbonate solution and water, and the organic phase was dried over magnesium sulphate, filtered and concentrated under reduced pressure. Yield: 1.93 g (92% of theory, purity 81%, 2:1 mixture of methyl and ethyl ester)

LC-MS (Method 5B): $R_t$=2.58 min and 2.61 (methyl ester, cis/trans isomers) and 2.68 and 2.70 (ethyl ester, cis/trans isomers); MS (ESIpos): m/z=278 [M+H]$^+$(methyl ester) and 292 [M+H]$^+$(ethyl ester).

Example 52A

Methyl 5-[4-(1,1-difluoroethyl)phenyl]-1-(thiomorpholin-4-ylcarbonyl)piperidine-3-carboxylate [racemic cis/trans isomer mixture]

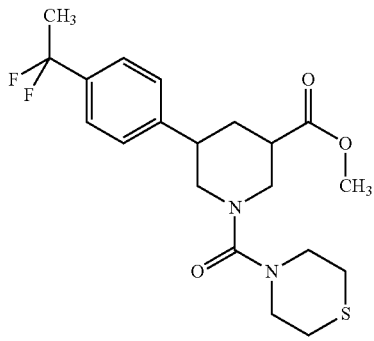 [SMILES: COC(=O)C1CC(c2ccc(C(C)(F)F)cc2)CN(C(=O)N2CCSCC2)C1]

A solution of 1.94 g (3.50 mmol, purity 81%) of the compound from Example 51A in 1-methyl-2-pyrrolidone (18 ml) was admixed with 1.99 ml (2.17 g, 21.0 mmol) of thiomorpholine and 1.83 ml (1.36 g, 10.5 mmol) of N,N-diisopropylethylamine and then heated in 3 portions in a single-mode microwave (Emrys Optimizer) at 150° C. for 45 min. For workup, the reaction solutions were combined and purified directly by means of preparative HPLC. Yield: 530 mg (34% of theory)

LC-MS (Method 5B): $R_t$=2.28 and 2.35 min (cis/trans isomers); MS (ESIpos): m/z=413 [M+H]$^+$.

Example 53A

5-[4-(1,1-Difluoroethyl)phenyl]-1-(thiomorpholin-4-ylcarbonyl)piperidine-3-carboxylic acid [racemic cis/trans isomer mixture]

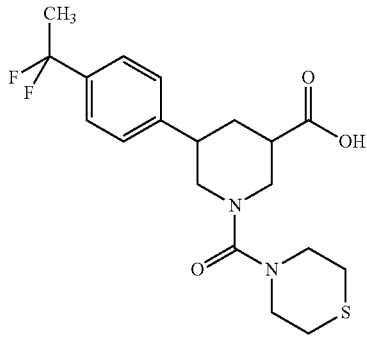 [SMILES: CC(F)(F)c1ccc(C2CC(C(=O)O)CN(C(=O)N3CCSCC3)C2)cc1]

1.44 g (12.8 mmol) of potassium tert-butoxide were added at RT to a solution of 528 mg (1.28 mmol) of the compound from Example 52A in 15 ml of methanol. The mixture was stirred at 60° C. overnight. For workup, the methanol was removed under reduced pressure, the residue was admixed with water and the mixture was acidified (pH 1) with aqueous 1 N hydrochloric acid solution. The mixture was extracted with ethyl acetate, and the organic phase was dried with magnesium sulphate, filtered and concentrated under reduced pressure. Yield: 471 mg (91% of theory, 2:1 cis/trans isomer mixture)

LC-MS (Method 5B): $R_t$=0.99 and 1.01 min; MS (ESIpos): m/z=399 [M+H]$^+$.

Example 54A

{3-(3-Cyclopropyl-1,2,4-oxadiazol-5-yl)-5-[4-(1,1-difluoroethyl)phenyl]piperidin-1-yl}-(thiomorpholin-4-yl)methanone [racemic cis isomer]

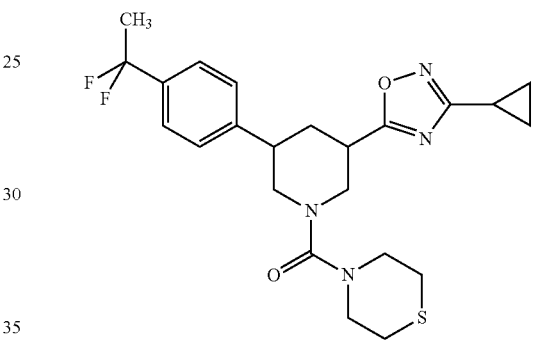

According to General Method 6A, 150 mg (0.376 mmol) of the compound from Example 53A and 41.5 mg (0.414 mmol) of N-hydroxycyclopropanecarboximidamide were reacted Yield: 77.9 mg (44% of theory)

LC-MS (Method 2B): $R_t$=1.37 min; MS (ESIpos): m/z=463 [M+H]$^+$.

Example 55A

Methyl 5-[4-(2-hydroxyethyl)phenyl]nicotinate

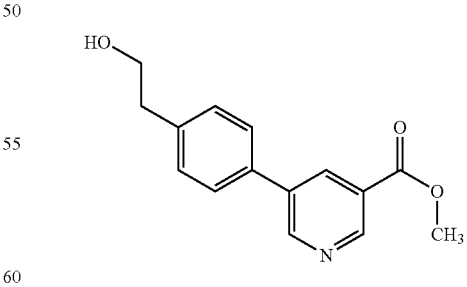

According to General Method 3A, 6.00 g (29.8 mmol) of 2-(4-bromophenyl)ethanol and 19.6 g (74.6 mmol) of methyl 5-(4,4,5,5-tetramethyl-1,3,2-dioxaborolan-2-yl)nicotinate were reacted. Yield: 6.12 g (74% of theory)

LC-MS (Method 2B): $R_t$=0.86 min; MS (ESIpos): m/z=258 [M+H]$^+$.

Example 56A

Methyl 5-[4-(2-hydroxyethyl)phenyl]piperidine-3-carboxylate [racemic cis/trans isomer mixture]

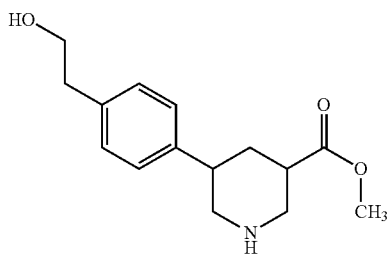 [SMILES: COC(=O)C1CNCC(c2ccc(CCO)cc2)C1]

A solution of 5.40 g (19.6 mmol) of the compound from Example 55A in concentrated acetic acid (124 ml) was admixed with 1.00 g of palladium/carbon (10% palladium) and 1.00 g of platinum(IV) oxide. This was followed by hydrogenation under a hydrogen atmosphere at standard pressure for 6 h, then addition of another 1.00 g of palladium/carbon (10% palladium) and 1.00 g of platinum(IV) oxide, and hydrogenation under a hydrogen atmosphere at standard pressure overnight. This was followed by hydrogenation in a Pan apparatus under a 3 bar hydrogen atmosphere for a further 2 h. The reaction solution was filtered through Celite, the filter residue was washed with methanol/water and the combined filtrates were concentrated under reduced pressure. The residue was codistilled repeatedly with toluene and then dried under high vacuum. Yield: 6.63 g (56% of theory, purity 44%)

LC-MS (Method 2B): $R_t$=0.36 min and 0.40 min (cis/trans isomers); MS (ESIpos): m/z=264 [M+H]$^+$.

Example 57A

Methyl 1-acetyl-5-[4-(2-hydroxyethyl)phenyl]piperidine-3-carboxylate [racemic cis/trans isomer mixture]

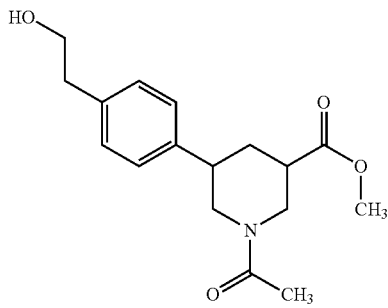 [SMILES: COC(=O)C1CC(c2ccc(CCO)cc2)CN(C(C)=O)C1]

A solution of 5.58 g (9.33 mmol, purity 44%) of the compound from Example 56A in dichloromethane (80 ml) was admixed with 2.60 ml (1.89 g, 18.7 mmol) of triethylamine and then cooled to 0° C. At this temperature, 0.33 ml (0.37 g, 4.67 mmol) of acetyl chloride was added dropwise and the mixture was stirred for 2 h. A further 0.13 ml (0.15 g, 1.86 mmol) of acetyl chloride was added and the mixture was stirred for 1 h. Subsequently, the reaction solution was washed with aqueous 1 N hydrochloric acid, and the organic phase was dried over magnesium sulphate, filtered and concentrated under reduced pressure. The residue was purified by means of column chromatography (silica gel, dichloromethane/methanol 30:1), and the crude product obtained was purified once more by means of preparative HPLC. Yield: 1.17 g (41% of theory)

LC-MS (Method 5B): $R_t$=0.72 min and 0.74 min (cis/trans isomers); MS (ESIpos): m/z=306 [M+H]$^+$.

Example 58A

Methyl 1-acetyl-5-[4-(2,2-difluoroethyl)phenyl]piperidine-3-carboxylate [racemic cis/trans isomer mixture]

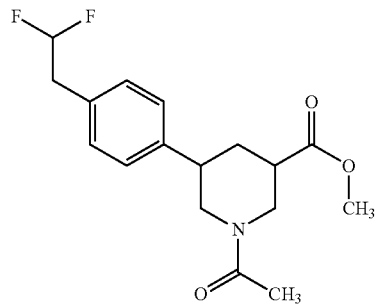 [SMILES: COC(=O)C1CC(c2ccc(CC(F)F)cc2)CN(C(C)=O)C1]

A solution of 631 mg (2.05 mmol) of the compound from Example 57A in dichloromethane (20.8 ml) was admixed with 1.45 ml (1.60 g, 20.5 mmol) of dimethyl sulphoxide and 1.78 ml (1.32 g, 10.2 mmol) of N,N-diisopropylamine. Subsequently, 1.30 g (8.18 mmol) of sulphur trioxide-pyridine complex were added at −20° C. and the mixture was stirred overnight, in the course of which it was warmed slowly to RT. The reaction solution was diluted with dichloromethane, and the organic phase was washed with water, dried over magnesium sulphate, filtered and concentrated under reduced pressure. The crude product (778 mg) was subsequently initially charged in dichloromethane (5.2 ml) and admixed dropwise at RT with 0.50 ml (615 mg, 3.81 mmol) of diethylaminosulphur trifluoride (DAST). The mixture was stirred at RT for 4 h and then the reaction was ended by cautiously adding 2 N aqueous sodium carbonate solution. After phase separation, the organic phase was dried over magnesium sulphate, filtered and concentrated under reduced pressure. The crude product was purified by means of preparative HPLC. Yield: 120 mg (24% of theory, purity 61%, approx. 2:1 cis/trans isomer mixture)

LC-MS (Method 2B): $R_t$=1.07 min and 1.09 min (cis/trans isomers); MS (ESIpos): m/z=326 [M+H]$^+$.

Example 59A

1-Acetyl-5-[4-(2,2-difluoroethyl)phenyl]piperidine-3-carboxylic acid [racemic cis isomer]

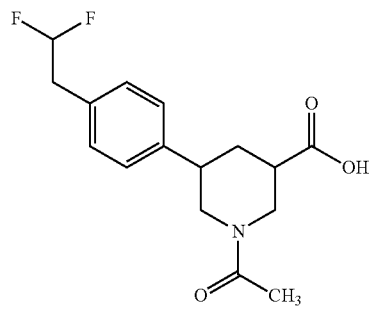 [SMILES: CC(=O)N1CC(C(=O)O)CC(c2ccc(CC(F)F)cc2)C1]

410 mg (3.65 mmol) of potassium tert-butoxide were added at RT to a solution of 205 mg (0.365 mmol, purity 61%) of the compound from Example 58A in methanol (6.9 ml). The mixture was stirred at 60° C. overnight. For workup, the methanol was removed under reduced pressure, the residue was admixed with water and the mixture was acidified (pH 1) with aqueous 1 N hydrochloric acid solution. The mixture was extracted with ethyl acetate, and the organic phase was dried with magnesium sulphate, filtered and concentrated under reduced pressure. Yield: 153 mg (67% of theory, purity 50%)

LC-MS (Method 5B): $R_t$=1.74 min; MS (ESIpos): m/z=312 [M+H]$^+$.

Example 60A

1-{3-[4-(2,2-Difluoroethyl)phenyl]-5-[3-(2-methoxyethyl)-1,2,4-oxadiazol-5-yl]piperidin-1-yl}-ethanone [racemic cis isomer]

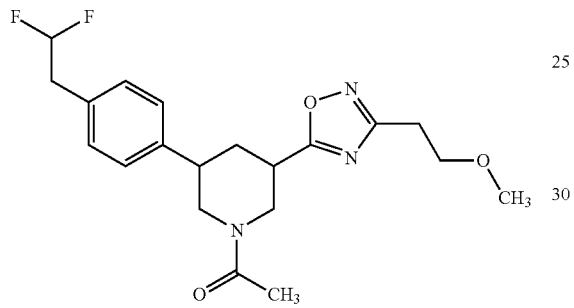

According to General Method 6A, 153 mg (0.270 mmol, purity 50%) of the compound from Example 59A and 41.3 mg (0.297 mmol, purity 85%) of N-hydroxy-3-methoxypropanimidamide were reacted Yield: 46.6 mg (32% of theory, purity 72%)

LC-MS (Method 2B): $R_t$=1.07 min; MS (ESIpos): m/z=394 [M+H]$^+$.

Example 61A

3-[4-(2,2-Difluoroethyl)phenyl]-5-[3-(2-methoxyethyl)-1,2,4-oxadiazol-5-yl]piperidine [racemic cis isomer]

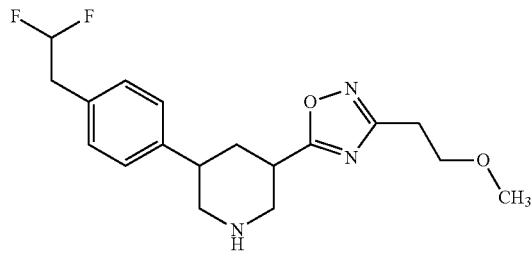 [SMILES: COCCc1noc(C2CNCC(c3ccc(CC(F)F)cc3)C2)n1]

A solution of 45.0 mg (0.083 mmol, purity 72%) of the compound from Example 60A in ethanol (10.0 ml) was admixed with 69 µl (15 mg, 0.42 mmol) of concentrated hydrochloric acid. Subsequently, the mixture was stirred under reflux for 24 h, and the reaction solution was diluted with water and washed with diethyl ether. The aqueous phase was alkalized and extracted with dichloromethane. The organic phase was dried over magnesium sulphate, filtered and concentrated under reduced pressure. Yield: 36.3 mg (87% of theory, purity 70%)

LC-MS (Method 5B): $R_t$=0.71 min; MS (ESIpos): m/z=352 [M+H]$^+$.

Example 62A

4-Nitrophenyl 3-[4-(2,2-difluoroethyl)phenyl]-5-[3-(2-methoxyethyl)-1,2,4-oxadiazol-5-yl]piperidine-1-carboxylate [racemic cis isomer]

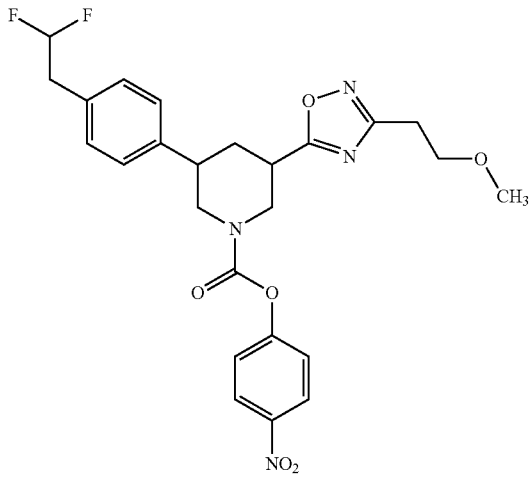 [SMILES: COCCc1noc(C2CC(c3ccc(CC(F)F)cc3)CN(C(=O)Oc3ccc([N+](=O)[O-])cc3)C2)n1]

A solution of 36.3 mg (0.061 mmol, purity 70%) of the compound from Example 61A in dichloromethane (2.0 ml) was admixed with 0.03 ml (21.6 mg, 0.21 mmol) of triethylamine and then 12.3 mg (0.061 mmol) of 4-nitrophenyl chloroformate were added at RT. The mixture was stirred at RT for 2 h and then the reaction solution was washed with saturated aqueous sodium hydrogencarbonate solution and water, and the organic phase was dried over magnesium sulphate, filtered and concentrated under reduced pressure. Yield: 56.2 mg (91% of theory, purity 60%)

LC-MS (Method 4B): $R_t$=2.56 min; MS (ESIpos): m/z=517 [M+H]$^+$.

Example 63A

{3-[4-(2,2-Difluoroethyl)phenyl]-5-[3-(2-methoxyethyl)-1,2,4-oxadiazol-5-yl]piperidin-1-yl}(thiomorpholin-4-yl)methanone [racemic cis isomer]

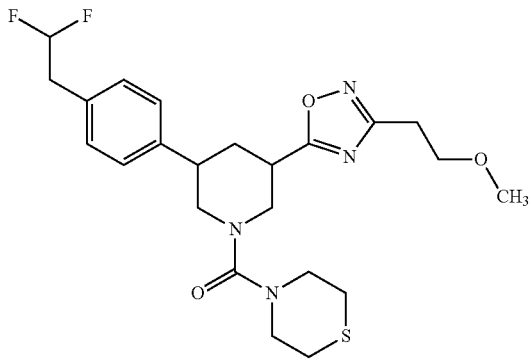 [SMILES: COCCc1noc(C2CC(c3ccc(CC(F)F)cc3)CN(C(=O)N3CCSCC3)C2)n1]

A solution of 56.0 mg (0.065 mmol, purity 60%) of the compound from Example 62A in 1-methyl-2-pyrrolidone (2.0 ml) was admixed with 37.0 μl (40.0 mg, 0.390 mmol) of thiomorpholine and 34.0 μl (25.0 mg, 0.195 mmol) of N,N-diisopropylethylamine and then heated in a single-mode microwave (Emrys Optimizer) at 150° C. for 30 min. For workup, the reaction solutions were combined and purified directly by means of preparative HPLC. Yield: 14.7 mg (47% of theory)

LC-MS (Method 5B): R$_t$=1.09 min; MS (ESIpos): m/z=481 [M+H]$^+$.

Example 64A

N-Hydroxy-1-methoxycyclopropanecarboximidamide

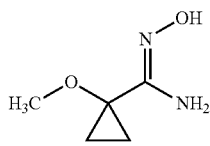

100 mg (1.03 mmol) of 1-methoxycyclopropanecarboxamide [L. N. Owen, H. M. Babatunde Somade, *J. Chem. Soc.* 1947, 1030-1034] in tetrahydrofuran (22.7 ml) was admixed with 1.51 g (6.08 mmol) of methyl N-(triethylammoniumsulphonyl)carbamate (Burgess reagent) and then stirred at 60° C. for 1.5 h. The reaction mixture was admixed with dichloromethane and water, and the organic phase was dried over magnesium sulphate, filtered and concentrated under reduced pressure (637 mg of crude product). 100 mg of the crude product were initially charged in ethanol (1.2 ml), admixed with 107 mg (1.55 mmol) of hydroxylammonium chloride and 0.17 ml (125 mg, 1.24 mg) of triethylamine and then stirred under reflux overnight. The reaction solution was concentrated under reduced pressure, and the residue was admixed with saturated aqueous sodium chloride solution and then extracted with dichloromethane. The organic phase was dried over magnesium sulphate, filtered and concentrated under reduced pressure. The residue was subsequently stirred with ethyl acetate, the insoluble salts were filtered off and the filtrate was concentrated under reduced pressure. Yield: 32.3 mg (23% of theory)

$^1$H NMR (400 MHz, DMSO-d$_6$): δ=9.09 (br. s., 1H), 5.39 (br. s., 2H), 3.15 (s, 3H), 0.81 (d, 4H).

Example 65A

{3-[3-(1-Methoxycyclopropyl)-1,2,4-oxadiazol-5-yl]-5-[4-(2,2,2-trifluoroethyl)phenyl]piperidin-1-yl}(thiomorpholin-4-yl)methanone [racemic cis isomer]

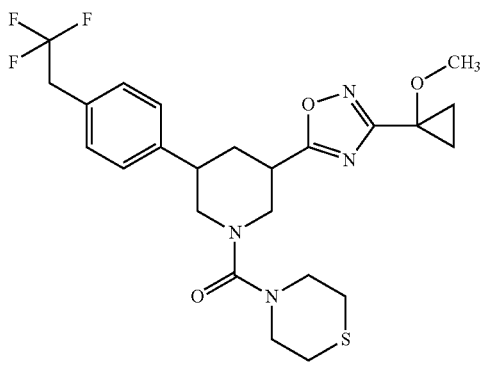 [SMILES: COC1(c2noc(C3CC(c4ccc(CC(F)(F)F)cc4)CN(C(=O)N4CCSCC4)C3)n2)CC1]

According to General Method 6A, 93.1 mg (0.224 mmol) of the compound from Example 45A and 32.0 mg (0.246 mmol) of N-hydroxy-1-methoxycyclopropanecarboximidamide from Example 64A were reacted. Yield: 31.1 mg (27% of theory)

LC-MS (Method 5B): R$_t$=1.22 min; MS (ESIpos): m/z=511 [M+H]$^+$.

$^1$H NMR (400 MHz, DMSO-d$_6$): δ=7.33 (s, 4H), 3.94 (d, 1H), 3.69-3.52 (m, 3H), 3.48-3.42 (m, 4H), 3.41-3.34 (m, 4H), 3.06-2.85 (m, 3H), 2.63-2.57 (m, 4H), 2.32-2.25 (m, 1H), 2.02-1.88 (m, 1H), 1.34-1.28 (m, 2H), 1.19-1.11 (m, 2H).

Example 66A

4-Nitrophenyl thiomorpholine-4-carboxylate 1,1-dioxide

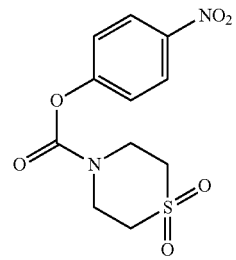 [SMILES: O=C(Oc1ccc([N+](=O)[O-])cc1)N1CCS(=O)(=O)CC1]

17.0 g (99.2 mmol) of thiomorpholine 1,1-dioxide hydrochloride were initially charged in 100 ml of dichloromethane and, while cooling with an ice bath, admixed with 20.7 ml (15.1 g, 148.8 mmol) of triethylamine. 10.0 g (49.6 mmol) of 4-nitrophenyl chloroformate were added in portions. The reaction mixture was stirred at RT for 30 minutes, admixed with water and ethyl acetate and then filtered. The residue was dried under high vacuum. Yield: 12.4 g (83% of theory)

LC-MS (Method 5B): R$_t$=0.75 min; MS (ESIpos): m/z=301 [M+H]$^+$.

$^1$H NMR (400 MHz, DMSO-d$_6$): δ=8.34-8.28 (m, 2H), 7.55-7.50 (m, 2H), 4.01 (br. s., 2H), 3.87 (br. s., 2H), 3.37 (br. s., 2H), 3.28 (br. s., 2H).

Working Examples

General Method 1: Sulphoxide Formation

A solution of the appropriate thioether (1.0 eq) in dichloromethane (approx. 20-40 ml/mmol) is admixed at RT with 50% meta-chloroperoxybenzoic acid (0.9-1.0 eq.). The reaction mixture is stirred at room temperature for 30 min. The solvent is removed under reduced pressure and the residue is purified by means of preparative HPLC.

General Method 2: Sulphone Formation

A solution of the appropriate thioether (1.0 eq) in dichloromethane (approx. 20-40 ml/mmol) is admixed at RT with 50% meta-chloroperoxybenzoic acid (2.5 eq.). The reaction mixture is stirred at room temperature for 30 min. The solvent is removed under reduced pressure and the residue is purified by means of preparative HPLC.

Example 1

{3-[3-(2-Methoxyethyl)-1,2,4-oxadiazol-5-yl]-5-[4-(trifluoromethoxy)phenyl]piperidin-1-yl}-(oxidothiomorpholin-4-yl)methanone [racemic cis isomer]

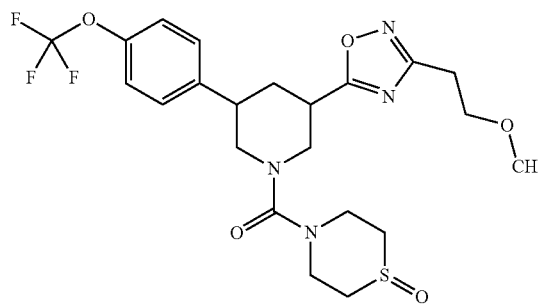

According to General Method 1, 100 mg (0.200 mmol) of the compound from Example 26A were reacted. Yield: 90 mg (87% of theory)

LC-MS (Method 5B): $R_t$=0.97 min; MS (ESIpos): m/z=517 [M+H]$^+$;

$^1$H NMR (400 MHz, DMSO-d$_6$): δ=7.48 (d, 2H), 7.33 (d, 3H), 3.99 (d, 1H), 3.69-3.66 (m, 3H), 3.65-3.58 (m, 4H), 3.57-3.48 (m, 3H), 3.23 (s, 3H), 3.09-2.88 (m, 7H), 2.75-2.66 (m, 3H), 2.35-2.28 (m, 1H), 2.00 (m, 1H).

Example 2

{3-(3-Cyclopropyl-1,2,4-oxadiazol-5-yl)-5-[4-(trifluoromethoxy)phenyl]piperidin-1-yl}(1-oxidothiomorpholin-4-yl)methanone [racemic cis isomer]

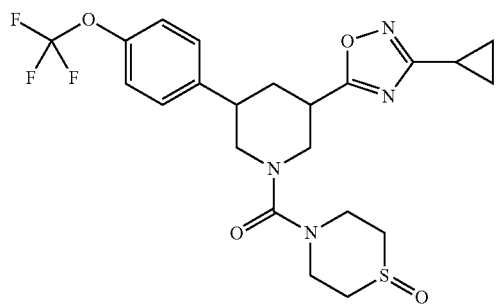 [SMILES: O=C(N1CCS(=O)CC1)N1CC(c2ccc(OC(F)(F)F)cc2)CC(c2nc(C3CC3)no2)C1]

According to General Method 1, 100 mg (0.207 mmol) of the compound from Example 27A were reacted. Yield: 95 mg (91% of theory)

LC-MS (Method 5B): $R_t$=1.05 min; MS (ESIpos): m/z=499 [M+H]$^+$;

$^1$H NMR (400 MHz, DMSO-d$_6$): δ=7.47 (d, 2H), 7.33 (d, 2H), 3.95 (d, 1H), 3.67-3.48 (m, 5H), 3.05-2.85 (m, 5H), 2.75-2.65 (m, 2H), 2.28 (d, 1H), 2.14-2.08 (m, 1H), 1.94 (q, 1H), 1.09-1.01 (m, 2H), 0.92-0.84 (m, 2H).

Example 3

[3-(3-Cyclopropyl-1,2,4-oxadiazol-5-yl)-5-(4-ethylphenyl)piperidin-1-yl](1-oxidothiomorpholin-4-yl)methanone [racemic cis isomer]

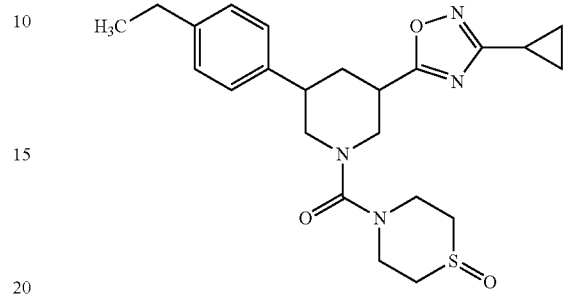

According to General Method 1, 55 mg (0.130 mmol) of the compound from Example 9A were reacted. Yield: 43 mg (75% of theory)

LC-MS (Method 5B): $R_t$=1.06 min; MS (ESIpos): m/z=443 [M+H]$^+$;

$^1$H NMR (400 MHz, DMSO-d$_6$): δ=7.24 (d, 2H), 7.17 (d, 2H), 3.96 (d, 2H), 3.67-3.46 (m, 5H), 3.045-2.85 (m, 5H), 2.74-2.66 (m, 2H), 2.57 (q, 2H), 2.25 (d, 1H), 2.14-2.06 (m, 1H), 1.91 (q, 1H), 1.16 (t, 3H), 1.08-1.02 (m, 2H), 0.91-0.86 (m, 2H.)

Example 4

{3-[3-(2-Ethoxyethyl)-1,2,4-oxadiazol-5-yl]-5-(4-ethylphenyl)piperidin-1-yl}(1-oxidothiomorpholin-4-yl)methanone [racemic cis isomer]

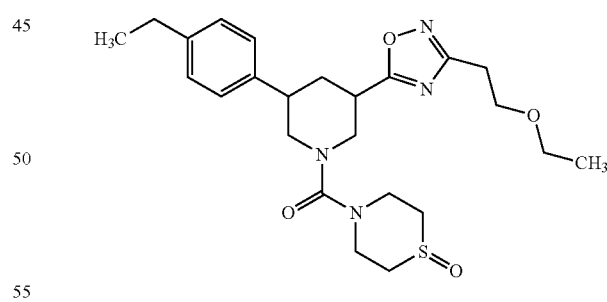

According to General Method 1, 50 mg (0.109 mmol) of the compound from Example 11A were reacted. Yield: 17 mg (32% of theory)

LC-MS (Method 5B): $R_t$=1.01 min; MS (ESIpos): m/z=475 [M+H]$^+$;

$^1$H NMR (400 MHz, DMSO-d$_6$): δ=7.23 (d, 2H), 7.17 (d, 2H), 3.98 (d, 2H), 3.71 (t, 2H), 3.67-3.47 (m, 4H), 3.43 (q, 1H), 3.07-2.89 (m, 3H), 2.75-2.66 (m, 3H), 2.57 (q, 3H), 1.95 (q, 1H), 1.24 (br s, 1H), 1.16 (t, 3H), 1.07 (t, 3H).

Example 5

{3-[3-(2-Ethoxyethyl)-1,2,4-oxadiazol-5-yl]-5-(4-ethylphenyl)piperidin-1-yl}(1-oxidothiomorpholin-4-yl)methanone [enantiomerically pure cis isomer]

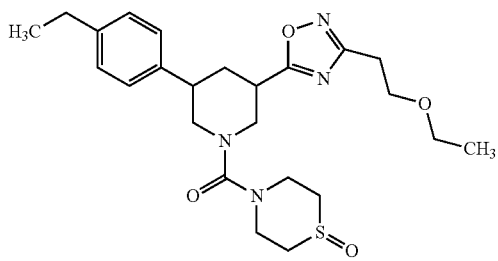 [SMILES: CCOCCc1noc(C2CC(c3ccc(CC)cc3)CN(C(=O)N3CCS(=O)CC3)C2)n1]

Enantiomer separation of the racemate from Example 4 according to Method 6D gave 37.7 mg of the title compound from Example 5 and 20.0 mg of the title compound from Example 6.

LC-MS (Method 5B): $R_t$=1.01 min; MS (ESIpos): m/z=475 [M+H]$^+$;

HPLC (Method 1E): $R_t$=6.48 min, >99.5% ee;

$^1$H NMR (400 MHz, DMSO-d$_6$): δ=7.23 (d, 2H), 7.17 (d, 2H), 3.98 (d, 2H), 3.71 (t, 2H), 3.67-3.47 (m, 4H), 3.43 (q, 1H), 3.07-2.89 (m, 3H), 2.75-2.66 (m, 3H), 2.57 (q, 3H), 1.95 (q, 1H), 1.24 (br s, 1H), 1.16 (t, 3H), 1.07 (t, 3H).

Example 6

{3-[3-(2-Ethoxyethyl)-1,2,4-oxadiazol-5-yl]-5-(4-ethylphenyl)piperidin-1-yl}(1-oxidothiomorpholin-4-yl)methanone [enantiomerically pure cis isomer]

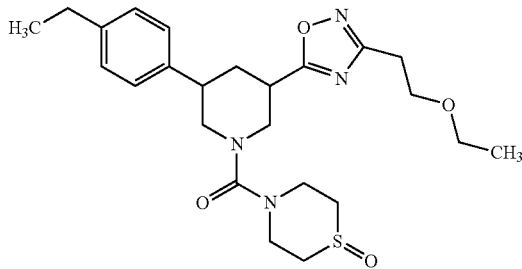 [SMILES: CCOCCc1noc(C2CC(c3ccc(CC)cc3)CN(C(=O)N3CCS(=O)CC3)C2)n1]

Enantiomer separation of the racemate from Example 4 according to Method 6D gave 37.7 mg of the title compound from Example 5 and 20.0 mg of the title compound from Example 6.

LC-MS (Method 5B): $R_t$=1.01 min; MS (ESIpos): m/z=475 [M+H]$^+$;

HPLC (Method 1E): $R_t$=7.27 min, >99.5% ee;

$^1$H NMR (400 MHz, DMSO-d$_6$): δ=7.23 (d, 2H), 7.17 (d, 2H), 3.98 (d, 2H), 3.71 (t, 2H), 3.67-3.47 (m, 4H), 3.43 (q, 1H), 3.07-2.89 (m, 3H), 2.75-2.66 (m, 3H), 2.57 (q, 3H), 1.95 (q, 1H), 1.24 (br s, 1H), 1.16 (t, 3H), 1.07 (t, 3H).

Example 7

{3-[3-(2-Hydroxyethyl)-1,2,4-oxadiazol-5-yl]-5-[4-(trifluoromethyl)phenyl]piperidin-1-yl}(1-oxidothiomorpholin-4-yl)methanone [racemic cis isomer]

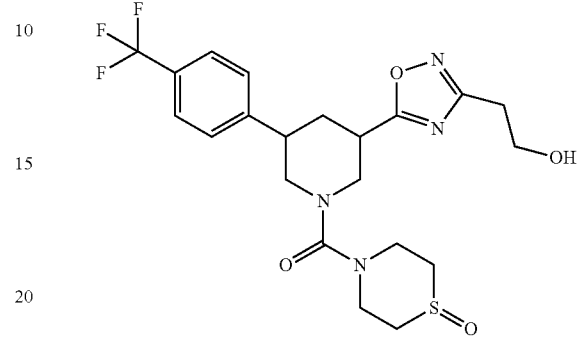

According to General Method 1, 80 mg (0.170 mmol) of the compound from Example 20A were reacted. Yield: 77 mg (91% of theory)

LC-MS (Method 5B): $R_t$=0.85 min; MS (ESIpos): m/z=487 [M+H]$^+$;

$^1$H NMR (400 MHz, DMSO-d$_6$): δ=7.70 (d, 2H), 7.58 (d, 2H), 4.77 (t, 1H), 3.99 (d, 1H), 3.74 (q, 2H), 3.68-3.59 (m, 3H), 3.57-3.48 (m, 2H), 3.48-3.38 (m, 1H), 3.12-3.01 (m, 3H), 2.98-2.86 (m 2H), 2.85-2.80 (m, 2H), 1.55 (q, 1H).

Example 8

(1,1-Dioxidothiomorpholin-4-yl){3-[3-(2-methoxyethyl)-1,2,4-oxadiazol-5-yl]-5-[4-(trifluoromethoxy)phenyl]piperidin-1-yl}methanone [enantiomerically pure cis isomer]

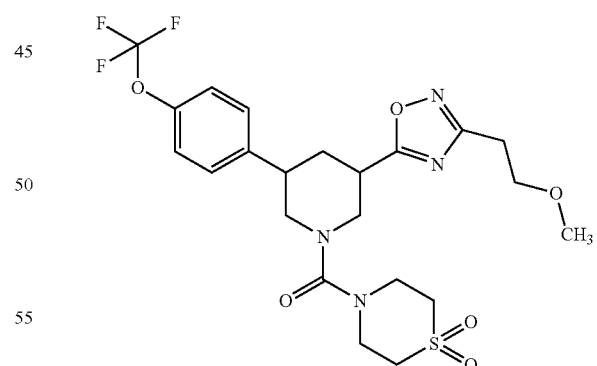

According to General Method 2, 150 mg (0.300 mmol) of the compound from Example 26A were reacted. Enantiomer separation of the racemate according to Method 1D gave 65.0 mg of the title compound from Example 8 and 72.0 mg of the title compound from Example 9.

LC-MS (Method 5B): $R_t$=1.04 min; MS (ESIpos): m/z=533 [M+H]$^+$;

HPLC (Method 2E): $R_t$=15.64 min, >99.5% ee;

¹H NMR (400 MHz, DMSO-d₆): δ=7.48 (d, 2H), 7.33 (d, 2H), 4.03 (d, 1H), 3.70-3.58 (m, 7H), 3.45-3.35 (m, 1H), 3.23 (s, 3H), 3.21-3.15 (m, 4H), 3.12-2.90 (m, 5H), 2.33 (d, 1 H), 1.97 (q, 1 H).

Example 9

(1,1-Dioxidothiomorpholin-4-yl){3-[3-(2-methoxyethyl)-1,2,4-oxadiazol-5-yl]-5-[4-(trifluoromethoxy)phenyl]piperidin-1-yl}methanone [enantiomerically pure cis isomer]

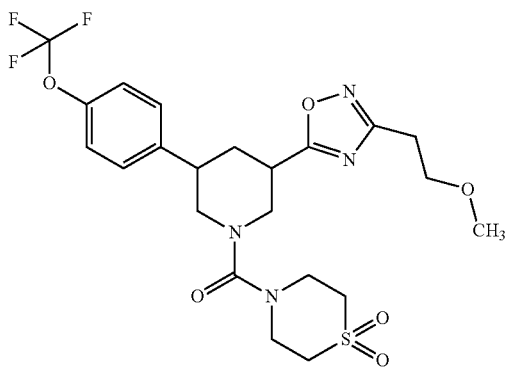 [SMILES: COCCc1noc(C2CC(c3ccc(OC(F)(F)F)cc3)CN(C(=O)N3CCS(=O)(=O)CC3)C2)n1]

According to General Method 2, 150 mg (0.300 mmol) of the compound from Example 26A were reacted. Enantiomer separation of the racemate according to Method 1D gave 65.0 mg of the title compound from Example 8 and 72.0 mg of the title compound from Example 9.

LC-MS (Method 5B): R$_t$=1.04 min; MS (ESIpos): m/z=533 [M+H]⁺;

HPLC (Method 2E): R$_t$=42.42 min, >99.5% ee;

¹H NMR (400 MHz, DMSO-d₆): δ=7.48 (d, 2H), 7.33 (d, 2H), 4.03 (d, 1H), 3.70-3.58 (m, 7H), 3.45-3.35 (m, 1H), 3.23 (s, 3H), 3.21-3.15 (m, 4H), 3.12-2.90 (m, 5H), 2.33 (d, 1 H), 1.97 (q, 1 H).

Example 10

{3-(3-Cyclopropyl-1,2,4-oxadiazol-5-yl)-5-[4-(trifluoromethoxy)phenyl]piperidin-1-yl}(1,1-dioxidothiomorpholin-4-yl)methanone [enantiomerically pure cis isomer]

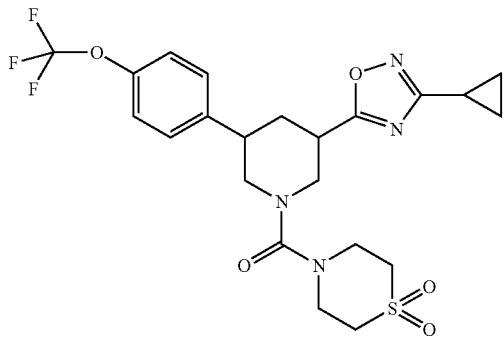 [SMILES: O=C(N1CCS(=O)(=O)CC1)N1CC(c2ccc(OC(F)(F)F)cc2)CC(c2nc(C3CC3)no2)C1]

136 mg (0.281 mmol) of {3-(3-cyclopropyl-1,2,4-oxadiazol-5-yl)-5-[4-(trifluoromethoxy)phenyl]-piperidin-1-yl}(thiomorpholin-4-yl)methanone [racemic cis isomer] (Example 27A) in dichloromethane (11.6 ml) were admixed at RT with 243 mg (0.703 mmol) of meta-chloroperbenzoic acid and then stirred for 30 min. The reaction solution was concentrated under reduced pressure, and the residue was taken up in acetonitrile and purified by means of preparative HPLC. Enantiomer separation of 136 mg of the racemate according to Method 2D gave 61.7 mg of the title compound from Example 10 and 59.6 mg of the title compound from Example 11.

LC-MS (Method 5B): R$_t$=1.12 min; MS (ESIpos): m/z=515 [M+H]⁺;

HPLC (Method 3E): R$_t$=4.26 min, >99.05% ee;

¹H NMR (400 MHz, DMSO-d₆): δ=7.47 (d, 2H), 7.33 (d, 2H), 3.99 (d, 1H), 3.67-3.56 (m, 5H), 3.40-3.33 (m, 1H), 3.20-3.14 (m, 4H), 3.08-2.96 (m, 3H), 2.28 (d, 1 H), 2.14-2.06 (m, 1H), 1.94 (q, 1H), 1.08-1.03 (m, 2H), 0.91-0.86 (m, 2H).

Example 11

{3-(3-Cyclopropyl-1,2,4-oxadiazol-5-yl)-5-[4-(trifluoromethoxy)phenyl]piperidin-1-yl}(1,1-dioxidothiomorpholin-4-yl)methanone [enantiomerically pure cis isomer]

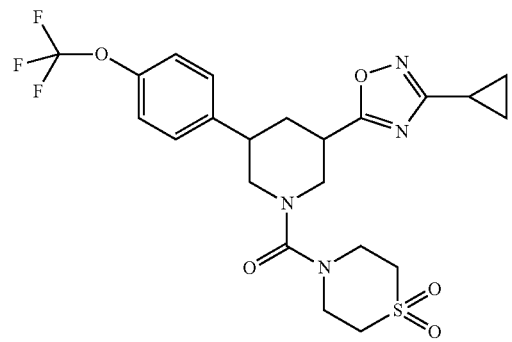 [SMILES: O=C(N1CCS(=O)(=O)CC1)N1CC(c2ccc(OC(F)(F)F)cc2)CC(c2nc(C3CC3)no2)C1]

136 mg (0.281 mmol) of {3-(3-cyclopropyl-1,2,4-oxadiazol-5-yl)-5-[4-(trifluoromethoxy)phenyl]-piperidin-1-yl}(thiomorpholin-4-yl)methanone [racemic cis isomer] (Example 27A) in dichloromethane (11.6 ml) were admixed at RT with 243 mg (0.703 mmol) of meta-chloroperbenzoic acid and then stirred for 30 min. The reaction solution was concentrated under reduced pressure, and the residue was taken up in acetonitrile and purified by means of preparative HPLC. Enantiomer separation of 136 mg of the racemate according to Method 2D gave 61.7 mg of the title compound from Example 10 and 59.6 mg of the title compound from Example 11.

LC-MS (Method 5B): R$_t$=1.12 min; MS (ESIpos): m/z=515 [M+H]⁺;

HPLC (Method 3E): R$_t$=5.68 min, >99.0% ee;

¹H NMR (400 MHz, DMSO-d₆): δ=7.47 (d, 2H), 7.33 (d, 2H), 3.99 (d, 1H), 3.67-3.56 (m, 5H), 3.40-3.33 (m, 1H), 3.20-3.14 (m, 4H), 3.08-2.96 (m, 3H), 2.28 (d, 1 H), 2.14-2.06 (m, 1H), 1.94 (q, 1H), 1.08-1.03 (m, 2H), 0.91-0.86 (m, 2H).

Example 12

(1,1-Dioxidothiomorpholin-4-yl){3-(4-ethylphenyl)-5-[3-(2-methoxyethyl)-1,2,4-oxadiazol-5-yl]-piperidin-1-yl}methanone [enantiomerically pure cis isomer]

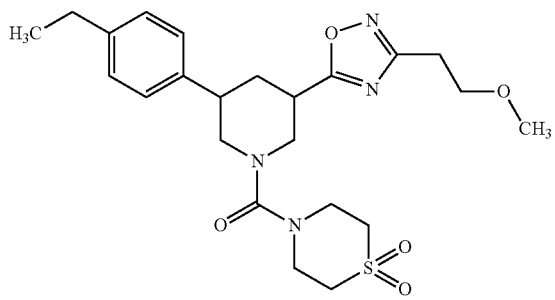 [SMILES: CCc1ccc(C2CC(c3nc(CCOC)no3)CN(C(=O)N3CCS(=O)(=O)CC3)C2)cc1]

According to General Method 2, 77.0 mg (0.173 mmol) of the compound from Example 8A were reacted. Enantiomer separation of 74.9 mg of the racemate according to Method 3D gave 36.0 mg of the title compound from Example 12 and 35.0 mg of the title compound from Example 13.

LC-MS (Method 2B): $R_t$=1.17 min; MS (ESIpos): m/z=477 [M+H]$^+$;

HPLC (Method 4E): $R_t$=5.49 min, >99.0% ee;

$^1$H NMR (400 MHz, DMSO-d$_6$): δ=7.23 (d, 2 H), 7.17 (d, 2 H), 4.03 (d, 1 H), 3.73-3.56 (m, 7 H), 3.46-3.35 (m, 1 H), 3.23 (s, 3 H), 3.17 (br s, 4 H), 3.06 (t, 1 H), 3.01-2.83 (m, 4 H), 2.58 (d, 3 H), 2.30 (d, 1 H), 1.95 (q, 1 H), 1.16 (t, 3 H).

Example 13

(1,1-Dioxidothiomorpholin-4-yl){3-(4-ethylphenyl)-5-[3-(2-methoxyethyl)-1,2,4-oxadiazol-5-yl]-piperidin-1-yl}methanone [enantiomerically pure cis isomer]

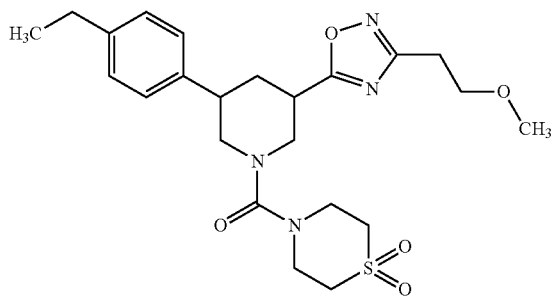 [SMILES: CCc1ccc(C2CC(c3nc(CCOC)no3)CN(C(=O)N3CCS(=O)(=O)CC3)C2)cc1]

According to General Method 2, 77.0 mg (0.173 mmol) of the compound from Example 8A were reacted. Enantiomer separation of 74.9 mg of the racemate according to Method 3D gave 36.0 mg of the title compound from Example 12 and 35.0 mg of the title compound from Example 13.

LC-MS (Method 2B): $R_t$=1.17 min; MS (ESIpos): m/z=477 [M+H]$^+$;

HPLC (Method 4E): $R_t$=12.07 min, >99.0% ee;

$^1$H NMR (400 MHz, DMSO-d$_6$): δ=7.23 (d, 2 H), 7.17 (d, 2 H), 4.03 (d, 1 H), 3.73-3.56 (m, 7 H), 3.46-3.35 (m, 1 H), 3.23 (s, 3 H), 3.17 (br s, 4 H), 3.06 (t, 1 H), 3.01-2.83 (m, 4 H), 2.58 (d, 3 H), 2.30 (d, 1 H), 1.95 (q, 1 H), 1.16 (t, 3 H).

Example 14

[3-(3-Cyclopropyl-1,2,4-oxadiazol-5-yl)-5-(4-ethylphenyl)piperidin-1-yl](1,1-dioxidothiomorpholin-4-yl)methanone [enantiomerically pure cis isomer]

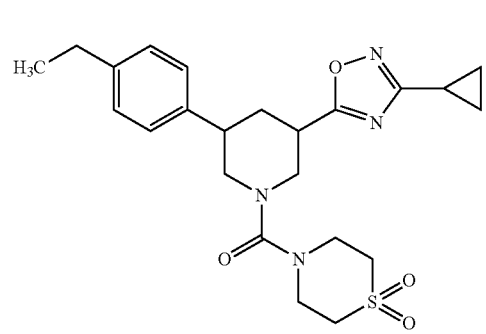 [SMILES: CCc1ccc(C2CC(c3nc(C4CC4)no3)CN(C(=O)N3CCS(=O)(=O)CC3)C2)cc1]

According to General Method 2, 55 mg (0.130 mmol) of the compound from Example 9A were reacted. Enantiomer separation of 53.3 mg of the racemate according to Method 4D gave 23.0 mg of the title compound from Example 14 and 23.0 mg of the title compound from Example 15.

LC-MS (Method 2B): $R_t$=1.30 min; MS (ESIpos): m/z=459 [M+H]$^+$;

HPLC (Method 5E): $R_t$=8.89 min, >99.0% ee;

$^1$H NMR (400 MHz, DMSO-d$_6$): δ=7.23 (d, 2 H), 7.16 (d, 2 H), 3.99 (d, 1 H), 3.67-3.55 (m, 5 H), 3.39-3.32 (m, 1 H), 3.17 (br s, 4 H), 3.07-2.91 (m, 2 H), 2.91-2.81 (m, 1 H), 2.62-2.55 (m, 2 H), 2.26 (d, 1 H), 2.16-2.08 (m, 1 H), 1.91 (q, 1 H), 1.16 (t, 3 H), 1.10-1.02 (m, 2 H), 0.92-0.85 (m, 2 H).

Example 15

[3-(3-Cyclopropyl-1,2,4-oxadiazol-5-yl)-5-(4-ethylphenyl)piperidin-1-yl](1,1-dioxidothiomorpholin-4-yl)methanone [enantiomerically pure cis isomer]

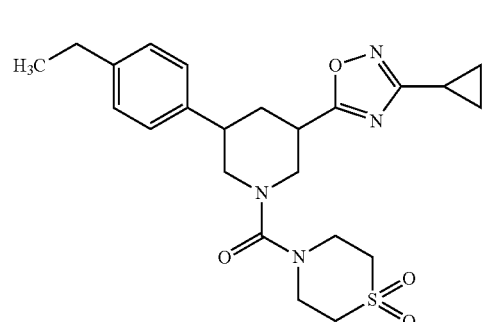

According to General Method 2, 55.5 mg (0.130 mmol) of the compound from Example 9A were reacted. Enantiomer separation of 53.3 mg of the racemate according to Method 4D gave 23.0 mg of the title compound from Example 14 and 23.0 mg of the title compound from Example 15.

LC-MS (Method 2B): $R_t$=1.27 min; MS (ESIpos): m/z=459 [M+H]$^+$;

HPLC (Method 5E): $R_t$=12.06 min, >99.0% ee;

$^1$H NMR (400 MHz, DMSO-d$_6$): δ=7.23 (d, 2 H), 7.16 (d, 2 H), 3.99 (d, 1 H), 3.67-3.55 (m, 5 H), 3.39-3.32 (m, 1 H), 3.17 (br s, 4 H), 3.07-2.91 (m, 2 H), 2.91-2.81 (m, 1 H), 2.62-2.55 (m, 2 H), 2.26 (d, 1 H), 2.16-2.08 (m, 1 H), 1.91 (q, 1 H), 1.16 (t, 3 H), 1.10-1.02 (m, 2 H), 0.92-0.85 (m, 2 H).

Example 16

{3-(3-Cyclopropyl-1,2,4-oxadiazol-5-yl)-5-[4-(trifluoromethyl)phenyl]piperidin-1-yl}(1,1-dioxidothiomorpholin-4-yl)methanone [enantiomerically pure cis isomer]

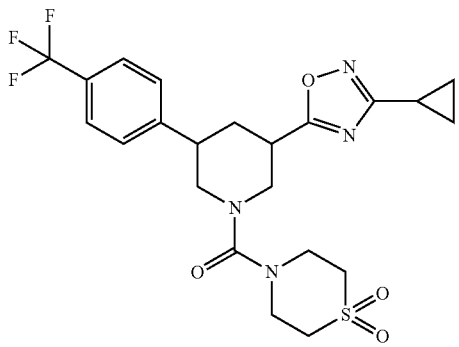 [SMILES: O=C(N1CCS(=O)(=O)CC1)N1CC(c2ccc(C(F)(F)F)cc2)CC(c2nc(C3CC3)no2)C1]

According to General Method 2, 269 mg (0.578 mmol) of the compound from Example 17A were reacted. Enantiomer separation of 292 mg of the racemate according to Method 1D gave 57.8 mg of the title compound from Example 16 and 99.7 mg of the title compound from Example 17.

LC-MS (Method 2B): R$_t$=1.26 min; MS (ESIpos): m/z=499 [M+H]$^+$;

HPLC (Method 1E): R$_t$=10.53 min, >99.0% ee;

$^1$H NMR (400 MHz, DMSO-d$_6$): δ=7.70 (d, 2 H), 7.57 (d, 2 H), 4.00 (d, 1 H), 3.67 (d, 1 H), 3.61 (br s, 4 H), 3.44-3.33 (m, 1 H), 3.17 (br s, 4 H), 3.12-2.98 (m, 3 H), 2.31 (d, 1 H), 2.11 (dt, 1 H), 1.98 (q, 1 H), 1.12-1.00 (m, 2 H), 0.95-0.84 (m, 2 H).

Example 17

{3-(3-Cyclopropyl-1,2,4-oxadiazol-5-yl)-5-[4-(trifluoromethyl)phenyl]piperidin-1-yl}(1,1-dioxidothiomorpholin-4-yl)methanone [enantiomerically pure cis isomer]

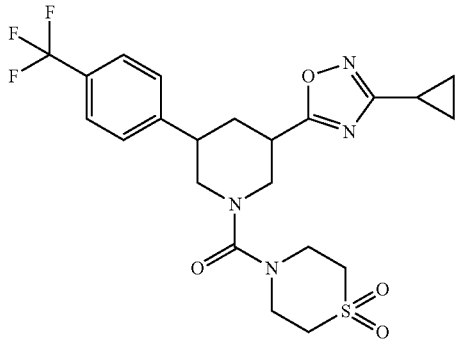 [SMILES: O=C(N1CCS(=O)(=O)CC1)N1CC(c2ccc(C(F)(F)F)cc2)CC(c2nc(C3CC3)no2)C1]

According to General Method 2, 269 mg (0.578 mmol) of the compound from Example 17A were reacted. Enantiomer separation of 292 mg of the racemate according to Method 1D gave 57.8 mg of the title compound from Example 16 and 99.7 mg of the title compound from Example 17.

LC-MS (Method 2B): R$_t$=1.26 min; MS (ESIpos): m/z=499 [M+H]$^+$;

HPLC (Method 1E): R$_t$=16.04 min, >99.0% ee;

$^1$H NMR (400 MHz, DMSO-d$_6$): δ=7.70 (d, 2 H), 7.57 (d, 2 H), 4.00 (d, 1 H), 3.67 (d, 1 H), 3.61 (br s, 4 H), 3.44-3.33 (m, 1 H), 3.17 (br s, 4 H), 3.12-2.98 (m, 3 H), 2.31 (d, 1 H), 2.11 (dt, 1 H), 1.98 (q, 1 H), 1.12-1.00 (m, 2 H), 0.95-0.84 (m, 2 H).

Example 18

(1,1-Dioxidothiomorpholin-4-yl){3-[3-(2-ethoxyethyl)-1,2,4-oxadiazol-5-yl]-5-[4-(trifluoromethoxy)phenyl]piperidin-1-yl}methanone [enantiomerically pure cis isomer]

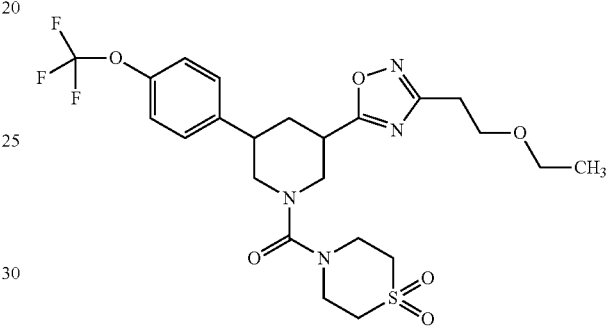

According to General Method 2, 317 mg (0.616 mmol) of the compound from Example 28A were reacted. Enantiomer separation of 294 mg of the racemate according to Method 2D gave 132 mg of the title compound from Example 18 and 129 mg of the title compound from Example 19.

LC-MS (Method 6B): R$_t$=2.34 min; MS (ESIpos): m/z=547 [M+H]$^+$;

HPLC (Method 3E): R$_t$=4.60 min, >99.0% ee;

$^1$H NMR (400 MHz, DMSO-d$_6$): δ=7.48 (d, 2 H), 7.33 (d, 2 H), 4.03 (d, 1 H), 3.71 (t, 2 H), 3.68-3.56 (m, 5 H), 3.43 (q, 3 H), 3.17 (br s, 4 H), 3.07 (t, 1 H), 3.01 (d, 2 H), 2.93 (t, 2 H), 2.32 (d, 1 H), 2.05-1.91 (m, 1 H), 1.07 (t, 3 H).

Example 19

(1,1-Dioxidothiomorpholin-4-yl){3-[3-(2-ethoxyethyl)-1,2,4-oxadiazol-5-yl]-5-[4-(trifluoromethoxy)phenyl]piperidin-1-yl}methanone [enantiomerically pure cis isomer]

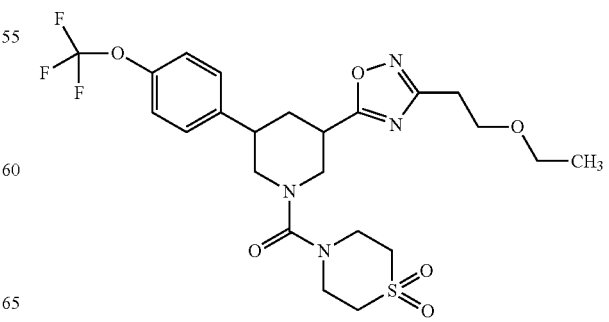

According to General Method 2, 317 mg (0.616 mmol) of the compound from Example 28A were reacted. Enantiomer separation of 294 mg of the racemate according to Method 2D gave 132 mg of the title compound from Example 18 and 129 mg of the title compound from Example 19.

LC-MS (Method 6B): $R_t$=2.34 min; MS (ESIpos): m/z=547 [M+H]$^+$;

HPLC (Method 3E): $R_t$=11.53 min, >99.0% ee;

$^1$H NMR (400 MHz, DMSO-$d_6$): δ=7.48 (d, 2 H), 7.33 (d, 2 H), 4.03 (d, 1 H), 3.71 (t, 2 H), 3.68-3.56 (m, 5 H), 3.43 (q, 3 H), 3.17 (br s, 4 H), 3.07 (t, 1 H), 3.01 (d, 2 H), 2.93 (t, 2 H), 2.32 (d, 1 H), 2.05-1.91 (m, 1 H), 1.07 (t, 3 H).

Example 20

{3-(3-Cyclopropyl-1,2,4-oxadiazol-5-yl)-5-[4-(trifluoromethyl)phenyl]piperidin-1-yl}(1-oxidothiomorpholin-4-yl)methanone [racemic cis isomer]

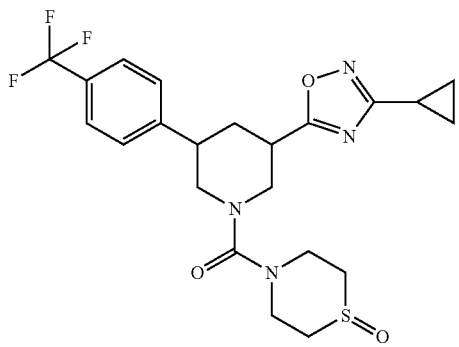 [SMILES: O=C(N1CCS(=O)CC1)N1CC(c2ccc(C(F)(F)F)cc2)CC(c2nc(C3CC3)no2)C1]

According to General Method 1, 50.0 mg (0.107 mmol) of the compound from Example 17A were reacted. Yield: 4.3 mg (8% of theory)

LC-MS (Method 5B): $R_t$=1.05 min; MS (ESIpos): m/z=483 [M+H]$^+$.

Example 21

{3-[3-(2-Hydroxyethyl)-1,2,4-oxadiazol-5-yl]-5-[4-(trifluoromethoxy)phenyl]piperidin-1-yl}-(1-oxidothiomorpholin-4-yl)methanone [racemic cis isomer]

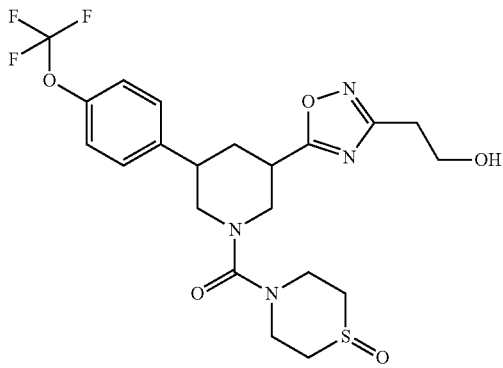 [SMILES: O=C(N1CCS(=O)CC1)N1CC(c2ccc(OC(F)(F)F)cc2)CC(c2nc(CCO)no2)C1]

According to General Method 1, 100.0 mg (0.206 mmol) of the compound from Example 29A were reacted. Yield: 105.2 mg (99% of theory)

LC-MS (Method 5B): $R_t$=0.89 min; MS (ESIpos): m/z=503 [M+H]$^+$.

Example 22

{3-[3-(2-Ethoxyethyl)-1,2,4-oxadiazol-5-yl]-5-[4-(trifluoromethyl)phenyl]piperidin-1-yl}(1-oxidothiomorpholin-4-yl)methanone [racemic cis isomer]

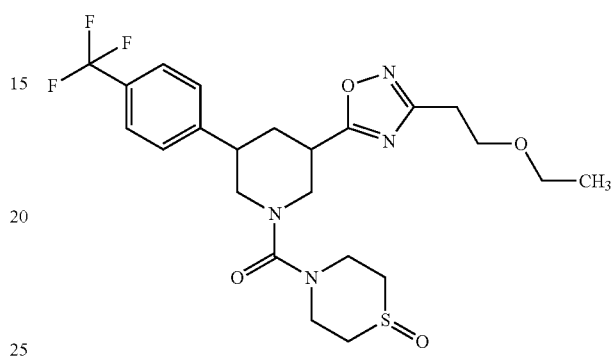

According to General Method 1, 50.0 mg (0.100 mmol) of the compound from Example 19A were reacted. Yield: 50.2 mg (92% of theory)

LC-MS (Method 5B): $R_t$=1.02 min; MS (ESIpos): m/z=515 [M+H]$^+$;

Example 23

{3-[3-(2-Ethoxyethyl)-1,2,4-oxadiazol-5-yl]-5-[4-(trifluoromethyl)phenyl]piperidin-1-yl}(1-oxidothiomorpholin-4-yl)methanone [enantiomerically pure cis isomer]

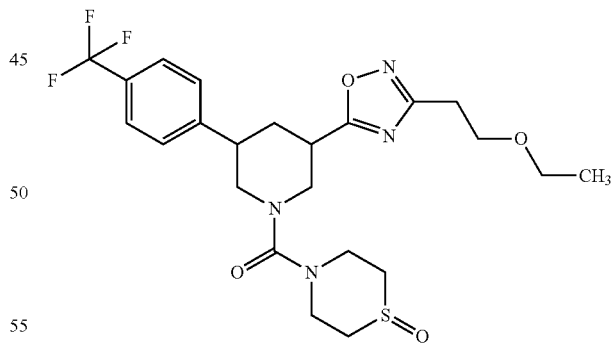

Enantiomer separation of 50.2 mg of the racemate from Example 22 according to Method 1D gave 25.5 mg of the title compound from Example 23 and 22.4 mg of the title compound from Example 24.

LC-MS (Method 2B): $R_t$=1.14 min; MS (ESIpos): m/z=515 [M+H]$^+$;

HPLC (Method 2E): $R_t$=7.51 min, >99.0% ee;

$^1$H NMR (400 MHz, DMSO-$d_6$): δ=7.70 (d, 2 H), 7.58 (d, 2 H), 4.00 (d, 1 H), 3.71 (t, 2 H), 3.63 (d, 3 H), 3.57-3.48 (m,

2 H), 3.43 (q, 3 H), 3.14-3.00 (m, 3 H), 2.93 (t, 4 H), 2.77-2.65 (m, 2 H), 2.35 (d, 1 H), 2.10-1.95 (m, 1 H), 1.06 (m, 3 H).

Example 24

{3-[3-(2-Ethoxyethyl)-1,2,4-oxadiazol-5-yl]-5-[4-(trifluoromethyl)phenyl]piperidin-1-yl}(1-oxidothio-morpholin-4-yl)methanone [enantiomerically pure cis isomer]

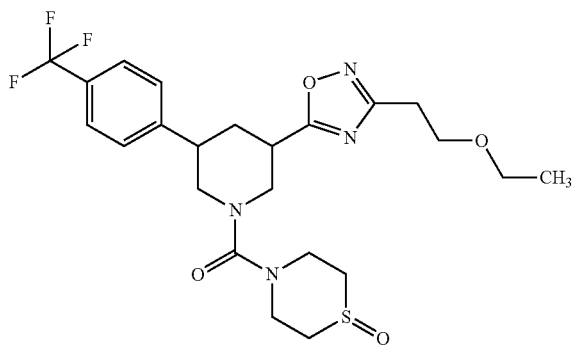 [SMILES: CCOCCc1noc(C2CC(c3ccc(C(F)(F)F)cc3)CN(C(=O)N3CCS(=O)CC3)C2)n1]

Enantiomer separation of 50.2 mg of the racemate from Example 22 according to Method 1D gave 25.5 mg of the title compound from Example 23 and 22.4 mg of the title compound from Example 24.

LC-MS (Method 2B): $R_t$=1.14 min; MS (ESIpos): m/z=515 [M+H]$^+$;

HPLC (Method 2E): $R_t$=13.93 min, >99.0% ee;

$^1$H NMR (400 MHz, DMSO-$d_6$): δ=7.70 (d, 2 H), 7.58 (d, 2 H), 4.00 (d, 1 H), 3.71 (t, 2 H), 3.63 (d, 3 H), 3.57-3.48 (m, 2 H), 3.43 (q, 3 H), 3.14-3.00 (m, 3 H), 2.93 (t, 4 H), 2.77-2.65 (m, 2 H), 2.35 (d, 1 H), 2.10-1.95 (m, 1 H), 1.06 (m, 3 H).

Example 25

{3-(4-Ethylphenyl)-5-[3-(2-methoxyethyl)-1,2,4-oxadiazol-5-yl]piperidin-1-yl}(1-oxidothio-morpholin-4-yl)methanone [racemic cis isomer]

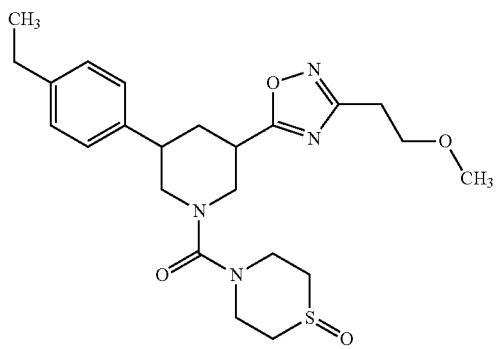 [SMILES: CCc1ccc(C2CC(c3nc(CCOC)no3)CN(C(=O)N3CCS(=O)CC3)C2)cc1]

According to General Method 1, 77.0 mg (0.173 mmol) of the compound from Example 8A were reacted. Yield: 63.2 mg (79% of theory)

LC-MS (Method 5B): $R_t$=0.97 min; MS (ESIpos): m/z=461 [M+H]$^+$;

$^1$H NMR (400 MHz, DMSO-$d_6$): δ=7.23 (m, 2 H), 7.17 (m, 2 H), 3.99 (d, 1 H), 3.72-3.46 (m, 7 H), 3.46-3.34 (m, 2 H), 3.09-2.98 (m, 1 H), 2.97-2.83 (m, 6 H), 2.65 (br s, 1 H), 2.76-2.64 (m, 2 H), 2.58 (d, 3 H), 2.30 (d, 1 H), 1.95 (q, 1 H), 1.16 (t, 3 H); one proton hidden.

Example 26

{3-(4-Ethylphenyl)-5-[3-(2-methoxyethyl)-1,2,4-oxadiazol-5-yl]piperidin-1-yl}(1-oxidothio-morpholin-4-yl)methanone [enantiomerically pure cis isomer]

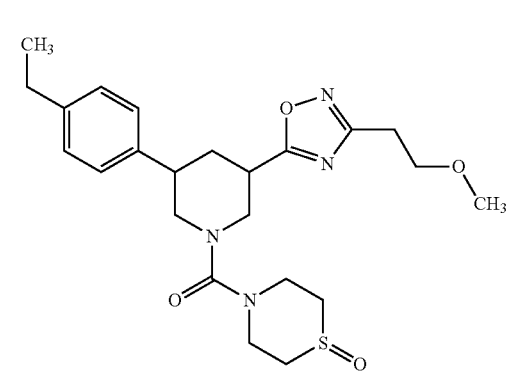 [SMILES: CCc1ccc(C2CC(c3nc(CCOC)no3)CN(C(=O)N3CCS(=O)CC3)C2)cc1]

Enantiomer separation of 63.2 mg of the racemate from Example 25 according to Method 6D gave 17.8 mg of the title compound from Example 26 and 18.7 mg of the title compound from Example 27.

LC-MS (Method 5B): $R_t$=0.97 min; MS (ESIpos): m/z=461 [M+H]$^+$;

HPLC (Method 2E): $R_t$=6.48 min, >99.0% ee;

$^1$H NMR (400 MHz, DMSO-$d_6$): δ=7.23 (m, 2 H), 7.17 (m, 2 H), 3.99 (d, 1 H), 3.72-3.46 (m, 7 H), 3.46-3.34 (m, 2 H), 3.09-2.98 (m, 1 H), 2.97-2.83 (m, 6 H), 2.65 (br s, 1 H), 2.76-2.64 (m, 2 H), 2.58 (d, 3 H), 2.30 (d, 1 H), 1.95 (q, 1 H), 1.16 (t, 3 H); one proton hidden.

Example 27

{3-(4-Ethylphenyl)-5-[3-(2-methoxyethyl)-1,2,4-oxadiazol-5-yl]piperidin-1-yl}(1-oxidothio-morpholin-4-yl)methanone [enantiomerically pure cis isomer]

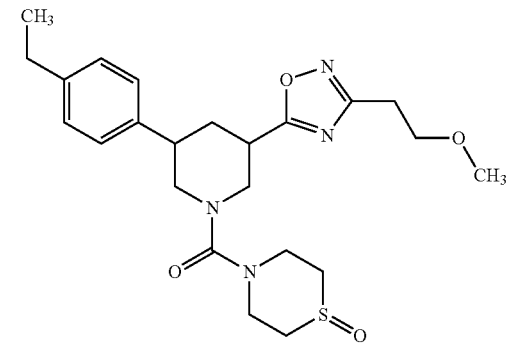 [SMILES: CCc1ccc(C2CC(c3nc(CCOC)no3)CN(C(=O)N3CCS(=O)CC3)C2)cc1]

Enantiomer separation of 63.2 mg of the racemate from Example 25 according to Method 6D gave 17.8 mg of the title compound from Example 26 and 18.7 mg of the title compound from Example 27.

LC-MS (Method 5B): R$_t$=0.97 min; MS (ESIpos): m/z=461 [M+H]$^+$;

HPLC (Method 2E): R$_t$=7.97 min, >99.0% ee;

$^1$H NMR (400 MHz, DMSO-d$_6$): δ=7.23 (m, 2 H), 7.17 (m, 2 H), 3.99 (d, 1 H), 3.72-3.46 (m, 7 H), 3.46-3.34 (m, 2 H), 3.09-2.98 (m, 1 H), 2.97-2.83 (m, 6 H), 2.65 (br s, 1 H), 2.76-2.64 (m, 2 H), 2.58 (d, 3 H), 2.30 (d, 1 H), 1.95 (q, 1 H), 1.16 (t, 3 H); one proton hidden.

Example 28

(1,1-Dioxidothiomorpholin-4-yl){3-[3-(2-methoxyethyl)-1,2,4-oxadiazol-5-yl]-5-[4-(trifluoromethyl)phenyl]piperidin-1-yl}methanone [enantiomerically pure cis isomer]

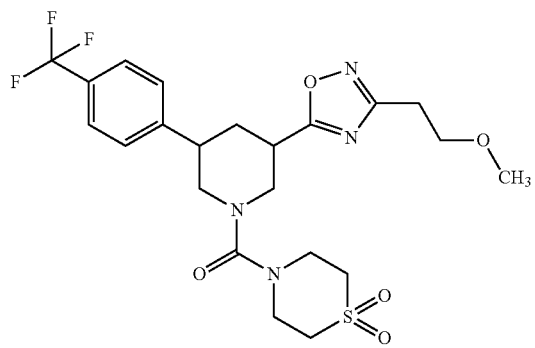 [SMILES: COCCc1noc(C2CC(c3ccc(C(F)(F)F)cc3)CN(C(=O)N3CCS(=O)(=O)CC3)C2)n1]

According to General Method 2, 269 mg (0.556 mmol) of the compound from Example 18A were reacted. Enantiomer separation of the racemate according to Method 5D gave 126 mg of the title compound from Example 28 and 122 mg of the title compound from Example 29.

LC-MS (Method 6B): R$_t$=2.18 min; MS (ESIpos): m/z=517 [M+H]$^+$;

HPLC (Method 2E): R$_t$=4.98 min, >99.0% ee;

$^1$H NMR (400 MHz, DMSO-d$_6$): δ=7.70 (d, 2 H), 7.58 (d, 2 H), 4.03 (d, 1 H), 3.68 (t, 3 H), 3.62 (br s, 4H), 3.49-3.38 (m, 1 H), 3.23 (s, 3 H), 3.18 (br s, 4 H), 3.14-3.02 (m, 3 H), 2.94 (t, 2 H), 2.35 (d, 1 H), 2.02 (d, 1 H).

Example 29

(1,1-Dioxidothiomorpholin-4-yl){3-[3-(2-methoxyethyl)-1,2,4-oxadiazol-5-yl]-5-[4-(trifluoromethyl)phenyl]piperidin-1-yl}methanone [enantiomerically pure cis isomer]

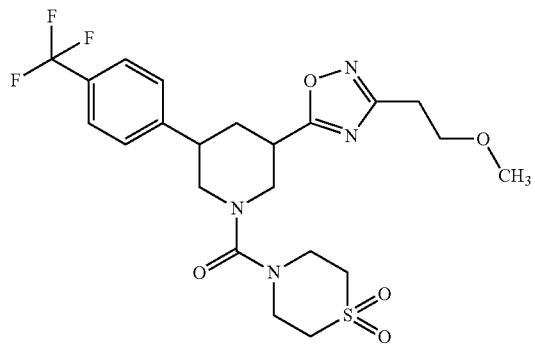 [SMILES: COCCc1noc(C2CC(c3ccc(C(F)(F)F)cc3)CN(C(=O)N3CCS(=O)(=O)CC3)C2)n1]

According to General Method 2, 269 mg (0.556 mmol) of the compound from Example 18A were reacted. Enantiomer separation of the racemate according to Method 5D gave 126 mg of the title compound from Example 28 and 122 mg of the title compound from Example 29.

LC-MS (Method 6B): R$_t$=2.18 min; MS (ESIpos): m/z=517 [M+H]$^+$;

HPLC (Method 2E): R$_t$=15.96 min, >99.0% ee;

$^1$H NMR (400 MHz, DMSO-d$_6$): δ=7.70 (d, 2 H), 7.58 (d, 2 H), 4.03 (d, 1 H), 3.68 (t, 3 H), 3.62 (br s, 4H), 3.49-3.38 (m, 1H), 3.23 (s, 3H), 3.18 (br s, 4 H), 3.14-3.02 (m, 3 H), 2.94 (t, 2 H), 2.35 (d, 1 H), 2.02 (d, 1 H).

Example 30

(1,1-Dioxidothiomorpholin-4-yl){3-[3-(2-ethoxyethyl)-1,2,4-oxadiazol-5-yl]-5-[4-(trifluoromethyl)phenyl]piperidin-1-yl}methanone [enantiomerically pure cis isomer]

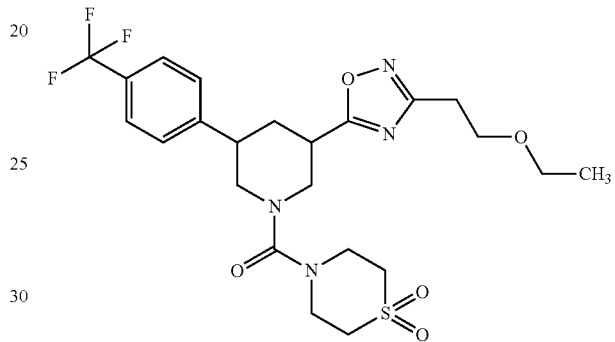

According to General Method 2, 259 mg (0.519 mmol) of the compound from Example 19A were reacted. Enantiomer separation of 252 mg of the racemate according to Method 2D gave 104 mg of the title compound from Example 30 and 91.0 mg of the title compound from Example 31.

LC-MS (Method 6B): R$_t$=2.29 min; MS (ESIpos): m/z=531 [M+H]$^+$;

HPLC (Method 3E): R$_t$=4.92 min, >99.0% ee;

$^1$H NMR (400 MHz, DMSO-d$_6$): δ=7.71 (d, 2 H), 7.58 (d, 2H), 4.03 (d, 1 H), 3.75-3.68 (m, 3 H), 3.62 (br s, 4 H), 3.43 (q, 3 H), 3.18 (br s, 4 H), 3.14-3.01 (m, 3 H), 2.93 (t, 2 H), 2.35 (d, 1 H), 2.12-1.95 (m, 1 H), 1.07 (t, 3 H).

Example 31

(1,1-Dioxidothiomorpholin-4-yl){3-[3-(2-ethoxyethyl)-1,2,4-oxadiazol-5-yl]-5-[4-(trifluoromethyl)phenyl]piperidin-1-yl}methanone [enantiomerically pure cis isomer]

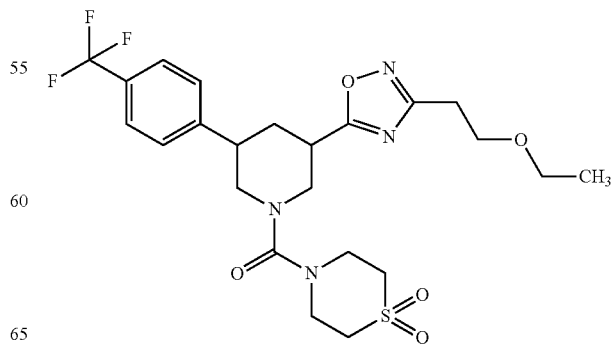

According to General Method 2, 259 mg (0.519 mmol) of the compound from Example 19A were reacted. Enantiomer separation of 252 mg of the racemate according to Method 2D gave 104 mg of the title compound from Example 30 and 91.0 mg of the title compound from Example 31.

LC-MS (Method 6B): $R_t$=2.29 min; MS (ESIpos): m/z=531 [M+H]$^+$;

HPLC (Method 3E): $R_t$=13.63 min, >99.0% ee;

$^1$H NMR (400 MHz, DMSO-$d_6$): δ=7.71 (d, 2 H), 7.58 (d, 2 H), 4.03 (d, 1 H), 3.75-3.68 (m, 3 H), 3.62 (br s, 4 H), 3.43 (q, 3 H), 3.18 (br s, 4 H), 3.14-3.01 (m, 3 H), 2.93 (t, 2 H), 2.35 (d, 1 H), 2.12-1.95 (m, 1 H), 1.07 (t, 3 H).

Example 32

(1,1-Dioxidothiomorpholin-4-yl){3-[3-(2-hydroxyethyl)-1,2,4-oxadiazol-5-yl]-5-[4-(trifluoromethyl)phenyl]piperidin-1-yl}methanone [enantiomerically pure cis isomer]

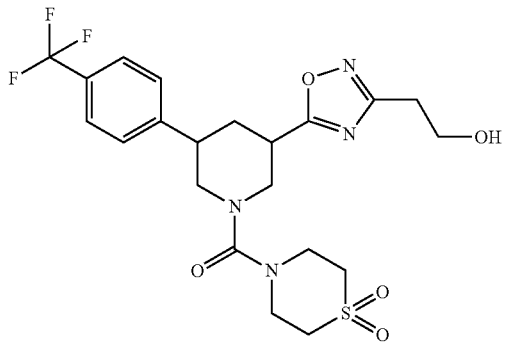 [SMILES: O=C(N1CCS(=O)(=O)CC1)N1CC(c2ccc(C(F)(F)F)cc2)CC(c2nc(CCO)no2)C1]

According to General Method 2, 100 mg (0.213 mmol) of the compound from Example 20A were reacted. Enantiomer separation of 97.4 mg of the racemate according to Method 2D gave 33.9 mg of the title compound from Example 32 and 35.0 mg of the title compound from Example 33.

LC-MS (Method 5B): $R_t$=0.91 min; MS (ESIpos): m/z=503 [M+H]$^+$;

HPLC (Method 3E): $R_t$=4.75 min, >99.0% ee;

$^1$H NMR (400 MHz, DMSO-$d_6$): δ=7.71 (d, 2 H), 7.58 (d, 2 H), 4.77 (t, 1 H), 4.03 (d, 1 H), 3.74 (q, 2 H), 3.68 (d, 1 H), 3.62 (br s, 4 H), 3.47-3.37 (m, 1 H), 3.18 (br s, 4 H), 3.13-3.00 (m, 3 H), 2.82 (t, 2 -H), 2.35 (d, 1 H), 2.10-1.94 (m, 1 H).

Example 33

(1,1-Dioxidothiomorpholin-4-yl){3-[3-(2-hydroxyethyl)-1,2,4-oxadiazol-5-yl]-5-[4-(trifluoromethyl)phenyl]piperidin-1-yl}methanone [enantiomerically pure cis isomer]

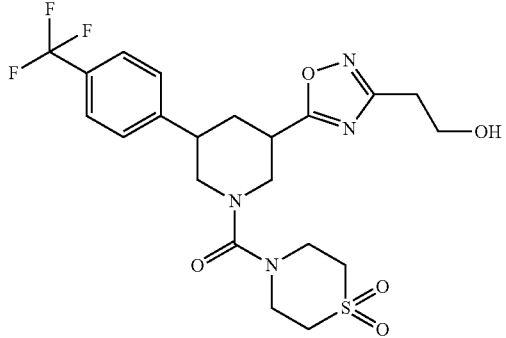 [SMILES: O=C(N1CCS(=O)(=O)CC1)N1CC(c2ccc(C(F)(F)F)cc2)CC(c2nc(CCO)no2)C1]

According to General Method 2, 100 mg (0.213 mmol) of the compound from Example 20A were reacted. Enantiomer separation of 97.4 mg of the racemate according to Method 2D gave 33.9 mg of the title compound from Example 32 and 35.0 mg of the title compound from Example 33.

LC-MS (Method 5B): $R_t$=0.91 min; MS (ESIpos): m/z=503 [M+H]$^+$;

HPLC (Method 3E): $R_t$=8.97 min, >99.0% ee;

$^1$H NMR (400 MHz, DMSO-$d_6$): δ=7.71 (d, 2 H), 7.58 (d, 2 H), 4.77 (t, 1 H), 4.03 (d, 1 H), 3.74 (q, 2 H), 3.68 (d, 1 H), 3.62 (br s, 4 H), 3.47-3.37 (m, 1 H), 3.18 (br s, 4 H), 3.13-3.00 (m, 3 H), 2.82 (t, 2 -H), 2.35 (d, 1 H), 2.10-1.94 (m, 1 H).

Example 34

(1,1-Dioxidothiomorpholin-4-yl){3-[3-(2-ethoxyethyl)-1,2,4-oxadiazol-5-yl]-5-(4-ethylphenyl)-piperidin-1-yl}methanone [enantiomerically pure cis isomer]

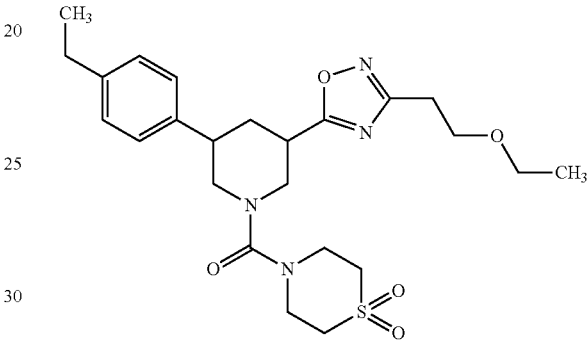

According to General Method 2, 303 mg (0.661 mmol) of the compound from Example 11A were reacted. Enantiomer separation of 297 mg of the racemate according to Method 2D gave 139 mg of the title compound from Example 34 and 117 mg of the title compound from Example 35.

LC-MS (Method 2B): $R_t$=1.24 min; MS (ESIpos): m/z=491 [M+H]$^+$;

HPLC (Method 3E): $R_t$=4.81 min, >99.0% ee;

$^1$H NMR (400 MHz, DMSO-$d_6$): δ=7.24 (m, 2 H), 7.17 (m, 2 H), 4.03 (d, 1 H), 3.71 (t, 2 H), 3.67-3.57 (m, 5 H), 3.49-3.35 (m, 3 H), 3.17 (br s, 4 H), 3.06 (t, 1 H), 2.98-2.86 (m, 3 H), 2.62-2.55 (m, 3 H), 2.30 (d, 2 H), 1.95 (q, 1 H), 1.16 (t, 3 H), 1.07 (t, 3 H).

Example 35

(1,1-Dioxidothiomorpholin-4-yl){3-[3-(2-ethoxyethyl)-1,2,4-oxadiazol-5-yl]-5-(4-ethylphenyl)-piperidin-1-yl}methanone [enantiomerically pure cis isomer]

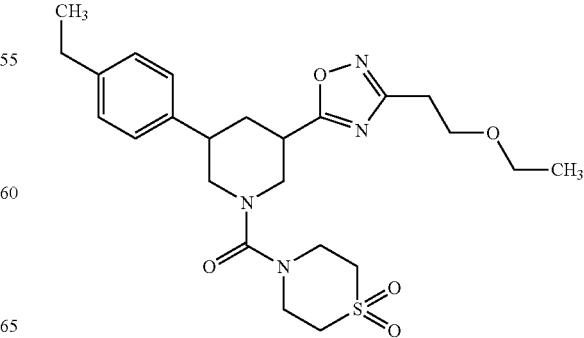

According to General Method 2, 303 mg (0.661 mmol) of the compound from Example 11A were reacted. Enantiomer separation of 297 mg of the racemate according to Method 2D gave 139 mg of the title compound from Example 34 and 117 mg of the title compound from Example 35.

LC-MS (Method 2B): $R_t$=1.24 min; MS (ESIpos): m/z=491 [M+H]$^+$;

HPLC (Method 3E): $R_t$=6.80 min, >99.0% ee;

$^1$H NMR (400 MHz, DMSO-d$_6$): δ=7.24 (m, 2 H), 7.17 (m, 2 H), 4.03 (d, 1 H), 3.71 (t, 2 H), 3.67-3.57 (m, 5 H), 3.49-3.35 (m, 3 H), 3.17 (br s, 4 H), 3.06 (t, 1 H), 2.98-2.86 (m, 3 H), 2.62-2.55 (m, 3 H), 2.30 (d, 2 H), 1.95 (q, 1 H), 1.16 (t, 3 H), 1.07 (t, 3 H).

Example 36

{3-[3-(2-Methoxyethyl)-1,2,4-oxadiazol-5-yl]-5-[4-(trifluoromethyl)phenyl]piperidin-1-yl}(1-oxidothiomorpholin-4-yl)methanone [racemic cis isomer]

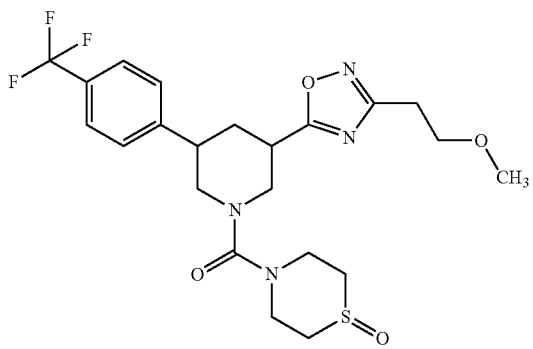 [SMILES: COCCc1noc(C2CC(c3ccc(C(F)(F)F)cc3)CN(C(=O)N3CCS(=O)CC3)C2)n1]

According to General Method 1, 196 mg (0.405 mmol) of the compound from Example 18A were reacted. Yield: 194 mg (96% of theory)

LC-MS (Method 2B): $R_t$=1.08 min; MS (ESIpos): m/z=501 [M+H]$^+$;

$^1$H NMR (400 MHz, DMSO-d$_6$): δ=7.70 (d, 2 H), 7.58 (d, 2H), 4.00 (d, 1H), 3.73-3.58 (m, 5 H), 3.57-3.48 (m, 2 H), 3.48-3.39 (m, 1 H), 3.13-2.99 (m, 3 H), 2.97-2.84 (m, 4 H), 2.77-2.65 (m, 2 H), 2.35 (d, 1 H), 2.03 (q, 1 H).

Example 37

{3-[3-(2-Methoxyethyl)-1,2,4-oxadiazol-5-yl]-5-[4-(trifluoromethyl)phenyl]piperidin-1-yl}(1-oxidothiomorpholin-4-yl)methanone [enantiomerically pure cis isomer]

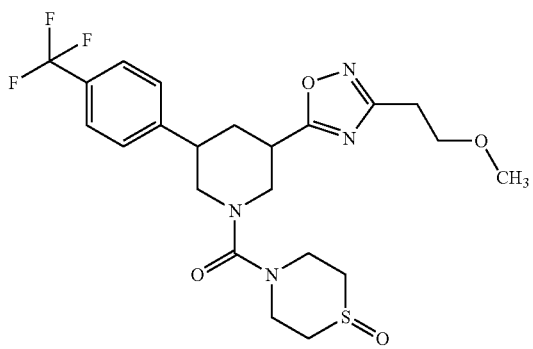 [SMILES: COCCc1noc(C2CC(c3ccc(C(F)(F)F)cc3)CN(C(=O)N3CCS(=O)CC3)C2)n1]

Enantiomer separation of 194 mg of the racemate from Example 36 according to Method 1D gave 81.1 mg of the title compound from Example 37 and 78.5 mg of the title compound from Example 38.

LC-MS (Method 2B): $R_t$=1.08 min; MS (ESIpos): m/z=501 [M+H]$^+$;

HPLC (Method 1E): $R_t$=8.45 min, >99.0% ee;

$^1$H NMR (400 MHz, DMSO-d$_6$): δ=7.70 (d, 2 H), 7.58 (d, 2 H), 4.00 (d, 1H), 3.73-3.58 (m, 5H), 3.57-3.48 (m, 2 H), 3.48-3.39 (m, 1 H), 3.13-2.99 (m, 3 H), 2.97-2.84 (m, 4 H), 2.77-2.65 (m, 2 H), 2.35 (d, 1 H), 2.03 (q, 1 H).

Example 38

{3-[3-(2-Methoxyethyl)-1,2,4-oxadiazol-5-yl]-5-[4-(trifluoromethyl)phenyl]piperidin-1-yl}(1-oxidothiomorpholin-4-yl)methanone [enantiomerically pure cis isomer]

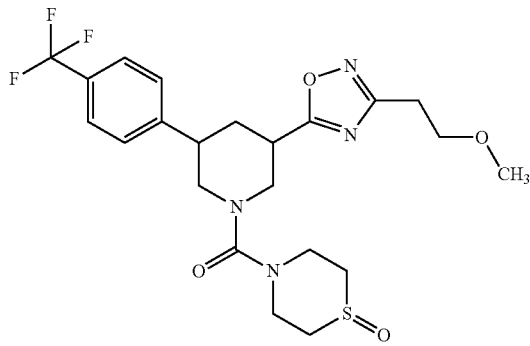 [SMILES: COCCc1noc(C2CC(c3ccc(C(F)(F)F)cc3)CN(C(=O)N3CCS(=O)CC3)C2)n1]

Enantiomer separation of 194 mg of the racemate from Example 36 according to Method 1D gave 81.1 mg of the title compound from Example 37 and 78.5 mg of the title compound from Example 38.

LC-MS (Method 2B): $R_t$=1.08 min; MS (ESIpos): m/z=501 [M+H]$^+$;

HPLC (Method 1E): $R_t$=18.94 min, >99.0% ee;

$^1$H NMR (400 MHz, DMSO-d$_6$): δ=7.70 (d, 2 H), 7.58 (d, 2 H), 4.00 (d, 1 H), 3.73-3.58 (m, 5 H), 3.57-3.48 (m, 2 H), 3.48-3.39 (m, 1 H), 3.13-2.99 (m, 3 H), 2.97-2.84 (m, 4 H), 2.77-2.65 (m, 2 H), 2.35 (d, 1 H), 2.03 (q, 1 H).

Example 39

{3-[4-(2,2-Difluoroethyl)phenyl]-5-[3-(2-methoxyethyl)-1,2,4-oxadiazol-5-yl]piperidin-1-yl}(1,1-dioxidothiomorpholin-4-yl)methanone [racemic cis isomer]

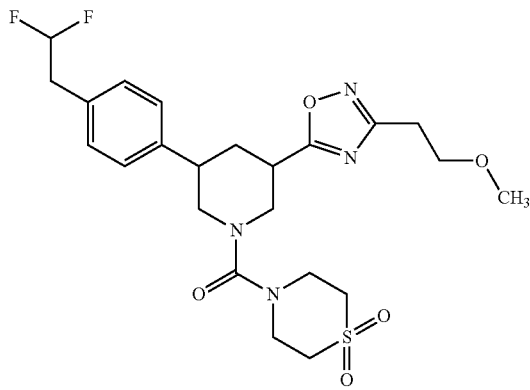 [SMILES: COCCc1noc(C2CC(c3ccc(CC(F)F)cc3)CN(C(=O)N3CCS(=O)(=O)CC3)C2)n1]

14.7 mg (0.031 mmol) of the compound from Example 63A were reacted according to General Method 2 with 26.3 mg (0.076 mmol) of meta-chloroperbenzoic acid. Yield: 9.5 mg (60% of theory)

$^1$H NMR (400 MHz, DMSO-$d_6$): δ=7.33 (d, 2 H), 7.26 (m, 2 H), 6.23 (tt, 1H), 4.03 (d, 1H), 3.71-3.56 (m, 7H), 3.46-3.36 (m, 1H), 3.23 (s, 3H), 3.21-3.13 (m, 5H), 3.12-2.87 (m, 6H), 2.31 (d, 1H), 1.97 (q, 1H).

Example 40

{3-(3-Cyclopropyl-1,2,4-oxadiazol-5-yl)-5-[4-(2,2,2-trifluoroethyl)phenyl]piperidin-1-yl}(1-oxidothiomorpholin-4-yl)methanone [racemic cis isomer]

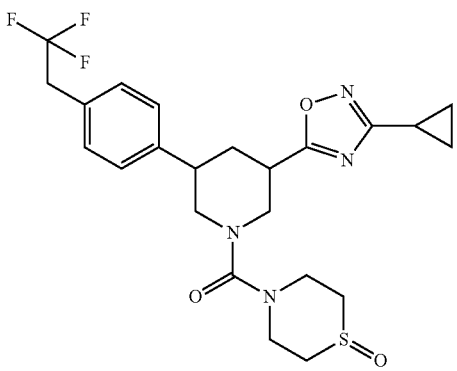 [SMILES: O=C(N1CCS(=O)CC1)N1CC(c2ccc(CC(F)(F)F)cc2)CC(c2nc(C3CC3)no2)C1]

78.0 mg (0.162 mmol) of the compound from Example 46A were reacted according to General Method 1 with 50.4 mg (0.146 mmol) of meta-chloroperbenzoic acid. Yield: 76.2 mg (88% of theory)

LC-MS (Method 5B): $R_t$=1.02 min; MS (ESIpos): m/z=497 [M+H]$^+$.

Example 41

{3-(3-Cyclopropyl-1,2,4-oxadiazol-5-yl)-5-[4-(2,2,2-trifluoroethyl)phenyl]piperidin-1-yl}(1-oxidothiomorpholin-4-yl)methanone [enantiomerically pure cis isomer]

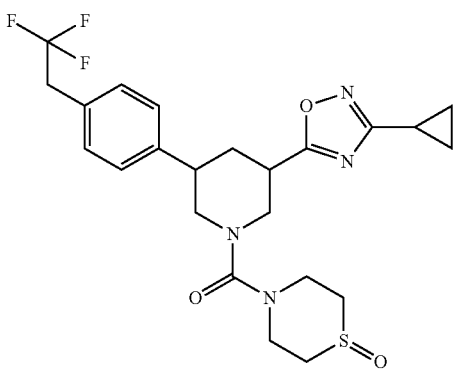 [SMILES: O=C(N1CCS(=O)CC1)N1CC(c2ccc(CC(F)(F)F)cc2)CC(c2nc(C3CC3)no2)C1]

Enantiomer separation of 76.2 mg of the racemate from Example 40 according to Method 7D gave 29.1 mg of the title compound from Example 41 (Enantiomer 1) and 28.9 mg of the title compound from Example 42 (Enantiomer 2).

LC-MS (Method 7B): $R_t$=2.18 min; MS (ESIpos): m/z=497 [M+H]$^+$;

HPLC (Method 6E): $R_t$=13.2 min, >99.0% ee;

$^1$H NMR (400 MHz, DMSO-$d_6$): δ=7.37-7.29 (m, 4H), 3.96 (d, 1H), 3.68-3.47 (m, 7H), 3.41-3.33 (m, 1H), 3.07-2.85 (m, 5H), 2.74-2.66 (m, 2H), 2.28 (d, 1H), 2.16-2.08 (m, 1H), 1.93 (q, 1H), 1.08-1.02 (m, 2H), 0.92-0.85 (m, 2H).

Example 42

{3-(3-Cyclopropyl-1,2,4-oxadiazol-5-yl)-5-[4-(2,2,2-trifluoroethyl)phenyl]piperidin-1-yl}(1-oxidothiomorpholin-4-yl)methanone [enantiomerically pure cis isomer]

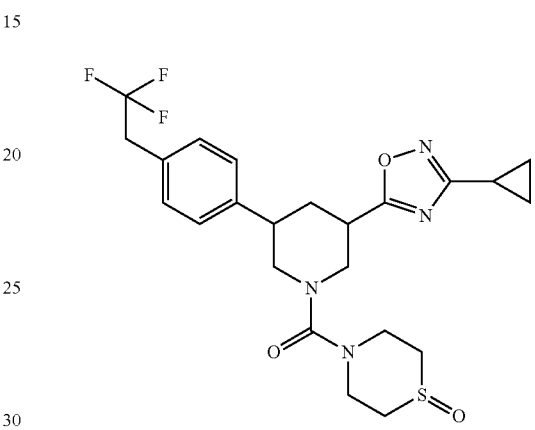

Enantiomer separation of 76.2 mg of the racemate from Example 40 according to Method 7D gave 29.1 mg of the title compound from Example 41 (Enantiomer 1) and 28.9 mg of the title compound from Example 42 (Enantiomer 2).

LC-MS (Method 7B): $R_t$=2.18 min; MS (ESIpos): m/z=497 [M+H]$^+$;

HPLC (Method 6E): $R_t$=16.4 min, >99.0% ee;

$^1$H NMR (400 MHz, DMSO-$d_6$): δ=7.37-7.29 (m, 4H), 3.96 (d, 1H), 3.68-3.47 (m, 7H), 3.41-3.33 (m, 1H), 3.07-2.85 (m, 5H), 2.74-2.66 (m, 2H), 2.28 (d, 1H), 2.16-2.08 (m, 1H), 1.93 (q, 1H), 1.08-1.02 (m, 2H), 0.92-0.85 (m, 2H).

Example 43

{3-(3-Cyclopropyl-1,2,4-oxadiazol-5-yl)-5-[4-(2,2,2-trifluoroethyl)phenyl]piperidin-1-yl}(1,1-dioxidothiomorpholin-4-yl)methanone [racemic cis isomer]

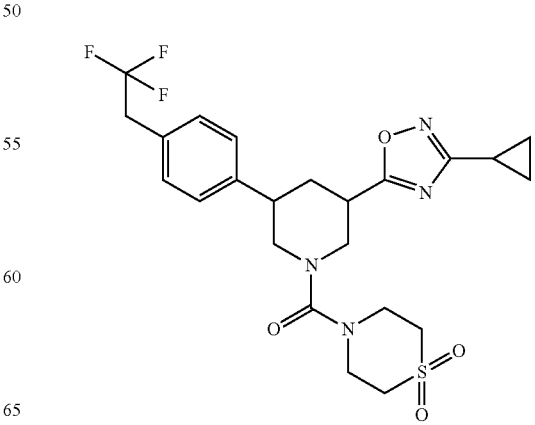

78.0 mg (0.162 mmol) of the compound from Example 46A were reacted according to General Method 2 with 140 mg (0.146 mmol) of meta-chloroperbenzoic acid. Yield: 87.5 mg (100% of theory)

LC-MS (Method 2B): $R_t$=1.25 min; MS (ESIpos): m/z=513 [M+H]$^+$.

Example 44

{3-(3-Cyclopropyl-1,2,4-oxadiazol-5-yl)-5-[4-(2,2,2-trifluoroethyl)phenyl]piperidin-1-yl}(1,1-dioxidothiomorpholin-4-yl)methanone [enantiomerically pure cis isomer]

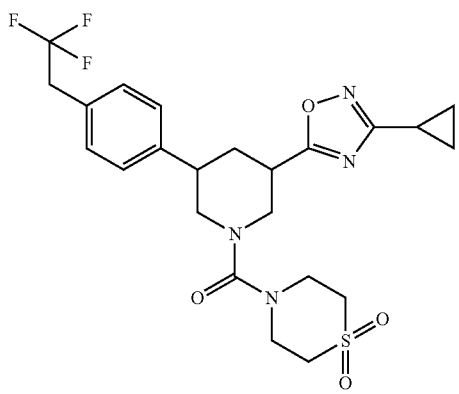 [SMILES: O=C(N1CCS(=O)(=O)CC1)N1CC(c2ccc(CC(F)(F)F)cc2)CC(c2nc(C3CC3)no2)C1]

Enantiomer separation of 87.5 mg of the racemate from Example 43 according to Method 8D gave 29.1 mg of the title compound from Example 44 (Enantiomer 1) and 30.7 mg of the title compound from Example 45 (Enantiomer 2).

LC-MS (Method 7B): $R_t$=2.34 min; MS (ESIpos): m/z=513 [M+H]$^+$;

HPLC (Method 7E): $R_t$=9.86 min, 99.0% ee;

$^1$H NMR (400 MHz, DMSO-d$_6$): δ=7.37-7.29 (m, 4H), 4.00 (d, 1H), 3.67-3.56 (m, 7H), 3.17 (br. s., 4H), 3.07-2.87 (m, 3H), 2.28 (d, 1H), 2.16-2.08 (m, 1H), 1.93 (q, 1H), 1.09-1.02 (m, 2H), 0.92-0.85 (m, 3H), one proton hidden.

Example 45

{3-(3-Cyclopropyl-1,2,4-oxadiazol-5-yl)-5-[4-(2,2,2-trifluoroethyl)phenyl]piperidin-1-yl}(1,1-dioxidothiomorpholin-4-yl)methanone [enantiomerically pure cis isomer]

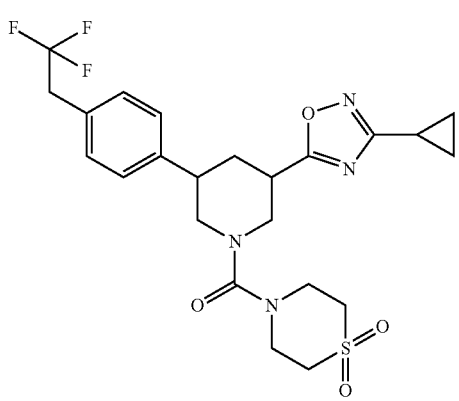 [SMILES: O=C(N1CCS(=O)(=O)CC1)N1CC(c2ccc(CC(F)(F)F)cc2)CC(c2nc(C3CC3)no2)C1]

Enantiomer separation of 87.5 mg of the racemate from Example 43 according to Method 8D gave 29.1 mg of the title compound from Example 44 (Enantiomer 1) and 30.7 mg of the title compound from Example 45 (Enantiomer 2).

LC-MS (Method 7B): $R_t$=2.34 min; MS (ESIpos): m/z=513 [M+H]$^+$;

HPLC (Method 7E): $R_t$=10.9 min, 97.5% ee;

$^1$H NMR (400 MHz, DMSO-d$_6$): δ=7.37-7.29 (m, 4H), 4.00 (d, 1H), 3.67-3.56 (m, 7H), 3.17 (br. s., 4H), 3.07-2.87 (m, 3H), 2.28 (d, 1H), 2.16-2.08 (m, 1H), 1.93 (q, 1H), 1.09-1.02 (m, 2H), 0.92-0.85 (m, 3H), one proton hidden.

Example 46

{3-[3-(2-Methoxyethyl)-1,2,4-oxadiazol-5-yl]-5-[4-(2,2,2-trifluoroethyl)phenyl]piperidin-1-yl}(1-oxidothiomorpholin-4-yl)methanone [enantiomerically pure cis isomer]

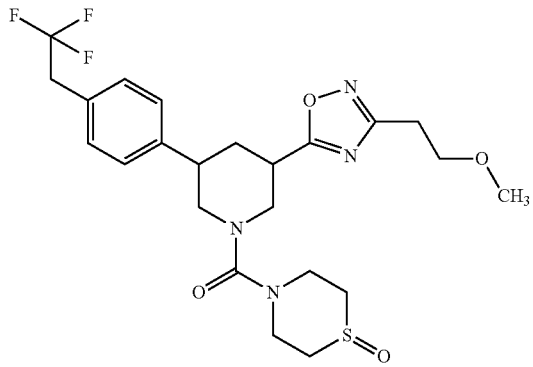 [SMILES: COCCc1noc(C2CC(c3ccc(CC(F)(F)F)cc3)CN(C(=O)N3CCS(=O)CC3)C2)n1]

113 mg (0.227 mmol) of the compound from Example 47A were reacted according to General Method 1 with 70.4 mg (0.204 mmol) of meta-chloroperbenzoic acid. Enantiomer separation of 108 mg of the racemate according to Method 9D gave 37.1 mg of the title compound from Example 46 (Enantiomer 1) and 41.8 mg of the title compound from Example 47 (Enantiomer 2).

LC-MS (Method 5B): $R_t$=0.96 min; MS (ESIpos): m/z=515 [M+H]$^+$;

HPLC (Method 8E): $R_t$=5.48 min, >99.0% ee;

$^1$H NMR (400 MHz, DMSO-d$_6$): δ=7.38-7.29 (m, 4H), 4.00 (d, 1H), 3.72-3.48 (m, 9H), 3.46-3.37 (m, 1H), 3.23 (s, 3H), 3.10-2.85 (m, 7H), 2.76-2.65 (m, 3H), 2.32 (d, 1H), 1.98 (q, 1H).

Example 47

{3-[3-(2-Methoxyethyl)-1,2,4-oxadiazol-5-yl]-5-[4-(2,2,2-trifluoroethyl)phenyl]piperidin-1-yl}(1-oxidothiomorpholin-4-yl)methanone [enantiomerically pure cis isomer]

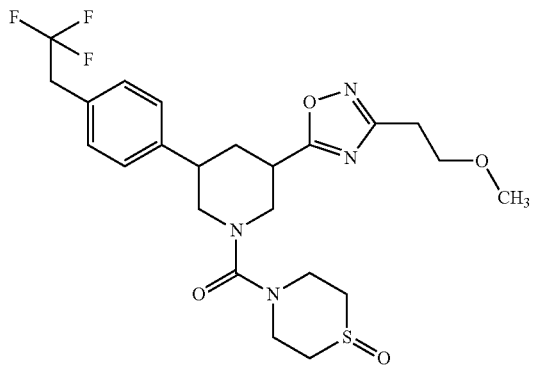 [SMILES: COCCc1noc(C2CC(c3ccc(CC(F)(F)F)cc3)CN(C(=O)N3CCS(=O)CC3)C2)n1]

113 mg (0.227 mmol) of the compound from Example 47A were reacted according to General Method 1 with 70.4 mg (0.204 mmol) of meta-chloroperbenzoic acid. Enantiomer separation of 108 mg of the racemate according to Method 9D gave 37.1 mg of the title compound from Example 46 (Enantiomer 1) and 41.8 mg of the title compound from Example 47 (Enantiomer 2).

LC-MS (Method 5B): $R_t$=0.96 min; MS (ESIpos): m/z=515 [M+H]$^+$;

HPLC (Method 8E): $R_t$=7.15 min, >99.0% ee;

$^1$H NMR (400 MHz, DMSO-d$_6$): δ=7.38-7.29 (m, 4H), 4.00 (d, 1H), 3.72-3.48 (m, 9H), 3.46-3.37 (m, 1H), 3.23 (s, 3H), 3.10-2.85 (m, 7H), 2.76-2.65 (m, 3H), 2.32 (d, 1H), 1.98 (q, 1H).

Example 48

(1,1-Dioxidothiomorpholin-4-yl){3-[3-(2-methoxyethyl)-1,2,4-oxadiazol-5-yl]-5-[4-(2,2,2-trifluoroethyl)phenyl]piperidin-1-yl}methanone [enantiomerically pure cis isomer]

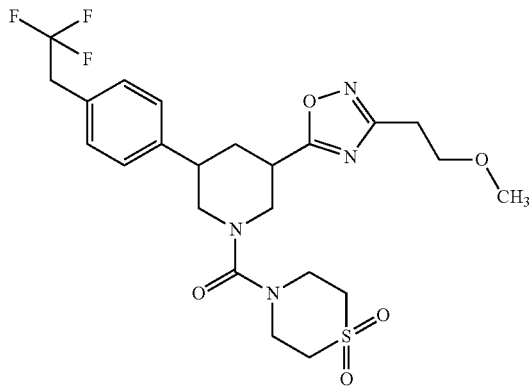 [SMILES: COCCc1noc(C2CC(c3ccc(CC(F)(F)F)cc3)CN(C(=O)N3CCS(=O)(=O)CC3)C2)n1]

113 mg (0.227 mmol) of the compound from Example 47A were reacted according to General Method 2 with 196 mg (0.567 mmol) of meta-chloroperbenzoic acid. Enantiomer separation of 121 mg of the racemate according to Method 9D gave 34.4 mg of the title compound from Example 48 (Enantiomer 1) and 29.2 mg of the title compound from Example 49 (Enantiomer 2).

LC-MS (Method 7B): $R_t$=2.17 min; MS (ESIpos): m/z=531 [M+H]$^+$;

HPLC (Method 8E): $R_t$=4.34 min, >99.0% ee;

$^1$H NMR (400 MHz, DMSO-d$_6$): δ=7.39-7.29 (m, 4H), 4.03 (d, 1H), 3.72-3.56 (m, 10H), 3.46-3.36 (m, 1H), 3.23 (s, 3H), 3.18 (br. s., 4H), 3.11-2.90 (m, 5H), 2.33-2.27 (m, 1H), 1.97 (q, 1H).

Example 49

(1,1-Dioxidothiomorpholin-4-yl){3-[3-(2-methoxyethyl)-1,2,4-oxadiazol-5-yl]-5-[4-(2,2,2-trifluoroethyl)phenyl]piperidin-1-yl}methanone [enantiomerically pure cis isomer]

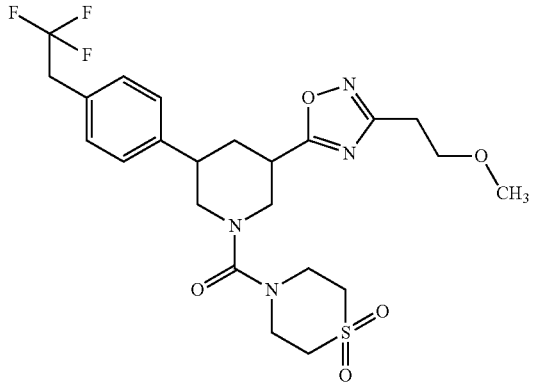 [SMILES: COCCc1noc(C2CC(c3ccc(CC(F)(F)F)cc3)CN(C(=O)N3CCS(=O)(=O)CC3)C2)n1]

113 mg (0.227 mmol) of the compound from Example 47A were reacted according to General Method 2 with 196 mg (0.567 mmol) of meta-chloroperbenzoic acid. Enantiomer separation of 121 mg of the racemate according to Method 9D gave 34.4 mg of the title compound from Example 48 (Enantiomer 1) and 29.2 mg of the title compound from Example 49 (Enantiomer 2).

LC-MS (Method 7B): $R_t$=2.18 min; MS (ESIpos): m/z=531 [M+H]$^+$;

HPLC (Method 8E): $R_t$=7.86 min, >99.0% ee;

$^1$H NMR (400 MHz, DMSO-d$_6$): δ=7.39-7.29 (m, 4H), 4.03 (d, 1H), 3.72-3.56 (m, 10H), 3.46-3.36 (m, 1H), 3.23 (s, 3H), 3.18 (br. s., 4H), 3.11-2.90 (m, 5H), 2.33-2.27 (m, 1H), 1.97 (q, 1H).

Example 50

{3-(3-Cyclopropyl-1,2,4-oxadiazol-5-yl)-5-[4-(1,1-difluoroethyl)phenyl]piperidin-1-yl}-(1-oxidothiomorpholin-4-yl)methanone [racemic cis isomer]

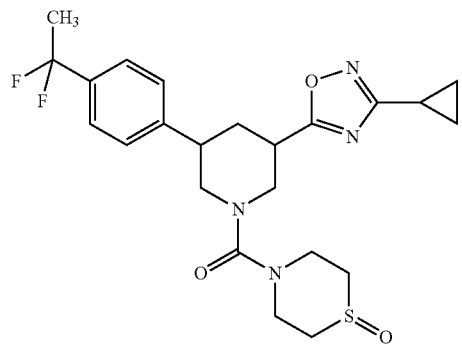 [SMILES: CC(F)(F)c1ccc(C2CC(c3nc(C4CC4)no3)CN(C(=O)N3CCS(=O)CC3)C2)cc1]

34.1 mg (0.074 mmol) of the compound from Example 54A were reacted according to General Method 1 with 22.9 mg (0.066 mmol) of meta-chloroperbenzoic acid. Yield: 39.7 mg (100% of theory).

LC-MS (Method 5B): $R_t$=0.99 min; MS (ESIpos): m/z=479 [M+H]$^+$.

Example 51

{3-(3-Cyclopropyl-1,2,4-oxadiazol-5-yl)-5-[4-(1,1-difluoroethyl)phenyl]piperidin-1-yl}-(1-oxido-thiomorpholin-4-yl)methanone [enantiomerically pure cis isomer]

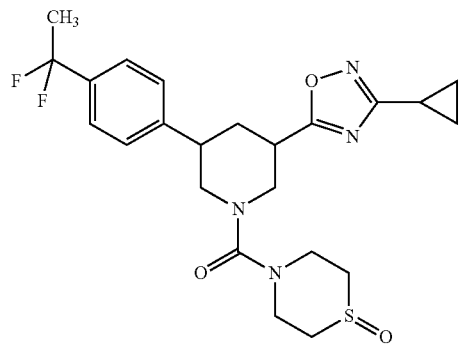 [SMILES: CC(F)(F)c1ccc(C2CC(c3nc(C4CC4)no3)CN(C(=O)N3CCS(=O)CC3)C2)cc1]

Enantiomer separation of 35.5 mg of the racemate from Example 50 according to Method 9D gave 12.0 mg of the title compound from Example 51 (Enantiomer 1) and 14.0 mg of the title compound from Example 52 (Enantiomer 2).

LC-MS (Method 5B): $R_t$=1.00 min; MS (ESIpos): m/z=479 [M+H]$^+$;

HPLC (Method 9E): $R_t$=5.27 min, >99.0% ee;

$^1$H NMR (400 MHz, DMSO-d$_6$): δ=7.53 (d, 2H), 7.45 (d, 2H), 3.96 (d, 1H), 3.71-3.46 (m, 5H), 3.42-3.35 (m, 1H), 3.09-2.84 (m, 5H), 2.71 (d, 2H), 2.29 (d, 1H), 2.16-2.08 (m, 1H), 2.02-1.90 (m, 4H), 1.10-1.02 (m, 2H), 0.93-0.85 (m, 2H).

Example 52

{3-(3-Cyclopropyl-1,2,4-oxadiazol-5-yl)-5-[4-(1,1-difluoroethyl)phenyl]piperidin-1-yl}-(1-oxido-thiomorpholin-4-yl)methanone [enantiomerically pure cis isomer]

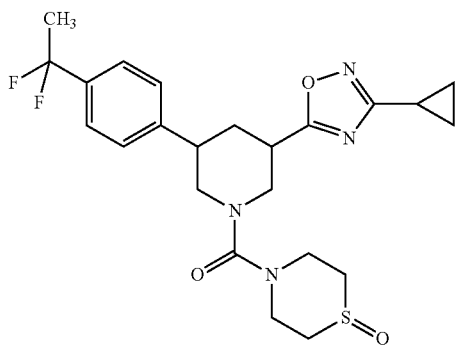 [SMILES: CC(F)(F)c1ccc(C2CC(c3nc(C4CC4)no3)CN(C(=O)N3CCS(=O)CC3)C2)cc1]

Enantiomer separation of 35.5 mg of the racemate from Example 50 according to Method 9D gave 12.0 mg of the title compound from Example 51 (Enantiomer 1) and 14.0 mg of the title compound from Example 52 (Enantiomer 2).

LC-MS (Method 5B): $R_t$=1.00 min; MS (ESIpos): m/z=479 [M+H]$^+$;

HPLC (Method 9E): $R_t$=6.78 min, >99.0% ee;

$^1$H NMR (400 MHz, DMSO-d$_6$): δ=7.53 (d, 2H), 7.45 (d, 2H), 3.96 (d, 1H), 3.71-3.46 (m, 5H), 3.42-3.35 (m, 1H), 3.09-2.84 (m, 5H), 2.71 (d, 2H), 2.29 (d, 1H), 2.16-2.08 (m, 1H), 2.02-1.90 (m, 4H), 1.10-1.02 (m, 2H), 0.93-0.85 (m, 2H).

Example 53

{3-(3-Cyclopropyl-1,2,4-oxadiazol-5-yl)-5-[4-(1,1-difluoroethyl)phenyl]piperidin-1-yl}(1,1-dioxidothiomorpholin-4-yl)methanone [racemic cis isomer]

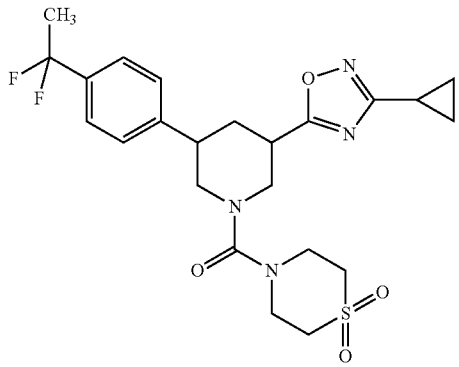 [SMILES: CC(F)(F)c1ccc(C2CC(c3nc(C4CC4)no3)CN(C(=O)N3CCS(=O)(=O)CC3)C2)cc1]

34.1 mg (0.074 mmol) of the compound from Example 54A were reacted according to General Method 2 with 63.6 mg (0.184 mmol) of meta-chloroperbenzoic acid. Yield: 37.1 mg (99% of theory)

LC-MS (Method 5B): $R_t$=1.06 min; MS (ESIpos): m/z=495 [M+H]$^+$;

$^1$H NMR (400 MHz, DMSO-d$_6$): δ=7.52 (d, 2H), 7.44 (d, 2H), 4.00 (d, 1H), 3.69-3.56 (m, 5H), 3.41-3.34 (m, 1H), 3.17 (br. s., 4H), 3.10-2.95 (m, 3H), 2.28 (d, 1H), 2.17-2.07 (m, 1H), 2.03-1.89 (m, 4H), 1.10-1.01 (m, 2H), 0.94-0.85 (m, 2H).

Example 54

{3-(3-Cyclopropyl-1,2,4-oxadiazol-5-yl)-5-[4-(1,1-difluoroethyl)phenyl]piperidin-1-yl}-(1,1-dioxidothiomorpholin-4-yl)methanone [enantiomerically pure cis isomer]

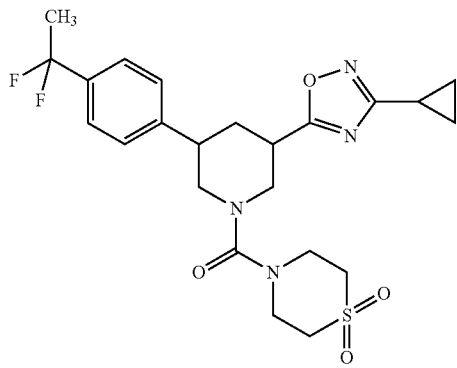 [SMILES: CC(F)(F)c1ccc(C2CC(c3nc(C4CC4)no3)CN(C(=O)N3CCS(=O)(=O)CC3)C2)cc1]

Enantiomer separation of 37.1 mg of the racemate from Example 53 according to Method 9D gave 13.0 mg of the title compound from Example 54 (Enantiomer 1) and 14.0 mg of the title compound from Example 55 (Enantiomer 2).

HPLC (Method 9E): $R_t$=5.81 min, >99.0% ee;

$^1$H NMR (400 MHz, DMSO-d$_6$): δ=7.52 (d, 2H), 7.44 (d, 2H), 4.00 (d, 1H), 3.69-3.56 (m, 5H), 3.41-3.34 (m, 1H), 3.17 (br. s., 4H), 3.10-2.95 (m, 3H), 2.28 (d, 1H), 2.17-2.07 (m, 1H), 2.03-1.89 (m, 4H), 1.10-1.01 (m, 2H), 0.94-0.85 (m, 2H).

Example 55

{3-(3-Cyclopropyl-1,2,4-oxadiazol-5-yl)-5-[4-(1,1-difluoroethyl)phenyl]piperidin-1-yl}-(1,1-dioxidothiomorpholin-4-yl)methanone [enantiomerically pure cis isomer]

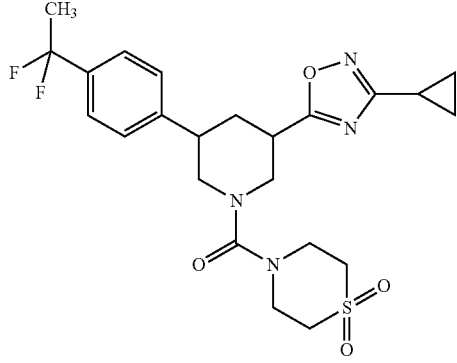 [SMILES: CC(F)(F)c1ccc(C2CC(c3nc(C4CC4)no3)CN(C(=O)N3CCS(=O)(=O)CC3)C2)cc1]

Enantiomer separation of 37.1 mg of the racemate from Example 53 according to Method 9D gave 13.0 mg of the title compound from Example 54 (Enantiomer 1) and 14.0 mg of the title compound from Example 55 (Enantiomer 2).

HPLC (Method 9E): $R_t$=9.63 min, >99.0% ee;

$^1$H NMR (400 MHz, DMSO-$d_6$): δ=7.52 (d, 2H), 7.44 (d, 2H), 4.00 (d, 1H), 3.69-3.56 (m, 5H), 3.41-3.34 (m, 1H), 3.17 (br. s., 4H), 3.10-2.95 (m, 3H), 2.28 (d, 1H), 2.17-2.07 (m, 1H), 2.03-1.89 (m, 4H), 1.10-1.01 (m, 2H), 0.94-0.85 (m, 2H).

Example 56

{3-(3-Cyclopropyl-1,2,4-oxadiazol-5-yl)-5-[4-(difluoromethoxy)phenyl]piperidin-1-yl}(1,1-dioxidothiomorpholin-4-yl)methanone [racemic cis isomer]

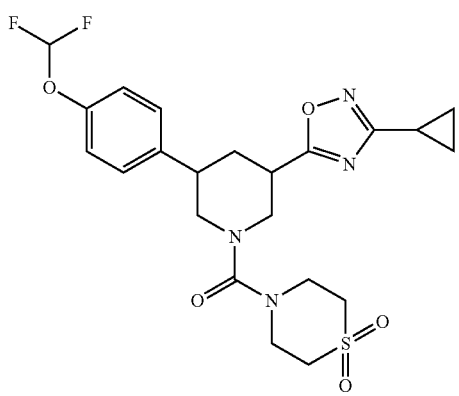 [SMILES: O=C(N1CCS(=O)(=O)CC1)N1CC(c2ccc(OC(F)F)cc2)CC(c2nc(C3CC3)no2)C1]

100 mg (0.23 mmol) of the compound from Example 37A and 46 mg (0.46 mmol) of N-hydroxycyclopropanecarboximidamide were initially charged in 0.8 ml of DMF and reacted with 132 mg (0.35 mmol) of HATU and 0.12 ml (90 mg, 0.69 mmol) of N,N-diisopropylethylamine. The reaction mixture was stirred at RT for 15 minutes and then partitioned between water and ethyl acetate. The organic phase was washed repeatedly with water, dried over sodium sulphate and concentrated under reduced pressure. The residue was taken up in 3.0 ml of DMF and converted in a microwave at 180° C. for 2 minutes. The reaction mixture was purified by means of preparative HPLC. Yield: 46 mg (37% of theory)

LC-MS (Method 2B): $R_t$=1.20 min; MS (ESIpos): m/z=497 [M+H]$^+$;

$^1$H NMR (400 MHz, DMSO-$d_6$): δ=7.43-7.30 (m, 2H), 7.14 (d, 2H), 4.09 (q, 1H), 3.99 (br. d, 1H), 3.63 (br. d., 1H), 3.40-3.33 (m, 1H), 3.33-3.28 (m, 4H), 3.22-3.10 (m, 4H), 3.08-2.88 (m, 3H), 2.28 (br. d, 1H), 2.16-2.07 (m, 1H), 2.00-1.87 (m, 1H), 1.12-0.99 (m, 2H), 0.94-0.84 (m, 2H).

Example 57

{3-[4-(Difluoromethoxy)phenyl]-5-[3-(2-methoxyethyl)-1,2,4-oxadiazol-5-yl]piperidin-1-yl}(1,1-dioxidothiomorpholin-4-yl)methanone [racemic cis isomer]

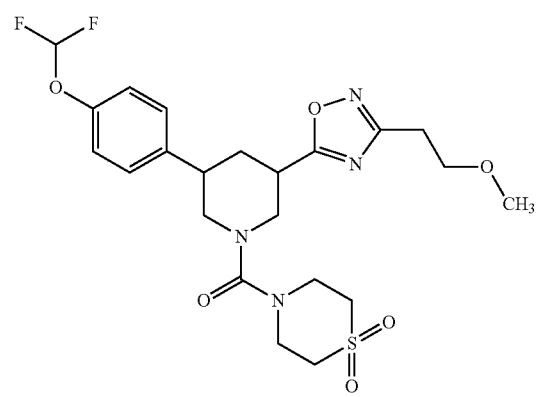 [SMILES: COCCc1noc(C2CC(c3ccc(OC(F)F)cc3)CN(C(=O)N3CCS(=O)(=O)CC3)C2)n1]

300 mg (0.69 mmol) of the compound from Example 37A and 246 mg (2.08 mmol) of N'-hydroxy-3-methoxypropanimidamide were initially charged in 2.6 ml of DMF and reacted with 396 mg (1.0 mmol) of HATU and 0.36 ml (269 mg, 2.1 mmol) of N,N-diisopropylethylamine. The reaction mixture was stirred at RT for 15 minutes and then partitioned between water and ethyl acetate. The organic phase was washed repeatedly with water, dried over sodium sulphate and concentrated under reduced pressure. The residue was dissolved in 2.0 ml of DMF and converted in a microwave at 180° C. for 2 minutes. The reaction mixture was purified by means of preparative HPLC. Yield: 141 mg (38% of theory)

LC-MS (Method 2B): $R_t$=1.10 min; MS (ESIpos): m/z=515 [M+H]$^+$;

$^1$H NMR (400 MHz, DMSO-$d_6$): δ=7.43-7.33 (m, 2H), 7.15 (d, 2H), 4.11-3.99 (m, 2H), 3.71-3.64 (m, 3H), 3.64-3.55 (m, 4H), 3.46-3.35 (m, 1H), 3.35-3.30 (m, 4H), 3.18 (br. s, 3H), 3.14-2.90 (m, 5H), 2.30 (br. d, 1H), 2.03-1.92 (m, 1H).

Example 58

{3-[4-(Difluoromethoxy)phenyl]-5-[3-(2-methoxyethyl)-1,2,4-oxadiazol-5-yl]piperidin-1-yl}(1,1-dioxidothiomorpholin-4-yl)methanone [enantiomerically pure cis isomer]

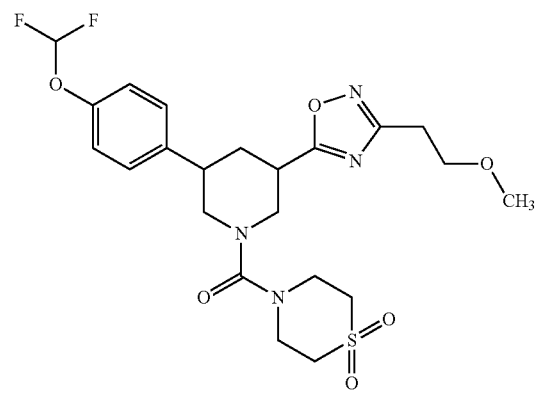 [SMILES: COCCc1noc(C2CC(c3ccc(OC(F)F)cc3)CN(C(=O)N3CCS(=O)(=O)CC3)C2)n1]

The enantiomer separation of 117 mg of the racemate from Example 57 according to Method 10D gave 43 mg of the compound from Example 58 (Enantiomer 1) and 38 mg of the compound from Example 59 (Enantiomer 2).

HPLC (Method 10E): $R_t$=4.17 min, >99.0% ee;

LC-MS (Method 2B): $R_t$=1.10 min; MS (ESIpos): m/z=515 [M+H]$^+$.

Example 59

{3-[4-(Difluoromethoxy)phenyl]-5-[3-(2-methoxyethyl)-1,2,4-oxadiazol-5-yl]piperidin-1-yl}(1,1-dioxidothiomorpholin-4-yl)methanone [enantiomerically pure cis isomer]

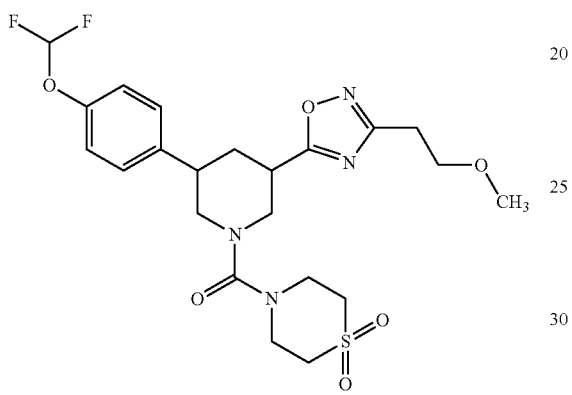

The enantiomer separation of 117 mg of the racemate from Example 57 according to Method 10D gave 43 mg of the compound from Example 58 (Enantiomer 1) and 38 mg of the compound from Example 59 (Enantiomer 2).

HPLC (Method 10E): $R_t$=9.24 min, >99.0% ee;

LC-MS (Method 2B): $R_t$=1.10 min; MS (ESIpos): m/z=515 [M+H]$^+$.

Example 60

{3-(3-Cyclopropyl-1,2,4-oxadiazol-5-yl)-5-[4-(difluoromethoxy)phenyl]piperidin-1-yl}(1-oxidothiomorpholin-4-yl)methanone [racemic cis isomer]

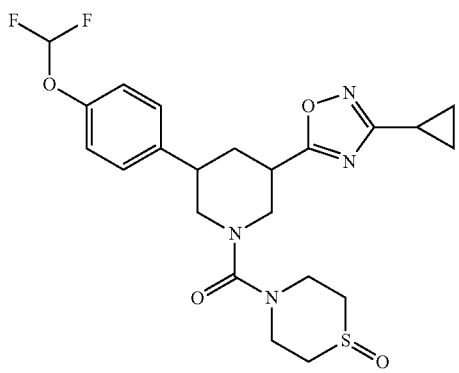 [SMILES: O=C(N1CCS(=O)CC1)N1CC(c2ccc(OC(F)F)cc2)CC(c2nc(C3CC3)no2)C1]

200 mg (0.48 mmol) of the compound from Example 39A and 96 mg (0.96 mmol) of N'-hydroxycyclopropanecarboximidamide were initially charged in 1.8 ml of DMF and reacted with 274 mg (0.72 mmol) of HATU and 0.25 ml (186 mg, 1.44 mmol) of N,N-diisopropylethylamine. The reaction mixture was stirred at RT for 15 minutes and then partitioned between water and ethyl acetate. The organic phase was washed repeatedly with water, dried over sodium sulphate and concentrated under reduced pressure. The residue was dissolved in 2.0 ml of DMF and converted in a microwave at 180° C. for 2 minutes. The reaction mixture was purified by means of preparative HPLC. Yield: 25 mg (10% of theory)

LC-MS (Method 2B): $R_t$=1.12 min; MS (ESIpos): m/z=481 [M+H]$^+$;

$^1$H NMR (400 MHz, DMSO-$d_6$): δ=7.42-7.35 (m, 2H), 7.14 (d, 2H), 4.01-3.87 (m, 1H), 3.69-3.45 (m, 5H), 3.42-3.34 (m, 1H), 3.07-2.85 (m, 5H), 2.70 (br. d, 2H), 2.34-2.23 (m, 1H), 2.15-2.07 (m, 1H), 1.99-1.88 (m, 1H), 1.12-1.01 (m, 2H), 0.94-0.85 (m, 2H).

Example 61

(1,1-Dioxidothiomorpholin-4-yl){3-[3-(1-methoxycyclopropyl)-1,2,4-oxadiazol-5-yl]-5-[4-(2,2,2-trifluoroethyl)phenyl]piperidin-1-yl}methanone [racemic cis isomer]

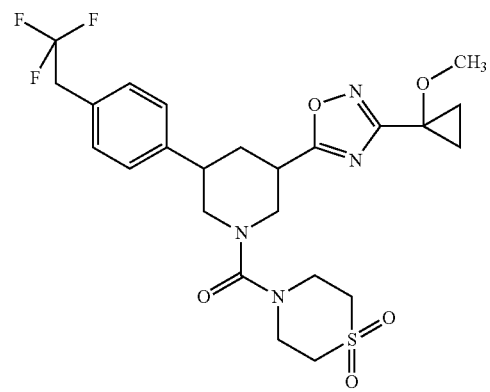 [SMILES: COC1(c2noc(C3CC(c4ccc(CC(F)(F)F)cc4)CN(C(=O)N4CCS(=O)(=O)CC4)C3)n2)CC1]

29.0 mg (0.162 mmol) of the compound from Example 65A were reacted according to General Method 2 with 49.0 mg (0.142 mmol) of meta-chloroperbenzoic acid. Yield: 31.2 mg (95% of theory)

LC-MS (Method 5B): $R_t$=1.06 min; MS (ESIpos): m/z=543 [M+H]$^+$;

$^1$H NMR (400 MHz, DMSO-$d_6$): δ=7.37-7.29 (m, 4H), 4.02 (d, 1H), 3.68-3.55 (q, 7H), 3.38 (s, 3H), 3.17 (br. s., 4H), 3.10-2.88 (m, 3H), 2.30 (d, 1H), 1.95 (q, 1H), 1.34-1.28 (m, 2H), 1.20-1.12 (m, 2H).

Example 62

(1,1-Dioxidothiomorpholin-4-yl){3-[3-(1-methoxy-cyclopropyl)-1,2,4-oxadiazol-5-yl]-5-[4-(2,2,2-trifluoroethyl)phenyl]piperidin-1-yl}methanone [enantiomerically pure cis isomer]

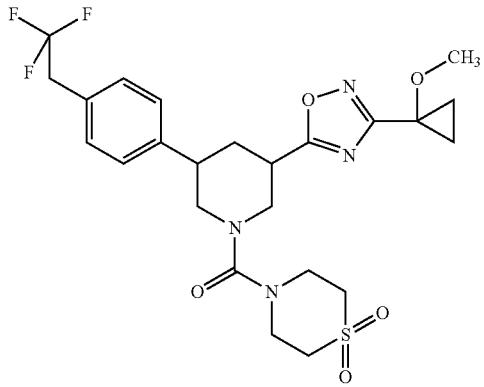 [SMILES: COC1(c2noc(C3CC(c4ccc(CC(F)(F)F)cc4)CN(C(=O)N4CCS(=O)(=O)CC4)C3)n2)CC1]

Enantiomer separation of 31.2 mg of the racemate from Example 61 according to Method 11D gave 12.0 mg of the title compound from Example 62 (Enantiomer 1) and 12.0 mg of the title compound from Example 63 (Enantiomer 2).

LC-MS (Method 2B): $R_t$=1.26 min; MS (ESIpos): m/z=543 [M+H]$^+$;

HPLC (Method 11E): $R_t$=17.9 min, >99.0% ee;

$^1$H NMR (400 MHz, DMSO-$d_6$): δ=7.37-7.29 (m, 4H), 4.02 (d, 1H), 3.68-3.55 (q, 7H), 3.38 (s, 3H), 3.17 (br. s., 4H), 3.10-2.88 (m, 3H), 2.30 (d, 1H), 1.95 (q, 1H), 1.34-1.28 (m, 2H), 1.20-1.12 (m, 2H).

Example 63

(1,1-Dioxidothiomorpholin-4-yl){3-[3-(1-methoxy-cyclopropyl)-1,2,4-oxadiazol-5-yl]-5-[4-(2,2,2-trifluoroethyl)phenyl]piperidin-1-yl}methanone [enantiomerically pure cis isomer]

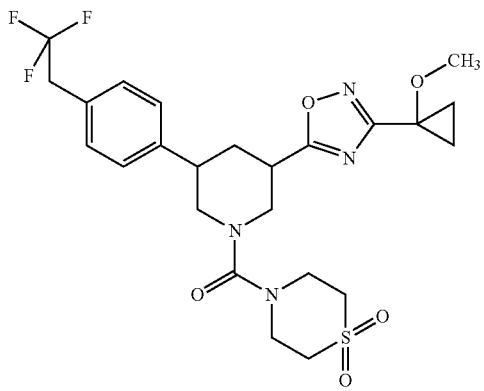 [SMILES: COC1(c2noc(C3CC(c4ccc(CC(F)(F)F)cc4)CN(C(=O)N4CCS(=O)(=O)CC4)C3)n2)CC1]

Enantiomer separation of 31.2 mg of the racemate from Example 61 according to Method 11D gave 12.0 mg of the title compound from Example 62 (Enantiomer 1) and 12.0 mg of the title compound from Example 63 (Enantiomer 2).

LC-MS (Method 2B): $R_t$=1.26 min; MS (ESIpos): m/z=543 [M+H]$^+$;

HPLC (Method 11E): $R_t$=29.2 min, >99.0% ee;

$^1$H NMR (400 MHz, DMSO-$d_6$): δ=7.37-7.29 (m, 4H), 4.02 (d, 1H), 3.68-3.55 (q, 7H), 3.38 (s, 3H), 3.17 (br. s., 4H), 3.10-2.88 (m, 3H), 2.30 (d, 1H), 1.95 (q, 1H), 1.34-1.28 (m, 2H), 1.20-1.12 (m, 2H).

B) Assessment of Physiological Activity

Abbreviations:

| | |
|---|---|
| BSA | bovine serum albumin |
| DMEM | Dulbecco's Modified Eagle Medium |
| EGTA | ethylene glycol bis-(2-aminoethyl)-N,N,N',N'-tetraacetic acid |
| FCS | fetal calf serum |
| HEPES | 4-(2-hydroxyethyl)-1-piperazineethanesulphonic acid |
| [3H]haTRAP | tritiated high affinity thrombin receptor activating peptide |
| PRP | platelet-rich plasma |

The suitability of the inventive compounds for treating thromboembolic disorders can be demonstrated in the following assay systems:

1.) In Vitro Assays 1.a) Cellular Functional In Vitro Test

A recombinant cell line is used to identify agonists of the human protease activated receptor 1 (PAR1) and to quantify the activity of the substances described herein. The cell is originally derived from a human embryonal kidney cell (HEK293; ATCC: American Type Culture Collection, Manassas, Va. 20108, USA). The test cell line constitutively expresses a modified form of the calcium-sensitive photoprotein aequorin which, after reconstitution with the cofactor coelenterazine, emits light when the free calcium concentration in the inner mitochondrial compartment is increased (Rizzuto R, Simpson A W, Brini M, Pozzan T.; Nature 1992, 358, 325-327). Additionally, the cell stably expresses the endogenous human PAR1 receptor and the endogenous purinergic receptor P2Y2. The resulting PAR1 test cell responds to stimulation of the endogenous PAR1 or P2Y2 receptor with an intracellular release of calcium ions, which can be quantified through the resulting aequorin luminescence with a suitable luminometer (Milligan G, Marshall F, Rees S, Trends in Pharmacological Sciences 1996, 17, 235-237).

For the testing of the substance specificity, the effect thereof after activation of the endogenous PAR1 receptor is compared with the effect after activation of the endogenous purinergic P2Y2 receptor which utilizes the same intracellular signal path.

Test procedure: The cells are plated out two days (48 hours) before the test in culture medium (DMEM F12, supplemented with 10% FCS, 2 mM glutamine, 20 mM HEPES, 1.4 mM pyruvate, 0.1 mg/ml gentamycin, 0.15% sodium bicarbonate; BioWhittaker Cat.# BE04-687Q; B-4800 Verviers, Belgium) in 384-well microtitre plates and kept in a cell incubator (96% atmospheric humidity, 5% v/v $CO_2$, 37° C.). On the day of the test, the culture medium is replaced by a Tyrode's solution (in mM: 140 sodium chloride, 5 potassium chloride, 1 magnesium chloride, 2 calcium chloride, 20 glucose, 20 HEPES), which additionally contains the cofactor coelenterazine (25 µM) and glutathione (4 mM), and the microtitre plate is then incubated for a further 3-4 hours. The test substances are then pipetted onto the microtitre plate, and 5 minutes after the transfer of the test substances into the wells of the microtitre plate the plate is transferred into the luminometer, a PAR1 agonist concentration which corresponds to $EC_{50}$ is added and the resulting light signal is immediately measured in the luminometer. To distinguish an antagonist substance action from a toxic action, the endogenous purinergic receptor is immediately subsequently activated with agonist (ATP, final concentration 10 μM) and the resulting light signal is measured. The results are shown in Table A:

TABLE A

| Example No. | IC$_{50}$ [nM] |
|---|---|
| 1 | 43 |
| 8 | 33 |
| 10 | 8.0 |
| 15 | 5.1 |
| 20 | 23 |
| 31 | 32 |
| 52 | 4.7 |
| 54 | 4.3 |
| 61 | 15.7 |

1.b) PAR-1 Receptor Binding Assay

Platelet membranes are incubated with 12 nM [3H]ha-TRAP and test substance in different concentrations in a buffer (50 mM Tris pH 7.5, 10 mM magnesium chloride, 1 mM EGTA, 0.1% BSA) at room temperature for 80 min. Then the mixture is transferred to a filter plate and washed twice with buffer. After addition of scintillation liquid, the radioactivity on the filter is measured in a beta counter.

1.c) Platelet Aggregation in Plasma

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min.

For the aggregation measurements, aliquots of the platelet-rich plasma with increasing concentrations of test substance are incubated at 37° C. for 10 min. Subsequently, aggregation is triggered by addition of a thrombin receptor agonist (TRAP6, SFLLRN) in an aggregometer and determined at 37° C. by means of the turbidimetry method according to Born (Born, G.V.R., Cross M.J., The Aggregation of Blood Platelets; *J. Physiol.* 1963, 168, 178-195). The SFLLRN concentration leading to maximum aggregation is, if appropriate, determined individually for each donor.

To calculate the inhibitory effect, the maximum increase in light transmission (amplitude of the aggregation curve in %) is determined within 5 minutes after addition of the agonist in the presence and absence of test substance, and the inhibition is calculated. The inhibition curves are used to calculate the concentration which inhibits aggregation by 50%. The results are shown in Table B:

TABLE B

| Example No. | IC$_{50}$ [nM] |
|---|---|
| 8 | 0.29 |
| 10 | 0.49 |
| 13 | 0.17 |
| 52 | 0.58 |

1.d) Platelet Aggregation in Buffer

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. The platelets are resuspended in incubation buffer and adjusted to 200 000 cells/W. Prior to the start of the test, calcium chloride and magnesium chloride, final concentration in each case 2 mM (2M stock solution, dilution 1:1000), are added. Note: in the case of ADP-induced aggregation, only calcium chloride is added. The following agonists can be used: TRAP6-trifluoroacetate salt, collagen, human α-thrombin and U-46619. For each donor, the concentration of the agonist is tested.

Test procedure: 96-well microtitre plates are used. The test substance is diluted in DMSO, and 2 μl per well is initially charged. 178 μl of platelet suspension are added, and the mixture is preincubated at room temperature for 10 minutes. 20 μl of agonist are added, and the measurement in the Spectramax, OD 405 nm, is started immediately. Kinetics are determined in 11 measurements of 1 minute each. Between the measurements, the mixture is shaken for 55 seconds.

1.e) Platelet Aggregation in Fibrinogen-Depleted Plasma

To determine platelet aggregation, blood of healthy volunteers of both genders, who had not received any thrombocyte aggregation-influencing medication for the last ten days, is used. The blood is taken up into monovettes (Sarstedt, Nümbrecht, Germany) which contain, as anticoagulant, sodium citrate 3.8% (1 part citrate+9 parts blood).

Preparation of fibrinogen-depleted plasma: To obtain low-platelet plasma, the citrated whole blood is centrifuged at 140 g for 20 min. The low-platelet plasma is admixed in a ratio of 1:25 with reptilase (Roche Diagnostic, Germany) and inverted cautiously. This is followed by 10 min of incubation at 37° C. in a water bath, followed directly by 10 min of incubation on ice. The plasma/reptilase mixture is centrifuged at 1300 g for 15 min, and the supernatant (fibrinogen-depleted plasma) is obtained.

Platelet isolation: To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1300 g for 10 minutes. The platelet pellet is resuspended in wash buffer and centrifuged at 1300 g for 10 minutes. The platelets are resuspended in incubation buffer and adjusted to 400 000 cells/μl, and calcium chloride solution is added to a final concentration of 5 mM (dilution 1/200).

For the aggregation measurements, aliquots (98 μl of fibrinogen-depleted plasma and 80 μl of platelet suspension) are incubated with increasing concentrations of test substance at RT for 10 min. Subsequently, aggregation is triggered by addition of human alpha thrombin in an aggregometer and determined at 37° C. by means of the turbidimetry method according to Born (Born, G. V. R., Cross M. J., The Aggregation of Blood Platelets; *J. Physiol.* 1963, 168, 178-195). The alpha thrombin concentration which just leads to the maximum aggregation is determined individually for each donor.

To calculate the inhibitory activity, the increase in the maximum light transmission (amplitude of the aggregation curve in %) is determined within 5 minutes after addition of the agonist in the presence and absence of test substance, and the inhibition is calculated. The inhibition curves are used to calculate the concentration which inhibits aggregation by 50%.

1.f) Stimulation of Washed Platelets and Analysis in Flow Cytometry

Isolation of washed platelets: Human whole blood is obtained by venipuncture from voluntary donors and transferred into monovettes (Sarstedt, Nümbrecht, Germany) containing sodium citrate as anticoagulant (1 part sodium citrate 3.8%+9 parts whole blood). The monovettes are centrifuged at 90° rotations per minute and 4° C. for a period of 20 minutes (Heraeus Instruments, Germany; Megafuge 1.0RS). The platelet-rich plasma is cautiously removed and transferred into a 50 ml Falcon tube. ACD buffer (44 mM sodium citrate, 20.9 mM citric acid, 74.1 mM glucose) is then added to the plasma. The volume of the ACD buffer corresponds to one quarter of the plasma volume. Centrifuging at 2500 rpm and 4° C. for ten minutes sediments the platelets. Thereafter, the supernatant is cautiously decanted off and discarded. The precipitated platelets are first cautiously resuspended in one milliliter of wash buffer (113 mM sodium chloride, 4 mM disodium hydrogenphosphate, 24 mM sodium dihydrogenphosphate, 4 mM potassium chloride, 0.2 mM ethylene glycol bis(2-aminoethyl)-N,N,N',N'-tetraacetic acid, 0.1% glucose) and then made up with wash buffer to a volume which corresponds to that of the amount of plasma. The wash procedure is repeated. The platelets are precipitated by another ten-minute centrifugation at 2500 rpm and 4° C. and then carefully resuspended in one milliliter of incubation buffer (134 mM sodium chloride, 12 mM sodium hydrogencarbonate, 2.9 mM potassium chloride, 0.34 mM sodium dihydrogencarbonate, 5 mM HEPES, 5 mM glucose, 2 mM calcium chloride and 2 mM magnesium chloride) and adjusted with incubation buffer to a concentration of 300 000 platelets per µl.

Staining and stimulation of the human platelets with human α-thrombin in the presence or absence of a PAR-1 antagonist: The platelet suspension is preincubated with the substance to be tested or the appropriate solvent at 37° C. for 10 minutes (Eppendorf, Germany; Thermomixer Comfort). Platelet activation is triggered by addition of the agonist (0.5 µM or 1 µM α-thrombin; Kordia, the Netherlands, 3281 NIH units/mg; or 30 µg/ml of thrombin receptor activating peptide (TRAP6); Bachem, Switzerland) at 37° and with shaking at 500 rpm. At each of 0, 1, 2.5, 5, 10 and 15 minutes, one aliquot of 50 µl is removed and transferred into one milliliter of singly concentrated CellFix™ solution (Becton Dickinson Immunocytometry Systems, USA). To fix the cells, they are incubated in the dark at 4° C. for 30 minutes. The platelets are precipitated by centrifuging at 600 g and 4° C. for ten minutes. The supernatant is discarded and the platelets are resuspended in 400 µl CellWash™ (Becton Dickinson Immunocytometry Systems, USA). One aliquot of 100 µl is transferred to a new FACS tube. 1 µl of the platelet-identifying antibody and 1 µl of the activation state-detecting antibody are made up to a volume of 100 µl with CellWash™. This antibody solution is then added to the platelet suspension and incubated in the dark at 4° C. for 20 minutes. After staining, the mixture volume is increased by addition of a further 400 µl of CellWash™.

The platelets are identified using a fluorescein isothiocyanate-conjugated antibody directed against human glycoprotein IIb (CD41) (Immunotech Coulter, France; Cat. No. 0649). With the aid of the phycoerythrin-conjugated antibody directed against human glycoprotein P-selectin (Immunotech Coulter, France; Cat. No. 1759), it is possible to determine the activation state of the platelets. P-selectin (CD62P) is localized in the α-granules of resting platelets. However, following in vitro or in vivo stimulation, it is translocated to the external plasma membrane.

Flow cytometry and data evaluation: The samples are analysed in the FACSCalibur™ Flow Cytometry System instrument from Becton Dickinson Immunocytometry Systems, USA, and evaluated and graphically represented with the aid of the CellQuest software, Version 3.3 (Becton Dickinson Immunocytometry Systems, USA). The degree of platelet activation is determined by the percentage of CD62P-positive platelets (CD41-positive events). From each sample, 10 000 CD41-positive events are counted.

The inhibitory effect of the substances to be tested is calculated via the reduction in platelet activation, which relates to the activation by the agonist.

1.g) Platelet Aggregation Measurement Using the Parallel-Plate Flow Chamber

Platelet aggregation is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood). To obtain platelet-rich plasma, the citrated whole blood is centrifuged at 140 g for 20 min. One quarter of the volume of ACD buffer (44.8 mM sodium citrate, 20.9 mM citric acid, 74.1 mM glucose and 4 mM potassium chloride) is added to the PRP, and the mixture is centrifuged at 1000 g for 10 minutes. The platelet pellet is resuspended in wash buffer and centrifuged at 1000 g for 10 minutes. For the perfusion study, a mixture of 40% erythrocytes and 60% washed platelets (200 000/µl) is prepared and suspended in HEPES-tyrode buffer. Platelet aggregation under flow conditions is measured using the parallel-plate flow chamber (B. Nieswandt et al., *EMBO J.* 2001, 20, 2120-2130; C. Weeterings, *Arterioscler Thromb. Vasc. Biol.* 2006, 26, 670-675; J J Sixma, *Thromb. Res.* 1998, 92, 43-46). Glass slides are wetted with 100 µl of a solution of human α-thrombin (dissolved in Tris buffer) at 4° C. overnight α-thrombin in different concentrations, for example 10 to 50 µg/ml) and finally blocked using 2% BSA.

Reconstituted blood is passed over the thrombin-wetted glass slides at a constant flow rate (for example a shear rate of 300/second) for 5 minutes and observed and recorded using a microscope video system. The inhibitory effect of the substances to be tested is determined morphometrically via the reduction in platelet aggregate formation. Alternatively, the inhibition of the platelet activation can be determined by flow cytometry, for example via p-selectin expression (CD62p) (see Method 1.f).

1.h) Platelet Aggregation and Activation Measurement Using the Parallel-Plate Flow Chamber (Anticoagulated Blood, Collagen)

Platelet activation under flow conditions is determined using blood from healthy volunteers of both genders, who had not received any thrombocyte aggregation-influencing medication for the last ten days. The blood is taken up into monovettes (Sarstedt, Nümbrecht, Germany) which contain, as anticoagulant, sodium citrate 3.8% (1 part citrate+9 parts blood).

The measurement of platelet activation is carried out using the parallel-plate flow chamber (B. Nieswandt et al., *EMBO J.* 2001, 20, 2120-2130; C. Weeterings, *Arterioscler Thromb. Vasc. Biol.* 2006, 26, 670-675; J J Sixma, *Thromb. Res.* 1998, 92, 43-46). Glass slides are wetted with 20 µl of collagen suspension (collagen reagent: Horm, Nycomed) at 4° C. overnight (type I collagen in different concentrations, e.g. 1-10 µg/slide) and finally blocked using 2% BSA.

To prevent fibrin clot formation, citrated whole blood is admixed with Pefabloc FG (Pentapharm, final concentration 3 mM) and, by addition of $CaCl_2$ solution (final $Ca^{++}$ concentration 5 mM), passed over the collagen-coated glass slides at a constant flow rate (for example a shear rate of 1000/second) for 5 minutes and observed and recorded using a microscope video system. The inhibitory effect of the substances to be tested is determined morphometrically via the reduction in platelet aggregate formation. Alternatively, the inhibition of the platelet activation can be determined by flow cytometry, for example via p-selectin expression (CD62p) (see Method 1.f).

1.i) Platelet Aggregation and Activation Measurement Using the Parallel-Plate Flow Chamber (Nonanticoagulated Blood, Collagen)

Platelet activation under flow conditions is determined using blood from healthy volunteers of both genders, who had not received any thrombocyte aggregation-influencing medication for the last ten days. The blood is taken up into neutral monovettes (Sarstedt, Nümbrecht, Germany) which do not contain any anticoagulant, and immediately admixed with Pefabloc FG (Pentapharm, final concentration 3 mM) to prevent fibrin clot formation. Test substances dissolved in DMSO are added simultaneously with Pefablock FG and introduced without further incubation into the parallel-plate flow chamber. The measurement of platelet activation is conducted by morphometry or flow cytometry in the collagen-coated parallel-plate flow chamber, as described in Method 1.h).

2.) Ex Vivo Assay 2.a) Platelet Aggregation (Primates, Guinea Pigs)

Awake or anaesthetized guinea pigs or primates are treated orally, intravenously or intraperitoneally with test substances in suitable formulations. As a control, other guinea pigs or primates are treated in an identical manner with the corresponding vehicle. Depending on the mode of application, blood is obtained from the deeply anaesthetized animals by puncture of the heart or of the aorta for different times. The blood is transferred into monovettes (Sarstedt, Nümbrecht, Germany) which, as anticoagulant, contain sodium citrate 3.8% (1 part citrate solution+9 parts blood). To obtain platelet-rich plasma, the citrated whole blood is centrifuged at 140 g for 20 min.

Aggregation is triggered by addition of a thrombin receptor agonist (TRAP6, SFLLRN, 50 µg/ml; in each experiment, the concentration is determined for each animal species) in an aggregometer and determined using the turbidimetry method according to Born (Born, G. V. R., Cross M. J., The Aggregation of Blood Platelets; *J. Physiol.* 1963, 168, 178-195) at 37° C.

To measure the aggregation, the maximum increase in the light transmission (amplitude of the aggregation curve in %) is determined 5 minutes after addition of the agonist. The inhibitory effect of the administered test substances in the treated animals is calculated via the reduction in aggregation, based on the mean of the control animals.

In addition to measurement of aggregation, the inhibition of platelet activation can be determined by flow cytometry, for example via p-selectin expression (CD62p) (see Method 1.f).

2.b) Platelet Aggregation and Activation Measurement in the Parallel-Plate Flow Chamber (Primates)

Awake or anaesthetized primates are treated orally, intravenously or intraperitoneally with test substances in suitable formulations. As a control, other animals are treated in an identical manner with the corresponding vehicle. According to the mode of administration, blood is obtained from the animals by venipuncture for different times. The blood is transferred into monovettes (Sarstedt, Nümbrecht, Germany) which, as anticoagulant, contain sodium citrate 3.8% (1 part citrate solution+9 parts blood). Alternatively, nonanticoagulated blood can be taken with neutral monovettes (Sarstedt). In both cases, the blood is admixed with Pefabloc FG (Pentapharm, final concentration 3 mM) to prevent fibrin clot formation.

Citrated whole blood is recalcified before the measurement by adding $CaCl_2$ solution (final $Ca^{++}$ concentration 5 mM). Nonanticoagulated blood is introduced directly into the parallel-plate flow chamber for analysis. The measurement of platelet activation is conducted by morphometry or flow cytometry in the collagen-coated parallel-plate flow chamber, as described in Method 1.h).

3.) In Vivo Assays 3.a) Thrombosis Model

The inventive compounds can be studied in thrombosis models in suitable animal species in which thrombin-induced platelet aggregation is mediated via the PAR-1 receptor. Suitable animal species are guinea pigs and, in particular, primates (cf.: Lindahl, A. K., Scarborough, R. M., Naughton, M. A., Harker, L. A., Hanson, S. R., *Thromb Haemost* 1993, 69, 1196; Cook J J, Sitko G R, Bednar B, Condra C, Mellott M J, Feng D-M, Nutt R F, Shager J A, Gould R J, Connolly T M, *Circulation* 1995, 91, 2961-2971; Kogushi M, Kobayashi H, Matsuoka T, Suzuki S, Kawahara T, Kajiwara A, Hishinuma I, *Circulation* 2003, 108 *Suppl.* 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b) Impaired Coagulation and Organ Dysfunction in the Case of Disseminated Intravasal Coagulation (DIC)

The inventive compounds can be studied in models of DIC and/or sepsis in suitable animal species. Suitable animal species are guinea pigs and, in particular, primates, and for the study of endothelium-mediated effects also mice and rats (cf.: Kogushi M, Kobayashi H, Matsuoka T, Suzuki S, Kawahara T, Kajiwara A, Hishinuma I, *Circulation* 2003, 108 *Suppl.* 17, IV-280; Derian C K, Damiano B P, Addo M F, Darrow A L, D'Andrea M R, Nedelman M, Zhang H-C, Maryanoff B E, Andrade-Gordon P, *J. Pharmacol. Exp. Ther.* 2003, 304, 855-861; Kaneider N C et al., *Nat Immunol*, 2007, 8, 1303-12; Camerer E et al., *Blood*, 2006, 107, 3912-21; Riewald M et al., *J Biol Chem*, 2005, 280, 19808-14). Alternatively, it is possible to use guinea pigs which have been pretreated with inhibitors of PAR-3 and/or PAR-4 (Leger A J et al., *Circulation* 2006, 113, 1244-1254), or transgenic PAR-3- and/or PAR-4-knockdown guinea pigs.

3.b.1) Thrombin-Antithrombin Complexes

Thrombin-antithrombin complexes (referred to hereinafter as "TAT") are a measure of the thrombin formed endogenously by coagulation activation. TATs are determined via an ELISA assay (Enzygnost TAT micro, Dade-Behring). Plasma is obtained from citrated blood by centrifugation. 50 µl of TAT sample buffer are added to 50 µl of plasma, shaken briefly and incubated at room temperature for 15 min. The samples are filtered with suction, and the well is washed 3 times with wash buffer (300 µl/well). Between the wash steps, the plate is tapped to remove any residual wash buffer. Conjugate solution (100 µl) is added and the mixture is incubated at room temperature for 15 min. The samples are filtered with suction, and the well is washed 3 times with wash buffer (300 µl/well). The chromogenic substrate (100 µl/well) is then added, the mixture is incubated in the dark at room temperature for 30 min, stop solution (100 µl/well) is added, and the development of colour at 492 nm is measured (Safire plate reader).

3.b.2) Parameters of Organ Dysfunction

Various parameters are determined, which allow conclusions to be drawn with respect to the functional restriction of various internal organs owing to the administration of LPS, and the therapeutic effect of test substances can be assessed. Citrated blood or, if appropriate, lithium heparin blood, is centrifuged, and the plasma is used to determine the parameters. Typically, the following parameters are determined: creatinine, urea, aspartate aminotransferase (AST), alanine aminotransferase (ALT), total bilirubin, lactate dehydrogenase (LDH), total protein, total albumin and fibrinogen. The values give information regarding kidney function, liver function, cardiovascular function and vascular function.

3.b.3) Parameters of Inflammation

The extent of the inflammatory reaction triggered by endotoxin can be demonstrated by the increase in inflammation mediators, for example interleukins (1, 6, 8 and 10), tumour necrosis factor alpha or monocyte chemoattractant protein-1, in the plasma. ELISAs or the Luminex system may be used for this purpose.

3.c) Antitumour Activity

The inventive compounds can be tested in models of cancer, for example in the human breast cancer model in immunodeficient mice (cf.: S. Even-Ram et. al., *Nature Medicine,* 1988, 4, 909-914).

3.d) Antiangiogenetic Activity

The inventive compounds can be tested in in vitro and in vivo models of angiogenesis (cf.: Caunt et al., *Journal of Thrombosis and Haemostasis,* 2003, 10, 2097-2102; Haralabopoulos et al., *Am J Physiol,* 1997, C239-C245; Tsopanoglou et al., *JBC,* 1999, 274, 23969-23976; Zania et al., *JPET,* 2006, 318, 246-254).

3.e) Blood Pressure- and Pulse-Modulating Activity

The inventive compounds can be tested in in vivo models for their action on arterial blood pressure and heart rate. To this end, rats (for example Wistar) are provided with implantable radiotelemetry units, and an electronic data acquisition and storage system (Data Sciences, Minn., USA) consisting of a chronically implantable transducer/transmitter unit in combination with a liquid-filled catheter is employed. The transmitter is implanted into the peritoneal cavity, and the sensor catheter is positioned in the descending aorta. The inventive compounds can be administered (for example orally or intravenously). Prior to the treatment, the mean arterial blood pressure and the heart rate of the untreated and treated animals are measured, and it is ensured that they are in the range of about 131-142 mmHg and 279-321 beats/minute. PAR-1-activating peptide (SFLLRN; for example doses between 0.1 and 5 mg/kg) is administered intravenously. Blood pressure and heart rate are measured at different time intervals and periods with and without PAR-1-activating peptide and with and without an inventive compound (cf.: Cicala C et al., *The FASEB Journal,* 2001, 15, 1433-5; Stasch J P et al., *British Journal of Pharmacology* 2002, 135, 344-355).

3.f) Thrombosis Model

A further in vivo thrombosis assay which is suitable for determining the efficacy of the compounds of the present invention is described in Tucker E I, Marzec U M, White T C, Hurst S, Rugonyi S, McCarty Off, Gailani D, Gruber A, Hanson S R: Prevention of vascular graft occlusion and thrombus-associated thrombin generation by inhibition of factor XI. *Blood* 2009, 113, 936-944.

4.) Determination of the Solubility

Preparation of the Starting Solution (Original Solution):

At least 1.5 mg of the test substance are weighed out accurately into a wide-mouth 10 mm screw V-vial (from Glastechnik Gräfenroda GmbH, Art. No. 8004-WM-H/V15µ) with fitting screw cap and septum, DMSO is added to a concentration of 50 mg/ml and the vial is vortexed for 30 minutes.

Preparation of the Calibration Solutions:

The pipetting steps necessary are effected in 1.2 ml 96-deep well plates (DWP) with the aid of a liquid-handling robot. The solvent used is a mixture of acetonitrile/water 8:2.

Preparation of the starting solution of calibration solutions (stock solution): 833 µl of the solvent mixture are added to 10 µl of the original solution (concentration=600 µg/ml), and the mixture is homogenized. 1:100 dilutions in separate DWPs are prepared from each test substance, and these are homogenized in turn.

Calibration solution 5 (600 ng/ml): 270 µl of the solvent mixture are added to 30 µl of the stock solution, and the mixture is homogenized.

Calibration solution 4 (60 ng/ml): 270 µl of the solvent mixture are added to 30 µl of the calibration solution 5, and the mixture is homogenized.

Calibration solution 3 (12 ng/ml): 400 µl of the solvent mixture are added to 100 µl of the calibration solution 4, and the mixture is homogenized.

Calibration solution 2 (1.2 ng/ml): 270 µl of the solvent mixture are added to 30 µl of the calibration solution 3, and the mixture is homogenized.

Calibration solution 1 (0.6 ng/ml): 150 µl of the solvent mixture are added to 150 µl of the calibration solution 2, and the mixture is homogenized.

Preparation of the Sample Solutions:

The pipetting steps necessary are effected in 1.2 ml 96-well DWPs with the aid of a liquid-handling robot. 1000 µl of PBS buffer pH 6.5 are added to 10.1 µl of the stock solution. (PBS buffer pH 6.5: 61.86 g of sodium chloride, 39.54 g of sodium dihydrogenphosphate and 83.35 g of 1 N aqueous sodium hydroxide solution are weighed out into a 1 litre standard flask and made up to the mark with water, and the mixture is stirred for about 1 hour. 500 ml of this solution are introduced into a 5 litre measuring flask and made up to the mark with water. The pH is adjusted to 6.5 using 1 N aqueous sodium hydroxide solution.)

Procedure:

The pipetting steps necessary are effected in 1.2 ml 96-well DWPs with the aid of a liquid-handling robot. The sample solutions prepared in this manner are shaken at 1400 rpm and at 20° C. using a variable temperature shaker for 24 hours. 180 µl are removed from each of these solutions and transferred into Beckman Polyallomer centrifuge tubes. These solutions are centrifuged at about 223 000×g for 1 hour. From each sample solution, 100 µl of the supernatant are removed and diluted 1:10 and 1:1000 with PBS buffer 6.5.

Analysis:

The samples are analysed by means of HPLC/MS-MS. The test compound is quantified by means of a five-point calibration curve. The solubility is expressed in mg/l. Analysis sequence: 1) blank (solvent mixture); 2) calibration solution 0.6 ng/ml; 3) calibration solution 1.2 ng/ml; 4) calibration solution 12 ng/ml; 5) calibration solution 60 ng/ml; 6) calibration solution 600 ng/ml; 7) blank (solvent mixture); 8) sample solution 1:1000; 9) sample solution 1:10.

HPLC/MS-MS Method:

HPLC: Agilent 1100, quat. pump (G1311A), autosampler CTC HTS PAL, degasser (G1322A) and column thermostat (G1316A); column: Oasis HLB 20 mm×2.1 mm, 25µ; temperature: 40° C.; eluent A: water+0.5 ml of formic acid/1; eluent B: acetonitrile+0.5 ml of formic acid/1; flow rate: 2.5 ml/min; stop time 1.5 min; gradient: 0 min 95% A, 5% B; ramp: 0-0.5 min 5% A, 95% B; 0.5-0.84 min 5% A, 95% B; ramp: 0.84-0.85 min 95% A, 5% B; 0.85-1.5 min 95% A, 5% B.

MS/MS: WATERS Quattro Micro Tandem MS/MS; Z-Spray API interface; HPLC-MS inlet splitter 1:20; measurement in the ESI mode.

5.) In Vitro Clearance Determinations with Hepatocytes

Incubations with fresh primary hepatocytes are carried out at 37° C. in a total volume of 1.5 ml with a modified Janus® robot (Perkin Elmer) while shaking. The incubations typically contain 1 million living liver cells/ml, approx 1 µM substrate and 0.05 M potassium phosphate buffer (pH=7.4). The final acetonitrile concentration in the incubation is ≦1%.

Aliquots of 125 µl are withdrawn from the incubations after 2, 10, 20, 30, 50, 70 and 90 min and transferred into 96-well filter plates (0.45 µm low-binding hydrophilic PTFE; Millipore: MultiScreen Solvinert). Each of these contain 250 µl of acetonitrile to stop the reaction. After the centrifugation, the filtrates are analysed by MS/MS (typically API 3000).

The in vitro clearances are calculated from the half-lives of the substance degradation, using the following equation:

$$CL'_{intrinsic}[ml/(min \cdot kg)] = (0.693/\text{in vitro } t1/2[min]) \cdot (\text{liver weight } [g \text{ liver}/kg \text{ bodyweight}]) \cdot (\text{cell count } [1.1 \cdot 10^8]/\text{liver weight } [g])/(\text{cell count } [1 \cdot 10^6]/\text{incubation volume } [ml])$$

The $CL_{blood}$ is calculated without taking into account the free fraction ("nonrestricted well stirred model") by the following equation:

$$CL_{blood} \text{ well-stirred}[l/(h \cdot kg)] = (Q_H[l/(h \cdot kg)] \cdot CL'_{intrinsic}[l/(h \cdot kg)])/(Q_H[l/(h \cdot kg)] + CL'_{intrinsic}[l/(h \cdot kg)])$$

The species-specific extrapolation factors used for the calculation are summarized in the following table:

|  | male/female | | | | | |
| --- | --- | --- | --- | --- | --- | --- |
|  | Mouse m | Mouse f | Rat m/f | Dog m/f | Cyno f | Man m/f |
| Cell number/g liver [10⁶ cells] | 110 | 110 | 110 | 110 | 110 | 110 |
| Liver [g]/kg bodyweight | 50 | 43 | 32 | 39 | 30 | 21 |
| Liver blood flow [l/(h · kg)] | 5.4 | 5.4 | 4.2 | 2.1 | 2.5 | 1.3 |

Fmax values which state the maximum possible bioavailability—based on the hepatic extraction—are calculated as follows:

$$F_{max} \text{ well-stirred}[\%] = (1 - (CL_{blood} \text{ well-stirred}[l/(h \cdot kg)]/Q_H[l/(h \cdot kg)])) \cdot 100$$

6.) Determination of In Vivo Pharmacokinetics

To determine the in vivo pharmacokinetics, the test substances are dissolved in different formulation media (e.g. plasma, ethanol, DMSO, PEG400, etc.) or mixtures of these solubilizers, and administed intravenously or perorally to mice, rats, dogs or monkeys. Intravenous administration is effected either as a bole or as an infusion. The doses administered are in the range from 0.1 to 5 mg/kg. Blood samples are taken by means of a catheter or as sacrifice plasma at different times over a period of up to 26 h. In addition, some organ, tissue and urine samples are also obtained. The substances are determined quantitatively in the test samples by means of calibration samples which are established in the particular matrix. Proteins present in the samples are removed by precipitation with acetonitrile or methanol. Subsequently, the samples are separated by means of HPLC on a 2300 HTLC system (Cohesive Technologies, Franklin, Mass., USA) or Agilent 1200 (Boblingen, Germany) using reverse-phase columns. The HPLC system is coupled via a turbo ion spray interface to an API 3000 or 4000 triple quadrupole mass spectrometer (Applied Biosystems, Darmstadt, Germany). The plot of plasma concentration against time is evaluated using a validated kinetics evaluation program.

C) Working Examples of Pharmaceutical Compositions

The inventive substances can be converted in pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% solution (m/m) of the PVP in water. The granules are dried and then mixed with the magnesium stearate for 5 min. This mixture is compressed in a conventional tablet press (see above for tablet format).

Oral Suspension:

Composition:

1000 mg of the compound of Example 1, 1000 mg of ethanol (96%), 400 mg of Rhodigel (xanthan gum) (from FMC, USA) and 99 g of water.

A single dose of 100 mg of the inventive compound corresponds to 10 ml of oral suspension.

Production:

The Rhodigel is suspended in ethanol, and the compound of Example 1 is added to the suspension. The water is added while stirring. The mixture is stirred for approx. 6 h until the Rhodigel has finished swelling.

Intravenously Administrable Solution:

Composition:

1 mg of the compound of Example 1, 15 g of polyethylene glycol 400 and 250 g of water for injections.

Production:

The compound of Example 1 is dissolved together with polyethylene glycol 400 by stirring in the water. The solution is sterile-filtered (pore diameter 0.22 µm) and dispensed under aseptic conditions into heat-sterilized infusion bottles. The latter are closed with infusion stoppers and crimped caps.

The invention claimed is:

1. A method of treatment of arterial thromboembolic disorders in humans and animals comprising administering to the human or animal an therapeutically effective amount of a compound of formula (I):

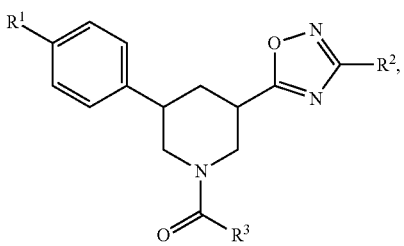

(I)

in which

R¹ is trifluoromethyl, 1,1-difluoroethyl, 2,2-difluoroethyl, 2,2,2-trifluoroethyl, difluoromethoxy, trifluoromethoxy or ethyl, R² is 2-hydroxyeth-1-yl, 2-methoxyeth-1-yl, 2-ethoxyeth-1-yl, cyclopropyl or 1-methoxycycloprop-1-yl, R³ is a group of the formula

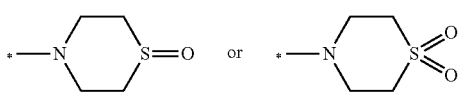

where

* is the point of attachment to the carbonyl group, or a salt thereof.

2. The method of claim 1, wherein in the compound of formula (I),

R¹ is trifluoromethyl, 2,2,2-trifluoroethyl, trifluoromethoxy or ethyl,

R² is 2-methoxyeth-1-yl, cyclopropyl or 1-methoxycycloprop-1-yl,

R³ is a group of the formula

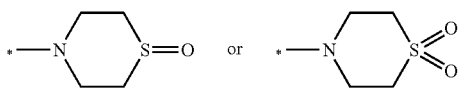

where

* is the point of attachment to the carbonyl group.

3. The method of claim 1, wherein in the compound of formula (I),

R¹ is trifluoromethoxy,

R² is 2-methoxyeth-1-yl or cyclopropyl, and

R³ is a group of the formula

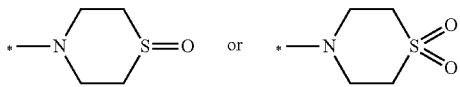

where

* is the point of attachment to the carbonyl group.

4. The method of claim 1, wherein in the compound of formula (I)

R1 is trifluoromethoxy,

R2 is cyclopropyl, and

R3 is a group of the formula

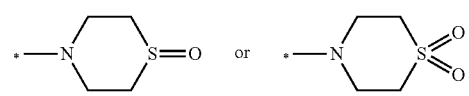

where

* is the point of attachment to the carbonyl group.

5. The method of claim 1, wherein the phenyl substituent and the 1,2,4-oxadiazol-5-yl substituent of the compound of formula (I) bonded to the piperidine ring are in cis positions to one another.

6. The method of claim 1, wherein the carbon atom to which the phenyl substituent is bonded in the compound of formula (I) is in an S configuration and the carbon atom to which the 1,2,4-oxadiazol-5-yl substituent is bonded is also in an S configuration.

7. The method of claim 1, wherein the compound of formula (I) is has the formula:

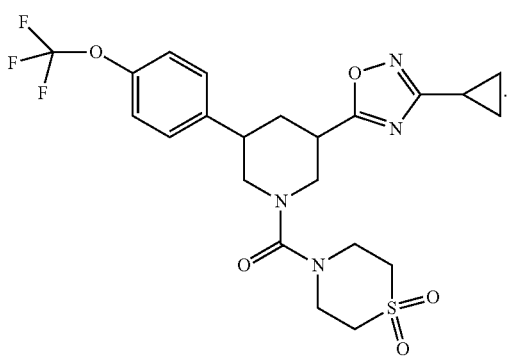 [SMILES: O=C(N1CCS(=O)(=O)CC1)N1CC(c2ccc(OC(F)(F)F)cc2)CC(c2nc(C3CC3)no2)C1]

8. The method of claim 7, wherein the compound is a cis stereoisomer.

9. The method of claim 7, wherein the compound of formula (I) is {3(3-Cyclopropyl-1,2,4-oxadiazol-5-yl)-5-[4-(trifluoromethoxy) phenyl]piperidin-1-yl}(1,1-dioxidothiomorpholin-4- yl)methanone [cis isomer], or a salt thereof.

10. The method of claim 1, wherein the compound of formula (I) is administered as a pharmaceutical composition, comprising the compound of formula (I) and an inert non-toxic pharmaceutically acceptable excipient.

11. A method of treatment of a thromboembolic disorder in a human or animal, wherein the thromboembolic disorder is selected from the group consisting of: ST-segment elevation myocardial infarction (STEMI) and non-ST-segment elevation myocardial infarction (non-STEMI), stable angina pectoris, unstable angina pectoris, reocclusions and restenoses after coronary interventions, peripheral arterial occlusion diseases, pulmonary embolisms, transitory ischaemic attacks and also thrombotic and thromboembolic stroke, comprising administering to the human or animal a therapeutically effective amount of a compound of formula (I):

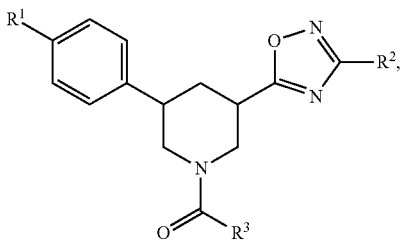
(I)

in which
R¹ is trifluoromethyl, 1,1-difluoroethyl, 2,2-difluoroethyl, 2,2,2-trifluoroethyl, difluoromethoxy, trifluoromethoxy or ethyl,
R² is 2-hydroxyeth-1-yl, 2-methoxyeth-1-yl, 2-ethoxyeth-1-yl, cyclopropyl or 1-methoxycycloprop-1-yl,
R³ is a group of the formula

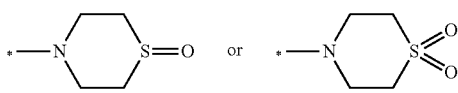

where
* is the point of attachment to the carbonyl group, or a salt thereof.

12. A method of treatment of a thromboembolic complication connected with microangiopathic haemolytic anaemias or extracorporeal circulation comprising administering to a patient in need thereof a therapeutically effective, amount of a compound of formula (I) of claim 1.

13. A method of treatment of a pulmonary disorder wherein the pulmonary disorder is selected from the group consisting of pulmonary fibrosis, pulmonary hypertension, and an inflammatory pulmonary disorder, comprising administering to a patient in need thereof a therapeutically effective amount of a compound of formula (I):

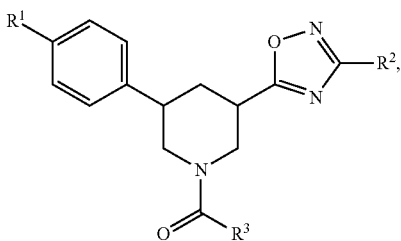
(I)

in which
R¹ is trifluoromethyl, 1,1-difluoroethyl, 2,2-difluoroethyl, 2,2,2-trifluoroethyl, difluoromethoxy, trifluoromethoxy or ethyl,
R² is 2-hydroxyeth-1-yl, 2-methoxyeth-1-yl, 2-ethoxyeth-1-yl, cyclopropyl or 1-methoxycycloprop-1-yl,
R³ is a group of the formula

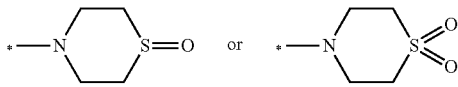

where
* is the point of attachment to the carbonyl group, or a salt thereof.

14. The method of claim 13, wherein the compound of formula (I) is administered as a pharmaceutical composition, comprising the compound of formula (I) and an inert nontoxic pharmaceutically acceptable excipient.

15. The method of claim 11, wherein in the compound of formula (I),
R¹ is trifluoromethyl, 2,2,2-trifluoroethyl, trifluoromethoxy or ethyl,
R² is 2-methoxyeth-1-yl, cyclopropyl or 1-methoxycycloprop-1-yl,
R³ is a group of the formula

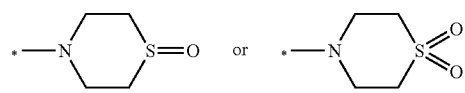

where
* is the point of attachment to the carbonyl group.

16. The method of claim 11, wherein in the compound of formula (I),
R¹ is trifluoromethoxy,
R² is 2-methoxyeth-1-yl or cyclopropyl, and
R³ is a group of the formula

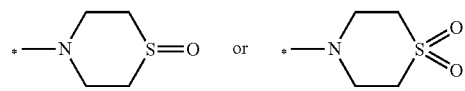

where
* is the point of attachment to the carbonyl group.

17. The method of claim 11, wherein in the compound of formula (I)
R1 is trifluoromethoxy,
R2 is cyclopropyl, and
R3 is a group of the formula

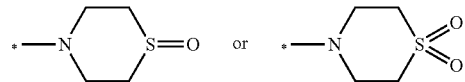

where
* is the point of attachment to the carbonyl group.

18. The method of claim 11, wherein the phenyl substituent and the 1,2,4-oxadiazol-5-yl substituent of the compound of formula (I) bonded to the piperidine ring are in cis positions to one another.

19. The method of claim 11, wherein the carbon atom to which the phenyl substituent is bonded in the compound of formula (I) is in an S configuration and the carbon atom to which the 1,2,4-oxadiazol-5-yl substituent is bonded is also in an S configuration.

20. The method of claim 11, wherein the compound of formula (I) is has the formula:

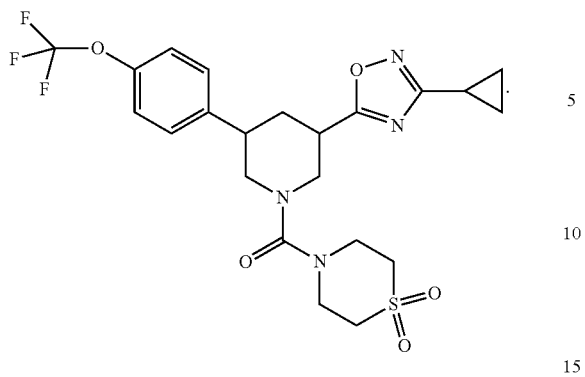

21. The method of claim 20, wherein the compound is a cis stereoisomer.

22. The method of claim 20, wherein the compound of formula (I) is {3-(3-Cyclopropyl-1,2,4-oxadiazol-5-yl)-5-[4-(trifluoromethoxy) phenyl]piperidin-1-yl}(1,1-dioxidothiomorpholin-4-yl)methanone [cis isomer], or a salt thereof.

23. The method of claim 11, wherein the coronary intervention is selected from the group consisting of angioplasty, stent implantation, and aortocoronary bypass.

* * * * *

UNITED STATES PATENT AND TRADEMARK OFFICE
CERTIFICATE OF CORRECTION

| | | |
|---|---|---|
| PATENT NO. | : 8,440,657 B2 | Page 1 of 1 |
| APPLICATION NO. | : 13/322593 | |
| DATED | : May 14, 2013 | |
| INVENTOR(S) | : Dirk Heimbach et al. | |

It is certified that error appears in the above-identified patent and that said Letters Patent is hereby corrected as shown below:

In the Specification

On column 93, line 55 (heading of Table B), replace "nM" with --µM--

Signed and Sealed this
Third Day of June, 2014

Michelle K. Lee
*Deputy Director of the United States Patent and Trademark Office*